United States Patent [19]

Hanagan

[11] Patent Number: 4,723,987
[45] Date of Patent: Feb. 9, 1988

[54] HERBICIDAL SULFONAMIDES

[75] Inventor: Mary A. Hanagan, Newark, Del.

[73] Assignee: E. I. Du Pont de Nemours and Company, Wilmington, Del.

[21] Appl. No.: 853,094

[22] Filed: Apr. 22, 1986

Related U.S. Application Data

[63] Continuation-in-part of Ser. No. 732,091, May 9, 1985, abandoned.

[51] Int. Cl.⁴ .................. C07D 401/14; C07D 401/12; C07D 471/04; C07D 491/052; A01N 43/54; A01N 43/90; A01N 43/72

[52] U.S. Cl. ............................................ 71/90; 71/91; 71/92; 71/86; 71/87; 544/243; 544/244; 544/255; 544/278; 544/279; 544/295; 544/296; 544/320; 544/321; 544/324; 544/327; 544/328; 544/331; 544/2; 544/3; 544/5; 544/10; 544/47; 544/48; 544/229; 544/235; 544/236; 544/232; 544/65; 544/66; 544/67; 544/68; 544/69; 544/69; 544/90; 544/91; 544/92; 544/93; 544/95; 544/105; 544/6; 544/70; 544/230

[58] Field of Search .................. 71/90, 91, 92, 86, 87; 544/243, 244, 255, 278, 279, 295, 296, 320, 321, 324, 327, 328, 331, 2, 3, 5, 10, 47, 48, 229, 235, 236, 232, 65, 66, 67, 68, 69, 90, 91, 92, 93, 95, 105, 6, 70, 230

[56] References Cited

U.S. PATENT DOCUMENTS 4,369,320  1/1983  Levitt et al. .................. 544/320

Primary Examiner—John M. Ford

[57] ABSTRACT

Sulfonamides such as N-[(4,6-dimethoxypyrimidin-2-yl)aminocarbonyl]-1,3-dihydro-6-methyl-3-oxofuro[3,4-c]pyridine-4-sulfonamide are useful as herbicides and plant growth regulants.

55 Claims, No Drawings

HERBICIDAL SULFONAMIDES

RELATED APPLICATION

This application is a continuation-in-part of application U.S. Ser. No. 732,091, filed May 9, 1985, now abandoned.

BACKGROUND OF THE INVENTION

Herbicidal sulfonamides such as N-[(4,6-dimethoxypyrimidin-2-yl)aminocarbonyl]-1,3-dihydro-6-methyl-3-oxofuro[3,4-c]pyridine-4-sulfonamide are useful as agricultural chemicals and, in particular, as herbicides and growth regulants.

European Publication No. 13,480 (published July 23, 1980) discloses herbicidal pyridine-2-, -3- and -4-sulfonylureas.

U.S. Pat. No. 4,456,469 issued 6/29/84 discloses herbicidal pyridine-3-sulfonylureas of the formula

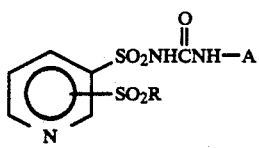

wherein

R is $C_1$–$C_6$ alkyl, $C_3$–$C_6$ alkenyl, $C_2$–$C_4$ alkoxyalkyl or $C_5$–$C_6$ cycloalkyl; and

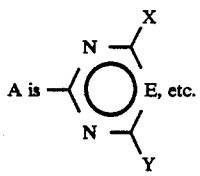

U.S. Pat. No. 4,465,506 issued 8/14/84 discloses herbicidal sulfonylureas of Formula I, II and III

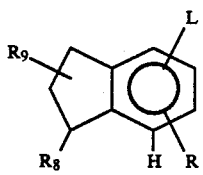 I

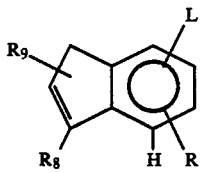 II

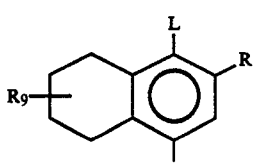 III wherein

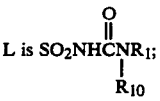

R is, inter alia, H, Cl, Br, $NO_2$, $C_1$–$C_3$ alkyl;

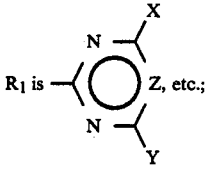

$R_8$ is H, $CH_3$ or Cl;
$R_9$ is H or $CH_3$; and
$R_{10}$ is H or $CH_3$.

U.S. Pat. No. 4,369,320 issued 1/18/83 discloses herbicidal quinoline sulfonylureas of the formula

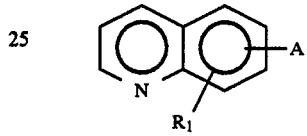

wherein

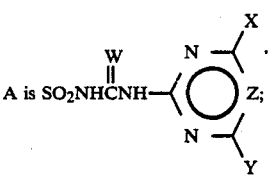

W is O or S; and
$R_1$ is, inter alia, H, Cl, F, Br, $OCH_3$, $CH_3$, or $NO_2$.

EP-A-79,683 discloses herbicidal sulfonylureas, including those of general Formulae IV and V:

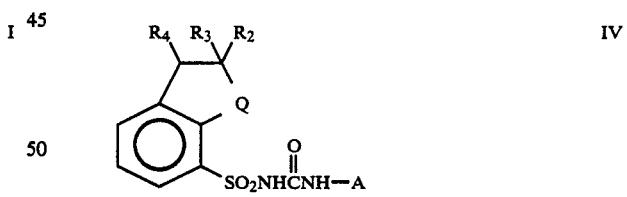 IV

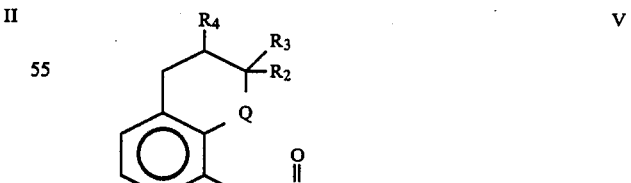 V wherein

Q is O, S or $SO_2$;
$R_2$ is H or $C_1$–$C_3$ alkyl;
$R_3$ is H or $CH_3$; and
$R_4$ is H or $CH_3$.

EP-A-107,979 discloses herbicidal sulfonylureas of formula

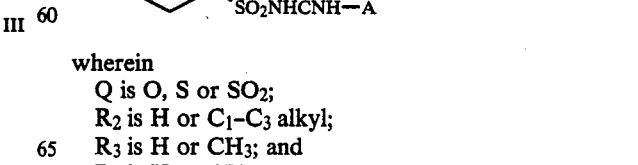

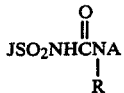

wherein
J is, among other values,

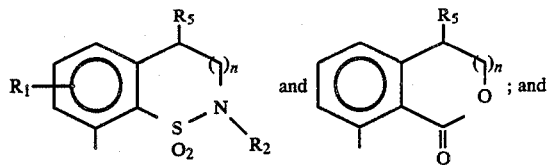

A is a heterocyclic pyrimidine, triazine, triazole or a derivative thereof.

South African Patent Application No. 83/5165 (Swiss priority 7/16/82, published 1/16/84) discloses herbicidal sulfonamides of the formula

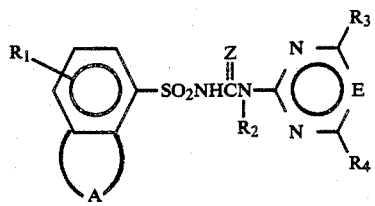

wherein
A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or SO$_2$— group.

South African Patent Application No. 84/3522 (Swiss priority 5/11/83, published 11/11/84) discloses herbicidal sulfonamides of formula

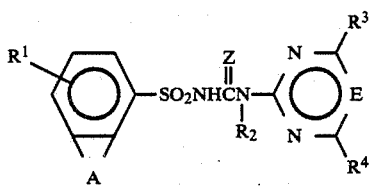

wherein
A is an unsubstituted or substituted unsaturated bridge of 4 atoms, of the formula —CH=CH—Y—, wherein Y is a bridge member of 2 atoms which is selected from the series consisting of —NH—CO—, —NH—SO$_2$—, —S—CO—, —S—SO$_2$—, —O—CO— or —O—SO$_2$—.

The need still exists, however, for general and selective herbicides.

SUMMARY OF THE INVENTION

This invention relates to novel compounds of Formula I, suitable agricultural compositions containing them and their method-of-use as general preemergence and/or postemergence herbicides or plant growth regulants.

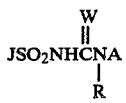

wherein

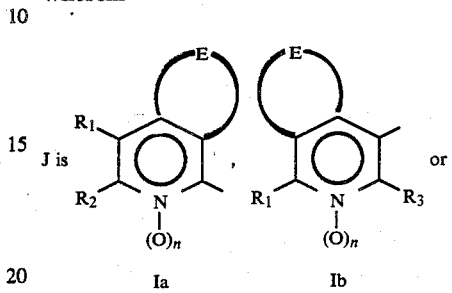

E is a bridge of 3 or 4 atoms, which may be substituted or unsubstituted, containing 0–2 heteroatoms selected from the group consisting of oxygen, sulfur and nitrogen, and also containing 1–4 atoms of carbon, said bridge together with two carbon attachment sites forming a partially saturated 5- or 6-membered carbocyclic or heterocyclic ring; or E is a bridge of 3 or 4 atoms, which may be substituted or unsubstituted, containing 0–1 heteroatoms selected from oxygen or sulfur, 0–2 heteroatoms of nitrogen and 1–4 atoms of carbon, said bridge together with two carbon attachment sites forming a fully unsaturated 5- or 6-membered carbocyclic or heterocyclic ring, with the proviso that when E contains two atoms of oxygen or sulfur, they must be separated by at least one atom of carbon, and that oxygen and sulfur are only linked to each other if the sulfur is in the form of SO or SO$_2$; in the bridging group E, sulfur may take the form of S, SO or SO$_2$, and one of the atoms of carbon may be a carbonyl, thiocarbonyl or the cyclic 5- and 6-membered ketals thereof; when one of the bridging atoms is a substituted carbon, the substituent on said carbon includes H, halogen, C$_1$–C$_4$ alkyl, C$_1$–C$_4$ haloalkyl, C$_3$–C$_4$ alkenyl, C$_3$–C$_4$ haloalkenyl, C$_3$–C$_4$ alkynyl, C$_3$–C$_4$ haloalkynyl, C$_1$–C$_3$ alkoxycarbonyl, CN, NO$_2$, OH, C$_1$–C$_3$ alkoxy, C$_1$–C$_3$ haloalkoxy, C$_1$–C$_3$ alkylthio, C$_1$–C$_3$ alkylsulfinyl, C$_1$–C$_3$ alkylsulfonyl, C$_1$–C$_3$ alkylcarbonyl, C$_1$–C$_3$ alkylsulfamoyl, di(C$_1$–C$_3$ alkyl)sulfamoyl and C$_1$–C$_2$ alkyl substituted with C$_1$–C$_2$ alkoxy, C$_1$–C$_2$ alkylthio or CN; when the bridging atom is nitrogen (other than nitrogen in the form of a cyclic sulfonamide), substituents on said nitrogen include H, C$_1$–C$_4$ alkyl, C$_1$–C$_4$ haloalkyl, C$_3$–C$_4$ alkenyl, C$_3$–C$_4$ haloalkenyl, C$_3$–C$_4$ alkynyl, C$_3$–C$_4$ haloalkynyl, C$_1$–C$_3$ alkoxy, C$_1$–C$_4$ alkylcarbonyl, C$_1$–C$_3$ alkoxycarbonyl, C$_1$–C$_3$ alkylaminocarbonyl or C$_1$–C$_4$ alkylsulfonyl; when the bridging atom is nitrogen in the form of a cyclic sulfonamide, then the nitrogen is substituted by $R_6$ as defined below;

W is O or S;

R is H or $CH_3$;

n is 0 or 1;

$R_1$ is H, $CH_3$, $OCH_3$ or Cl;

$R_2$ is H, $C_1$-$C_3$ alkyl, Cl, Br, F, $C_1$-$C_3$ alkoxy, $C_1$-$C_3$ alkylthio, $CF_3$, $CH_2OCH_3$, $CH_2SCH_3$ or $CH_2CN$;

$R_3$ is H, $C_1$-$C_3$ alkyl, halogen, $C_1$-$C_3$ alkoxy, $C_1$-$C_3$ alkylthio, $C_1$-$C_2$ alkylsulfonyl, $C_1$-$C_2$ alkylcarbonyl, $C_1$-$C_2$ alkoxycarbonyl, $C_3$-$C_4$ alkenyl, $NO_2$, $NH_2$, $C_1$-$C_2$ alkylamino, di($C_1$-$C_2$)alkylamino, $C_1$-$C_2$ alkylsulfamoyl, di($C_1$-$C_2$)alkylsulfamoyl, ($C_1$-$C_2$ alkyl)aminocarbonyl, di($C_1$-$C_2$ alkyl)aminocarbonyl or $C_3$-$C_4$ alkynyl;

$R_6$ is H, $R_8'$, $SR_8'$, $SO_2R_8$, $OR_8'$, $C(O)R_8$, L, C(O)L, $CO_2R_8'$, $(CO)_2OR_8'$, $(CO)_2R_8'$, $C(O)NR_9R_{10}$, C(O)NRA, $C(S)SR_8'$, $NH_2$, $NR_9R_{10}$, OH, CN, $P(O)R_{11}R_{12}$, $P(S)R_{11}R_{12}$ or $Si(CH_3)_2R_{13}$;

$R_8$ is $C_1$-$C_{10}$ alkyl, $C_3$-$C_{10}$ alkoxyalkoxyalkyl, $C_2$-$C_{10}$ alkenyl, $C_3$-$C_{10}$ epoxyalkyl, $C_2$-$C_{10}$ alkynyl, $C_3$-$C_6$ cycloalkyl, $C_4$-$C_7$ cycloalkylalkyl or phenyl optionally substituted with $R_{14}$;

when $R_8$ is $C_3$-$C_6$ cycloalkyl or $C_4$-$C_7$ cycloalkylalkyl, it may optionally be substituted by $C_1$-$C_4$ alkyl, 1 to 3 atoms of Cl or F or 1 Br; when $R_8$ is $C_1$-$C_{10}$ alkyl, $C_2$-$C_{10}$ alkenyl or $C_2$-$C_{10}$ alkynyl, it may optionally be substituted by one or more halogens and/or by $(R_{15})_r$ provided that when r is 2, the values of $R_{15}$ may be identical or different;

$R_8'$ is $C_1$-$C_{10}$ alkyl, $C_3$-$C_{10}$ alkoxyalkoxyalkyl, $C_3$-$C_{10}$ alkenyl, $C_3$-$C_{10}$ epoxyalkyl, $C_3$-$C_{10}$ alkynyl, $C_3$-$C_6$ cycloalkyl, $C_4$-$C_7$ cycloalkylalkyl or phenyl optionally substituted with $R_{14}$; when $R_8'$ is $C_3$-$C_6$ cycloalkyl or $C_4$-$C_7$ cycloalkylalkyl, it may optionally be substituted by $C_1$-$C_4$ alkyl, 1 to 3 atoms of Cl or F or 1 Br; when $R_8'$ is $C_1$-$C_{10}$ alkyl, $C_3$-$C_{10}$ alkenyl or $C_3$-$C_{10}$ alkynyl, it may optionally be substituted by one or more halogens and/or by $(R_{15})_r$ provided that when r is 2, the values of $R_{15}$ may be identical or different;

r is 0, 1 or 2:

$R_9$ is H or $C_1$-$C_4$ alkyl;

$R_{10}$ is H, $C_1$-$C_{10}$ alkyl, $C_1$-$C_{10}$ haloalkyl, $C_3$-$C_{10}$ alkenyl, $C_3$-$C_{10}$ alkynyl, $C_3$-$C_6$ cycloalkyl or phenyl substituted with $R_{14}$;

$R_{10}'$ is $C_1$-$C_{10}$ alkyl, $C_1$-$C_{10}$ haloalkyl, $C_3$-$C_{10}$ alkenyl, $C_3$-$C_{10}$ alkynyl, $C_3$-$C_6$ cycloalkyl or phenyl substituted with $R_{14}$;

$R_{11}$ and $R_{12}$ are independently $C_1$-$C_4$ alkyl, $C_1$-$C_4$ alkoxy or $C_1$-$C_4$ alkylthio;

$R_{13}$ is $C_1$-$C_{10}$ alkyl, benzyl or phenyl optionally substituted with $R_{14}$;

$R_{14}$ is H, F, Cl, Br, $CH_3$, $OCH_3$, $NO_2$, CN, $SCH_3$, $SO_2CH_3$ or $CF_3$;

$R_{15}$ is $OR_{10}$, $OC(O)R_{10}$, $OC(O)NR_9R_{10}$, $OSO_2R_{10}'$, $OP(O)R_{11}R_{12}$, $OSi(CH_3)_2R_{13}$, $SR_{10}$, $SOR_{10}'$, $SO_2R_{10}'$, SCN, CN, $SP(O)R_{11}R_{12}$, $SP(S)R_{11}R_{12}$, $P(O)R_{11}R_{12}$, $P(S)R_{11}R_{12}$, $NR_9R_{10}$, $N+R_9R_{10}R_{13}$, $NR_9C(O)R_{10}$, $NR_9C(O)OR_{10}'$, $NR_9C(O)NR_9R_{10}$, $NR_9SO_2R_{10}'$, $NR_9P(O)R_{11}R_{12}$, $NR_9P(S)R_{11}R_{12}$, $NO_2$, $C(O)R_{10}$, $C(O)OR_{10}$, $C(O)NR_9R_{10}$, $C(R_{10})=NOR_{12}$, naphthyl, L, phenyl optionally substituted with $R_{14}$ and/or $R_{16}$,

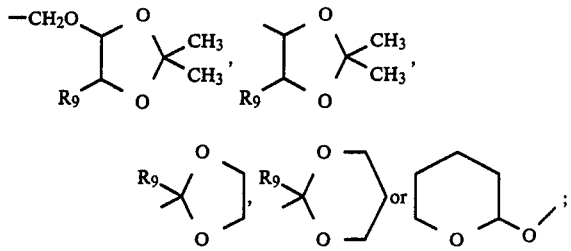

$R_{16}$ is H, F, Cl or Br;

L is a 5- or 6-membered aromatic heterocyclic, a 5- or 6-membered dihydroaromatic heterocycle or a 5- or 6-membered tetrahydroaromatic heterocycle which contains 1–4 heteroatoms selected from 0–1 oxygen atoms, 0–1 sulfur atoms and/or 0–4 nitrogen atoms and these heterocycles may optionally be substituted by 1–4 $CH_3$, 1–2 $OCH_3$, $SCH_3$, Cl, $N(CH_3)_2$ or CN groups or L is a 5- or 6-membered lactone, lactam or cycloalkanone which may optionally be substituted by 1–4 $CH_3$ groups;

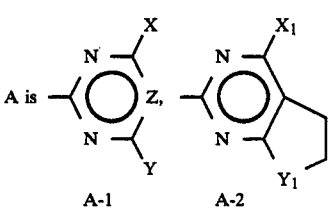

A-1    A-2

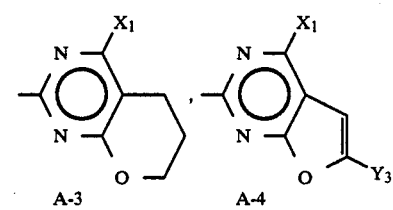

A-3    A-4

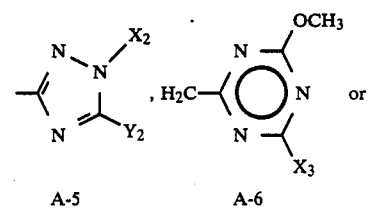

A-5    A-6

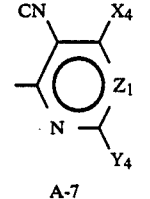

A-7

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylsulfinylalkyl, $C_1$-$C_4$ haloalkyl, C₂–C₅ alkylsulfonylalkyl, C₃–C₅ cycloalkyl, C₂–C₄ alkynyl, C₂–C₅ alkylthioalkyl,

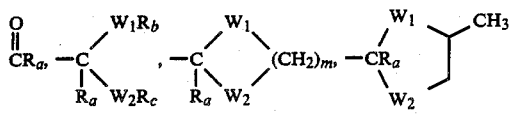

or N(OCH₃)CH₃;
W₁ and W₂ are independently O or S;
m is 2 or 3;
R$_a$ is H or CH₃;
R$_b$ is C₁–C₂ alkyl;
R$_c$ is C₁–C₂ alkyl;
Z is CH, N, CCH₃, CC₂H₅, CCl or CBr;
Y₁ is O or CH₂;
X₁ is CH₃, OCH₃, OC₂H₅ or OCF₂H;
X₂ is CH₃, C₂H₅ or CH₂CF₃;
Y₂ is OCH₃, OC₂H₅, SCH₃, SC₂H₅, OCF₂H, SCF₂H, CH₃ or CH₂CH₃;
X₃ is CH₃ or OCH₃;
Y₃ is H or CH₃;
X₄ is CH₃, OCH₃, OC₂H₅, CH₂OCH₃ or Cl;
Y₄ is CH₃, OCH₃, OC₂H₅ or Cl; and
Z₁ is CH or N;
and their agriculturally suitable salts; provided that
(a) when W is S, then R is H, A is A-1, Z is CH or N, and Y is CH₃, OCH₃, OC₂H₅, CH₂OCH₃, C₂H₅, CF₃, SCH₃, OCH₂CH=CH₂, OCH₂C≡CH, OCH₂CH₂OCH₃, CH(OCH₃)₂ or

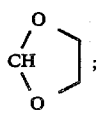

(b) when X is Cl, Br, F or I, then Z is CH and Y is OCH₃, OC₂H₅, NH₂, NHCH₃, N(CH₃)₂ or OCF₂H;
(c) when X or Y is C₁ haloalkoxy, then Z is CH;
(d) in compounds of Formula Ia, either R₁ or R₂ must be H;
(e) when the total number of carbon atoms in X and Y is greater than 4, then the total number of carbon atoms in R₁, R₂, R₃ and the bridging group E is less than or equal to 10;
(f) X₄ and Y₄ are not simultaneously Cl;
(g) the total number of carbon atoms in R₆ is less than or equal to 12; and
(h) when R₁₅ and the bridging nitrogen of a cyclic sulfonamide are attached to the same carbon then R₁₅ is other than OH, SH, OC(O)R₁₀, OC(O)NR₉R₁₀, OSO₂R₁₀', OP(O)R₁₁R₁₂, OSi(CH₃)₂R₁₃, SP(O)R₁₁R₁₂, SP(S)R₁₁R₁₂, NR₉R₁₀ or N+R₉R₁₀R₁₃.

In the above definitions, the term "alkyl", used either alone or in compound words such as "alkylthio" or "haloalkyl", denotes straight chain or branched alkyl, e.g. methyl, ethyl, n-propyl, 2-propyl or the different butyl, pentyl, hexyl, heptyl, octyl, nonyl or decyl isomers.

Alkoxy denotes methoxy, ethoxy, n-propyloxy, isopropyloxy and the different butyl, pentyl, hexyl, heptyl, octyl or nonyl isomers.

Alkenyl denotes straight chain or branched alkenes, e.g. vinyl, 1-propenyl, 2-propenyl, isopropenyl and the different butenyl, pentenyl, hexenyl, heptenyl, octenyl, nonenyl or decenyl isomers.

Alkynyl denotes straight chain or branch alkynes, e.g., ethynyl, 1-propynyl, 2-propynyl and the different butynyl, pentynyl, hexynyl, heptynyl, octynyl, nonynyl and decynyl isomers.

Alkylcarbonyl denotes, e.g., acetyl and propionyl.

Alkoxycarbonyl denotes, e.g., methoxycarbonyl, ethoxycarbonyl, propoxycarbonyl and isopropoxycarbonyl.

Alkylsulfonyl denotes methylsulfonyl, ethylsulfonyl and the different propylsulfonyl isomers.

Alkylthio, alkylsulfinyl, alkylamino, alkylsulfamoyl, etc. are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine.

The total number of carbon atoms in a substituent group is indicated by the $C_i$–$C_j$ prefix where i and j are numbers from 1 to 10. For example, C₂–C₅ alkylsulfonylalkyl would designate CH₂SO₂CH₃ through (CH₂)₄SO₂CH₃ or CH₂SO₂C₄H₉, C₂ alkoxyalkoxy would designate OCH₂OCH₃, C₂ cyanoalkyl would designate CH₂CN and C₃ cyanoalkyl would designate CH₂CH₂CN and CH(CN)CH₃.

It would be recognized by one skilled in the art that when R₁₅ is OH or SH, that these substituents cannot be bonded to the same carbon as another heteroatom or to an olefinic or acetylenic carbon atom.

Preferred for reasons of greater ease of synthesis and/or greater herbicidal efficacy are:
1. Compounds of Formula I where J is Ia.
2. Compounds of Preferred 1 where J is

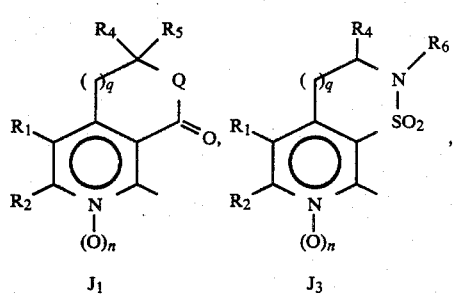

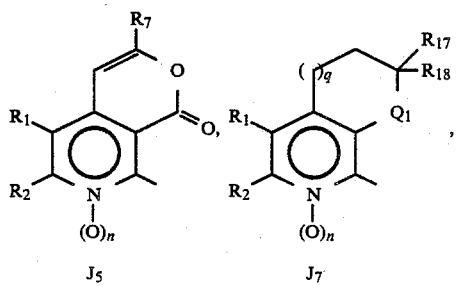

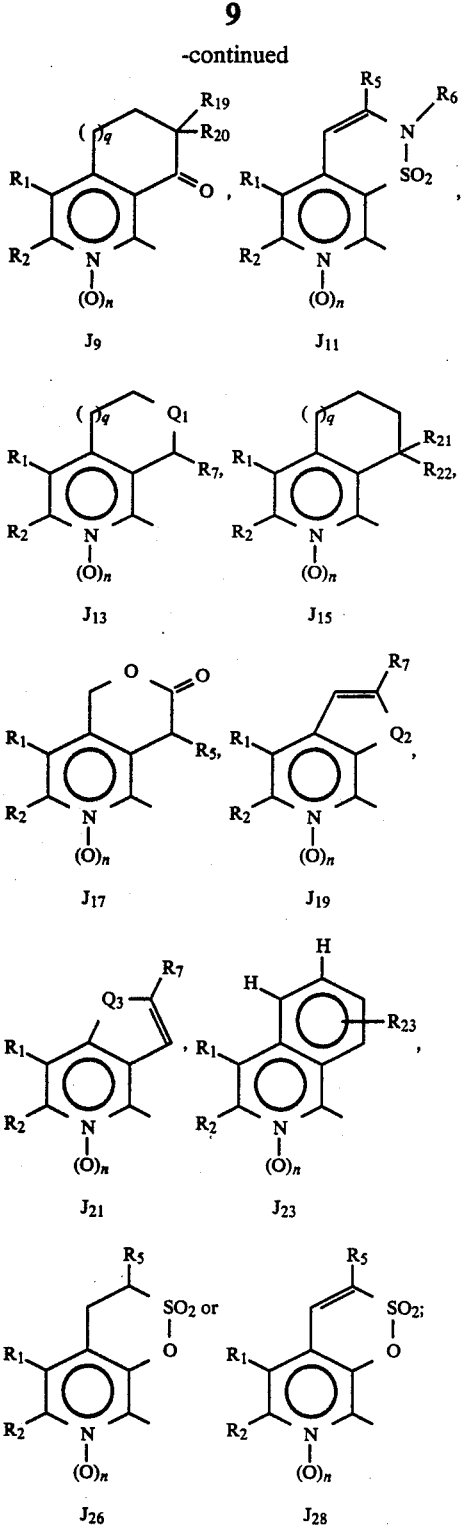

q is 0 or 1;
Q is O, S, or NR$_4$;
Q$_1$ is O, S, SO, SO$_2$, NH or NCH$_3$;
Q$_2$ is O, S, NH, NCH$_3$, CH$_2$ or CHCH$_3$;
Q$_3$ is O, S, NH, NCH$_3$ or CH$_2$;
R$_4$ is H or C$_1$-C$_4$ alkyl;
R$_5$ is H or CH$_3$;
R$_7$ is H or C$_1$-C$_3$ alkyl;
R$_{17}$ is H or C$_1$-C$_4$ alkyl;
R$_{18}$ is H or CH$_3$;

R$_{19}$ is H, F, Cl or C$_1$-C$_4$ alkyl;
R$_{20}$ is H, F, Cl or CH$_3$;
R$_{21}$ is H, C$_1$-C$_3$ alkyl, C$_1$-C$_3$ alkoxy, F or Cl;
R$_{22}$ is H, CH$_3$, C$_1$-C$_3$ alkoxy, F, Cl or OH; or
R$_{21}$ and R$_{22}$ can be taken together to form —OCH$_2$CH$_2$O— or —OCH$_2$CH$_2$CH$_2$O—;
R$_{23}$ is H, C$_1$-C$_3$ alkyl, C$_1$-C$_3$ alkoxy, Cl, Br or F; provided that
(a) the total number of carbon atoms in R$_{19}$ and R$_{20}$ is less than or equal to 4;
(b) the total number of carbon atoms in R$_4$ and R$_5$ is less than or equal to 4;
(c) when R$_{21}$ is C$_1$-C$_3$ alkoxy, then R$_{22}$ is H, CH$_3$ or C$_1$-C$_3$ alkoxy; and
(d) when R$_{22}$ is OH, then R$_{21}$ is H or C$_1$-C$_3$ alkyl, and when R$_{22}$ is C$_1$-C$_3$ alkoxy, then R$_{21}$ is H, C$_1$-C$_3$ alkyl or C$_1$-C$_3$ alkoxy.

3. Compounds of Preferred 2 where
n is 0;
W is O;
R is H;
X is CH$_3$, OCH$_3$, OC$_2$H$_5$, Cl, Br, F, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, CH$_2$SCH$_2$CH$_3$,

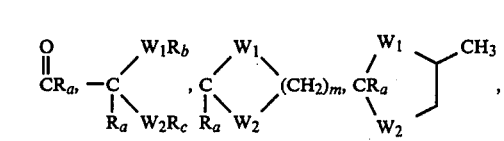

OCF$_2$H, SCF$_2$H, CH=CH or C≡CCH$_3$; and
Z is CH or N.

4. Compounds of Preferred 3 where
R$_2$ is H, CH$_3$, OCH$_3$, Cl or Br;
R$_6$ is H, R$_8'$, C(O)R$_8$ or CO$_2$R$_8'$;
R$_8$ and R$_8'$ are C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, C$_3$-C$_6$ epoxyalkyl or C$_1$-C$_4$ alkyl substituted with C$_1$-C$_2$ alkoxy, C$_1$-C$_2$ alkylthio, C$_1$-C$_2$ alkylsulfinyl, C$_1$-C$_2$ alkylsulfonyl, CO$_2$(C$_1$-C$_2$ alkyl), C(O)C$_1$-C$_2$ alkyl, CN or OH;
R$_{19}$ is H or C$_1$-C$_3$ alkyl;
R$_{20}$ is H or CH$_3$;
R$_{21}$ is H, C$_1$-C$_3$ alkyl or C$_1$-C$_2$ alkoxy;
R$_{22}$ is H, CH$_3$, C$_1$-C$_2$ alkoxy or OH; or
R$_{21}$ and R$_{22}$ may be taken together to form —OCH$_2$CH$_2$O— or —OCH$_2$CH$_2$CH$_2$O—; and
R$_{23}$ is H, CH$_3$, Cl, Br or OCH$_3$.

5. Compounds of Preferred 4 where R$_8$ and R$_8'$ are C$_1$-C$_6$ alkyl, C$_1$-C$_4$ haloalkyl, C$_3$-C$_4$ alkenyl, C$_3$-C$_4$ haloalkenyl, C$_3$-C$_4$ alkynyl, CO$_2$(C$_1$-C$_2$ alkyl), C(O)C$_1$-C$_2$ alkyl or C$_1$-C$_3$ alkyl substituted with C$_1$-C$_2$ alkoxy, C$_1$-C$_2$ alkylthio, C$_1$-C$_2$ alkylsulfonyl or CN.

6. Compounds of Preferred 5 where
A is A-1;
X is CH$_3$, OCH$_3$, OC$_2$H$_5$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

7. Compounds of Preferred 6 where J is J$_1$.
8. Compounds of Preferred 6 where J is J$_3$.
9. Compounds of Preferred 6 where J is J$_5$.
10. Compounds of Preferred 6 where J is J$_7$.

11. Compounds of Preferred 6 where J is J$_9$.
12. Compounds of Preferred 6 where J is J$_{11}$.
13. Compounds of Preferred 6 where J is J$_{13}$.
14. Compounds of Preferred 6 where J is J$_{15}$.
15. Compounds of Preferred 6 where J is J$_{17}$.
16. Compounds of Preferred 6 where J is J$_{19}$.
17. Compounds of Preferred 6 where J is J$_{21}$.
18. Compounds of Preferred 6 where J is J$_{23}$.
19. Compounds of Preferred 6 where J is J$_{26}$.
20. Compounds of Preferred 6 where J is J$_{28}$.
21. Compounds of Formula I where J is Ib.
22. Compounds of Preferred 21 where J is

[Structures: J$_2$, J$_4$, J$_6$, J$_8$, J$_{10}$, J$_{12}$, J$_{14}$, J$_{16}$, J$_{18}$, J$_{20}$, J$_{22}$, J$_{24}$, J$_{27}$, J$_{29}$]

q is 0 or 1;
Q is O, S, or NR$_4$;
Q$_1$ is O, S, SO, SO$_2$, NH or NCH$_3$;
Q$_2$ is O, S, NH, NCH$_3$, CH$_2$ or CHCH$_3$;
Q$_3$ is O, S, NH, NCH$_3$ or CH$_2$;
R$_4$ is H or C$_1$–C$_4$ alkyl;
R$_5$ is H or CH$_3$;
R$_7$ is H or C$_1$–C$_3$ alkyl;
R$_{17}$ is H or C$_1$–C$_4$ alkyl;
R$_{18}$ is H or CH$_3$;
R$_{19}$ is H, F, Cl or C$_1$–C$_4$ alkyl;
R$_{20}$ is H, F, Cl or CH$_3$;
R$_{21}$ is H, C$_1$–C$_3$ alkyl, C$_1$–C$_3$ alkoxy, F or Cl;
R$_{22}$ is H, CH$_3$, C$_1$–C$_3$ alkoxy, F, Cl or OH; or
R$_{21}$ and R$_{22}$ can be taken together to form —OCH$_2$CH$_2$O— or —OCH$_2$CH$_2$CH$_2$O—;
R$_{23}$ is H, C$_1$–C$_3$ alkyl, C$_1$–C$_3$ alkoxy, Cl, Br or F;
provided that
(a) the total number of carbon atoms in R$_{19}$ and R$_{20}$ is less than or equal to 4;
(b) the total number of carbon atoms in R$_4$ and R$_5$ is less than or equal to 4;
(c) when R$_{21}$ is C$_1$–C$_3$ alkoxy, then R$_{22}$ is H, CH$_3$ or C$_1$–C$_3$ alkoxy; and
(d) when R$_{22}$ is OH, then R$_{21}$ is H or C$_1$–C$_3$ alkyl, and when R$_{22}$ is C$_1$–C$_3$ alkoxy, then R$_{21}$ is H, C$_1$–C$_3$ alkyl or C$_1$–C$_3$ alkoxy.

23. Compounds of Preferred 22 where
n is 0;
W is O;
R is H;
X is CH$_3$, OCH$_3$, OC$_2$H$_5$, Cl, Br, F, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, CH$_2$SCH$_2$CH$_3$,

[Structures showing substituent groups]

OCF$_2$H, SCF$_2$H, CH=CH or C≡CCH$_3$; and

Z is CH or N.
24. Compounds of Preferred 23 where
R$_2$ is H, CH$_3$, OCH$_3$, Cl or Br;
R$_3$ is CH$_3$, CH$_2$CH$_3$, F, Cl, Br, OCH$_3$, OCH$_2$CH$_3$, SCH$_3$ SCH$_2$CH$_3$, SO$_2$CH$_3$, SO$_2$CH$_2$CH$_3$, SO$_2$N(CH$_3$)$_2$, C(O)NHCH$_3$ or C(O)N(CH$_3$)$_2$;
R$_6$ is H, R$_8$', C(O)R$_8$ or CO$_2$R$_8$';
R$_8$ and R$_8$' are C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, C$_3$-C$_6$ epoxyalkyl or C$_1$-C$_4$ alkyl substituted with C$_1$-C$_2$ alkoxy, C$_1$-C$_2$ alkylthio, C$_1$-C$_2$ alkylsulfinyl, C$_1$-C$_2$ alkylsulfonyl, CO$_2$(C$_1$-C$_2$ alkyl), C(O)C$_1$-C$_2$ alkyl, CN or OH;
R$_{19}$ is H or C$_1$-C$_3$ alkyl;
R$_{20}$ is H or CH$_3$;
R$_{21}$ is H, C$_1$-C$_3$ alkyl or C$_1$-C$_2$ alkoxy;
R$_{22}$ is H, CH$_3$, C$_1$-C$_2$ alkoxy or OH; or
R$_{21}$ and R$_{22}$ may be taken together to form —OCH$_2$CH$_2$O— or —OCH$_2$CH$_2$CH$_2$O—; and
R$_{23}$ is H, CH$_3$, Cl, Br or OCH$_3$.
25. Compounds of Preferred 24 where
R$_8$ and R$_8$' are C$_1$-C$_6$ alkyl, C$_1$-C$_4$ haloalkyl, C$_3$-C$_4$ alkenyl, C$_3$-C$_4$ haloalkenyl, C$_3$-C$_4$ alkynyl, CO$_2$(C$_1$-C$_2$ alkyl), C(O)C$_1$-C$_2$ alkyl or C$_1$-C$_3$ alkyl substituted with C$_1$-C$_2$ alkoxy, C$_1$-C$_2$ alkylthio, C$_1$-C$_2$ alkylsulfonyl or CN.
26. Compounds of Preferred 25 where
A is A-1;
X is CH$_3$, OCH$_3$, OC$_2$H$_5$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.
27. Compounds of Preferred 26 where J is J$_2$.
28. Compounds of Preferred 26 where J is J$_4$.
29. Compounds of Preferred 26 where J is J$_6$.
30. Compounds of Preferred 26 where J is J$_8$.
31. Compounds of Preferred 26 where J is J$_{10}$.
32. Compounds of Preferred 26 where J is J$_{12}$.
33. Compounds of Preferred 26 where J is J$_{14}$.
34. Compounds of Preferred 26 where J is J$_{16}$.
35. Compounds of Preferred 26 where J is J$_{18}$.
36. Compounds of Preferred 26 where J is J$_{20}$.
37. Compounds of Preferred 26 where J is J$_{22}$.
38. Compounds of Preferred 26 where J is J$_{24}$.
39. Compounds of Preferred 26 where J is J$_{27}$.
40. Compounds of Preferred 26 where J is J$_{29}$.
41. Compounds of Formula I where J is Ic.
42. Compounds of Preferred 41 where J is

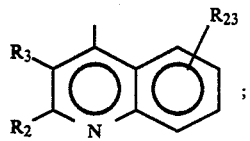 J$_{25}$ and
R$_{23}$ is H, C$_1$-C$_3$ alkyl, C$_1$-C$_3$ alkoxy, Cl, Br or F.
43. Compounds of Preferred 42 where
W is O;
R is H;
X is CH$_3$, OCH$_3$, OC$_2$H$_5$, Cl, Br, F, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, CH$_2$SCH$_2$CH$_3$,

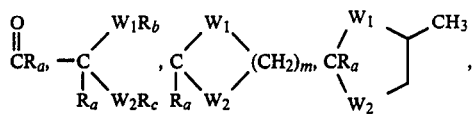

OCF$_2$H, SCF$_2$H, CH=CH or C≡CCH$_3$; and
Z is CH or N.
44. Compounds of Preferred 43 where R$_2$ is H, CH$_3$, OCH$_3$, Cl or Br; R$_3$ is H, CH$_3$, CH$_2$CH$_3$, F, Cl, Br, OCH$_3$, OCH$_2$CH$_3$, SCH$_3$, SCH$_2$CH$_3$, SO$_2$CH$_3$, SO$_2$CH$_2$CH$_3$, SO$_2$N(CH$_3$)$_2$, C(O)NHCH$_3$ or C(O)N(CH$_3$)$_2$; and R$_{23}$ is H, CH$_3$, Cl, Br or OCH$_3$.
45. Compounds of Preferred 44 where
A is A-1;
X is CH$_3$, OCH$_3$, OC$_2$H$_5$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

Specifically preferred for reasons of their highest herbicidal activity, greatest plant growth regulant activity and/or most favorable ease of synthesis are;
N-[(4,6-dimethoxypyrimidin-2-yl)aminocarbonyl]-thieno[2,3-c]pyridine-7-sulfonamide, m.p. 183°–186° C.(d); and
N-[(4-methoxy-6-methylpyrimidin-2-yl)aminocarbonyl]thieno2,3-c]pyridine-7-sulfonamide, m.p. 182°–184° C.(d).

DETAILED DESCRIPTION OF THE INVENTION

Synthesis

The preparation of N-oxides, such as Ia (n=1) and Ib (n=1), from the corresponding pyridines, such as Ia (n=0) and Ib (n=0) can be carried out by any of several known methods as described in *Chemistry of the Heterocyclic N-Oxides*, Katritzky and Lagowski, Academic Press, New York, 1971.

The compounds of Formula I can be prepared by one or more of the methods described below in Equations 1, 2, 3 and 4.

As shown in Equation 1, compounds of Formula I, where J is other than J$_9$ and J$_{10}$, can be prepared by reacting a sulfonylisocyanate (W=O) or a sulfonylisothiocyanate (W=S) of Formula II with an appropriate heterocyclic amine of Formula III, wherein R and A are as previously defined.

Equation 1

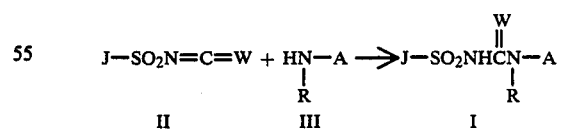

The reaction is carried out at 25° to 100° C. in an inert, aprotic solvent such as methylene chloride or xylene for 0.5 to 24 hours as taught in U.S. Pat. No. 4,127,405.

Compounds of Formula I, where W is S and R is H, (Id) can be prepared by reacting the appropriate sulfonamide of Formula IV with a heterocyclic isothiocyanate of Formula V, as shown in Equation 2.

Equation 2

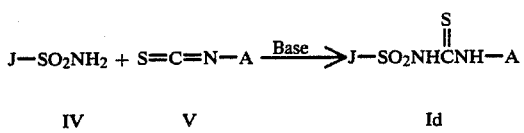

IV      V      Id

The reaction is carried out at 25° to 80° C. in an inert, aprotic solvent such as acetone or acetonitrile in the presence of a base such as potassium carbonate for 0.5 to 24 hours. The required heterocyclic isothiocyanates V are prepared from the corresponding amines III as taught in EPO Publication No. 35,893.

Compounds of Formula I, where W is O (Ie) and J is other than $J_1$, $J_2$, $J_5$, $J_6$, $J_{17}$, $J_{18}$, $J_{26}$, $J_{27}$, $J_{28}$, and $J_{29}$ can be prepared by reacting the sulfonamides of Formula IV with an appropriate methylcarbamate of Formula VI in the presence of an equimolar amount of trimethylaluminum, as shown in Equation 3.

Equation 3

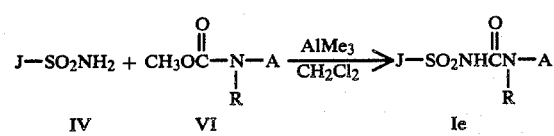

IV      VI      Ie

The reaction is carried out at 25° to 40° in a solvent such as methylene chloride for 10 to 96 hours under an inert atmosphere as taught in EPO Publication No. 84,244 (7/27/83). The required carbamates VI are prepared by reacting the corresponding amines III with dimethylcarbonate or methyl chloroformate in the presence of a strong base.

Alternatively, compounds of Formula Ie can be prepared by reacting a sulfonylcarbamate of Formula VII with an appropriate amine of Formula III, as shown in Equation 4.

Equation 4

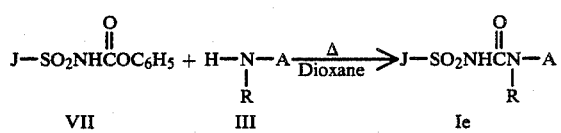

VII      III      Ie

The reaction is carried out at 50° to 100° C. in a solvent such as dioxane for 0.5 to 24 hours as taught in U.S. Pat. No. 4,443,243. The required carbamates VII are prepared by reacting the corresponding sulfonamides IV with diphenylcarbonate in the presence of a strong base.

The intermediate sulfonylisocyanates (W=O) and sulfonylisothiocyanates (W=S) of Formula II from Equation 1 can be prepared as shown in Equations 5, 6 and 7.

As shown in Equation 5, sulfonylisocyanates of Formula IIa, where J is other than $J_9$ and $J_{10}$, can be prepared by the reaction of sulfonamides of Formula IV with phosgene in the presence of n-butylisocyanate and a tertiary amine catalyst, at reflux in a solvent such as xylene by the method of U.S. Pat. No. 4,238,621.

Equation 5

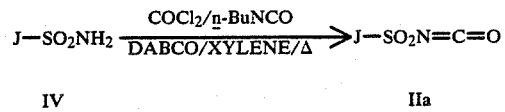

IV      IIa

The sulfonylisocyanates can also be prepared from the sulfonamides by a two step procedure involving: (a) reacting the sulfonamides with n-butylisocyanate in the presence of a base such as $K_2CO_3$ at reflux in an inert solvent such as 2-butanone forming a n-butylsulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p. 223-241, Academic Press, New York and London, W. Foerst Ed.

Alternatively, as shown in Equation 6, the sulfonylisocyanates of Formula IIa can be prepared by reacting the corresponding sulfonyl chlorides VIII with cyanic acid salts.

Equation 6

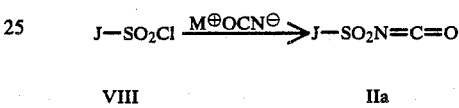

VIII      IIa

The reaction is carried out at 25° to 100° C. in an inert aprotic solvent such as acetonitrile for 0.5 to 24 hours in the presence of phosphorus pentoxide and an alkali metal salt such as lithium iodide according to the teachings of Japanese Pat. No. 76/26,816 (*Chem. Abst.*, 85: 77892e (1976)).

The sulfonylisothiocyanates of Formula IIb, where J is other than $J_9$ and $J_{10}$, can be prepared as shown in Equation 7, by contacting the sulfonamides of Formula IV with carbon disulfide in the presence of two equivalents of a strong base. The resulting salt is then reacted with phosgene according to the teachings of K. Hartke, *Arch. Pharm.*, 299, 174 (1966).

Equation 7

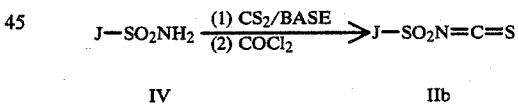

IV      IIb

The sulfonamides of Formula IV of Equations 2, 3, 5 and 7 are important intermediates for the preparation of the compounds of this invention. The syntheses of the required sulfonamide intermediates are described in Equations 8, 9 and 10.

As shown in Equation 8, sulfonamides of Formula IV can be prepared from the corresponding sulfonyl chlorides of Formula VIII by treatment with either anhydrous or aqueous ammonia.

Equation 8

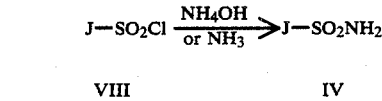

VIII      IV

The preparation of sulfonamides from sulfonyl chlorides is widely reported in the literature; for reviews see: F. Hawking and J. S. Lawrence, "The Sulfonamides," H. K. Lewis and Co., London, 1950 and E. H. Northey, "The Sulfonamides and Allied Compounds," Reinhold Publishing Corp. New York, 1948.

The sulfonamides of Formula IV can also be prepared from the corresponding thiol IX by the three step sequence shown in Equation 9.

Equation 9

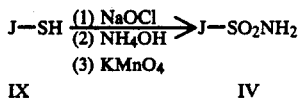

The first step involves chlorination of a mercaptan such as IX to give a sulfenyl chloride, the chlorine of which is subsequently displaced in a second step with a suitable ammonia equivalent such as aqueous ammonium hydroxide to provide a sulfenamide. In a final step, the intermediate sulfenamide can be oxidized to a sulfonamide, such as IV, using an oxidizing agent such as potassium permanganate according to the methods taught by R. Lejeune, *J. Pharm. Belg.*, 39, 217 (1984).

The unsaturated sulfonamides of Formula IVa can also be prepared from the corresponding saturated sulfonamides of Formula IVb by the two step procedure shown in Equation 10, wherein G is $-SO_2NR_6-$, $-CO_2-$, $-Q_2-$ or $-Q_3-$, $R_{24}$ is $R_5$ or $R_7$, and $R_{25}$ is H or t-butyl.

Equation 10

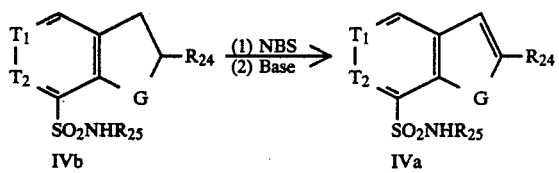

where
$T_1$ is CH and $T_2$ is N or
$T_1$ is N and $T_2$ is CH.

The first step involves benzylic bromination with N-bromosuccinimide to give a monobromide, which is subsequently dehydrobrominated in a second step by reaction with a suitable base such as triethylamine or potassium-t-butoxide in an inert solvent such as THF. This method has been used to prepare isocoumarins from 3,4-dihydroisocoumarins; see R. Barry, *Chem. Rev.*, 64, 229 (1964).

The sulfonyl chlorides of Formula VIII of Equations 6 and 8 can be prepared from the corresponding amines X by the method shown in Equation 11.

Equation 11

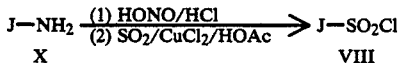

The reaction involves diazotization of the amine X with sodium nitrite in HCl, followed by reaction of the diazonium salt with sulfur dioxide and cupric chloride in acetic acid in analogy to the teachings of Yale and Sowinski, *J. Org. Chem.*, 25, 1824 (1960).

Alternatively, sulfonyl chlorides of Formula VIII can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°–40° C. for 1 to 24 hours.

Some of the sulfonyl chlorides of Formula VIII may be prepared by direct chlorosulfonation, depending on the substitution pattern on the ring and the nature of the substituent as will be known to one skilled in the art.

The sulfonyl chlorides of Formula VIII can also be prepared from the chloro compounds XI by the two step sequence shown in Equation 12.

Equation 12

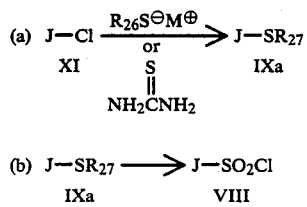

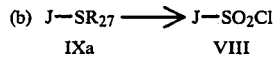

$R_{26} = C_1$–$C_4$ alkyl, $CH_2C_6H_5$, or H;
$R_{27} = C_1$–$C_4$ alkyl, $CH_2C_6H_5$, H, or $C(=NH)NH_2 \cdot HCl$;
M = K or Na.

The first step involves nucleophilic displacement of the chlorine atom with an alkyl or benzyl mercaptan or with thiourea to give an intermediate sulfide or thiouronium salt. The reaction can be carried out at 25° to 80° C. in a polar solvent such as DMF for 0.5 to 2 hours. The sulfide, thiol or thiouronium salt is then oxidatively chlorinated to the desired sulfonyl chloride VIII in the presence of water at $-30°$ to 0° in an aliphatic carboxylic acid solvent such as propionic acid or a concentrated acid such as hydrochloric acid or an inert organic solvent such as dichloromethane for 1 to 24 hours. The preparation of pyridine sulfonyl chlorides, such as VIII, from mercaptans is similar to that taught by Y. Morisawa, et al., *J. Med. Chem.*, 1980, 23, 1376–1380.

Many of the mercaptans of Formula IX in Equation 9 can be prepared from the pyridones of Formula XII as shown in Equation 13.

Equation 13

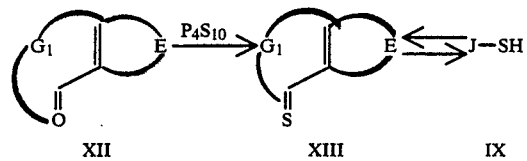

where
$G_1$ is $-NH-CH=CH-$ or $-CH=CH-NH-$; and
E is as previously defined.

The thiones of Formula XIII can be prepared from the corresponding pyridones XII using base-solubilized phosphorous pentasulfide in solvents such as acetonitrile, pyridine, or dichloromethane as taught by B. Dash, et al., *Heterocycles*, 19, 2093 (1982) and F. Eloy and A. Deryckere, *Bull. Soc. Chim. Belges*, 79, 407 (1970).

Many other mercaptans can be prepared via the Newman-Karnes rearrangement of O-aryl thiocarbamates and hydrolysis of the resulting S-aryl thiocarbamates, such as XV, a representative example of which is shown in Equation 14.

The S-aryl thiocarbamates, such as XV, can also be converted directly to sulfonyl chlorides VIII via oxidative chlorination as described in Equation 12b.

Equation 14

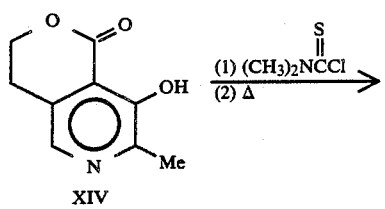

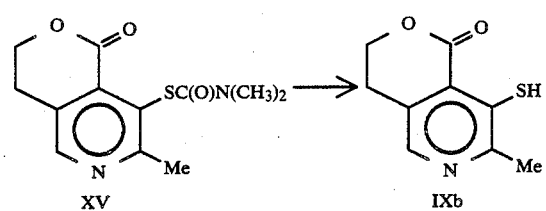

The synthesis of lactone XIV is described by W. Korytnyk and H. Ahrens, *J. Med. Chem.*, 1971, 14, 947–952. The preparation of O-aryl thiocarbamates, their thermal rearrangement and hydrolysis is taught by M. S. Newman and H. A. Karnes, *J. Org. Chem.*, 31, 3980 (1966), references cited therein and B. Blank, et al., *J. Med. Chem.*, 17, 1065 (1974). The preparation of sulfonyl chlorides via the oxidative chlorination of S-aryl thiocarbamates is described by A. Wagenaar and T. Engberts, *Recl. Trav. Chim.* 101, 91 (1982).

Chlorides of Formula XI in Equation 12 can be obtained from pyridones XII as shown below.

Equation 15

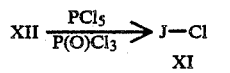

The pyridones XII can be converted to chlorides XI in the presence of phosphorous oxychloride and phosphorous pentachloride. This procedure has been used to prepare 4-chloro-1,3-dihydro-6-methyl-3-oxofuro[3,4-c]pyridine; see: W. F. Bruce and H. W. Coover, *J. Am. Chem. Soc.*, 66, 2092 (1944). For additional examples, see: Rivalle, et al., *J. Heterocyclic Chem.*, 13, 89–92 (1976); Bisagni, et al., ibid., 12, 461–465 (1975); Eloy and Deryckere, *Bull. Soc. Chim. Belges*, 79, 407–414 (1970) and Bisagni, *Tetrahedron*, 26, 2087 (1970).

Many other chlorides XIa can be prepared by direct chlorination of the corresponding pyridines XVI as shown in Equation 16.

Equation 16

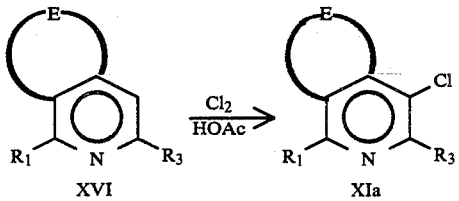

where $R_1$, $R_3$ and E are as previously defined; and

E is not readily chlorinated.

The pyridines of Formula XVI are chlorinated with an appropriate chlorine source, such as sulfuryl chloride or chlorine in an aliphatic carboxylic acid solvent such as acetic acid or in an inert organic solvent such as dichloromethane for 1 to 24 hours to provide chlorides such as XIa.

The preparation of annelated pyridines such as XI, IX and X can also be carried out by any of several methods described in *Pyridine and its Derivatives*, G. Newkome, ed., Wiley and Sons, New York, 1984, pp. 253–445, or modifications thereof.

Many pyridones of Formula XIIb can be prepared by the condensation of a 1,3-dicarbonyl compound such as XVII and 2-cyanoacetamide as shown in Equation 17.

Equation 17

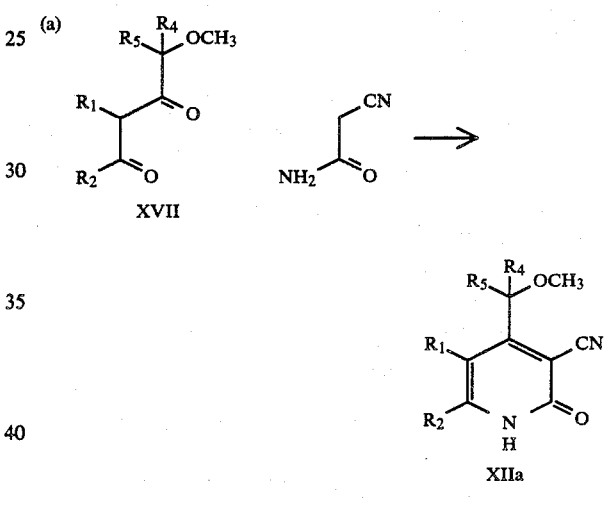

The substituted 1,3-dicarbonyl compounds, prepared by methods known to one skilled in the art, are combined with 2-cyanoacetamide in a solvent such as ethanol with an appropriate base catalyst to produce pyridones such as XIIa. Acid hydrolysis and cyclization gives the desired lactone pyridone XIIb. This method is taught by S. A. Harris, et al., *J. Am. Chem. Soc.*, 61, 1242 (1939).

Several pyridones of Formula XIIc or chlorides of Formula XIb can be obtained from pyridines such as XVIII as shown in Equation 18.

Equation 18

(a) 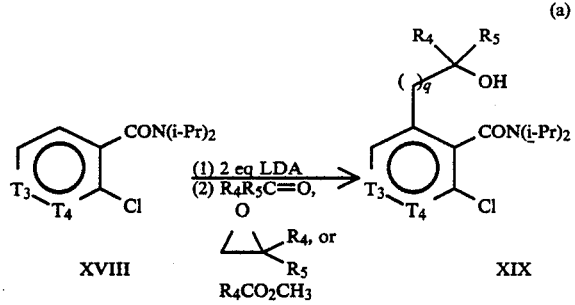

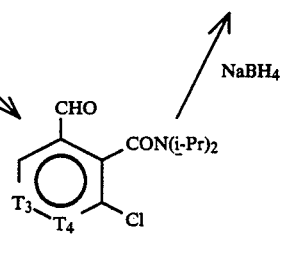

where T₃-T₄ is N—CH or CH—N;

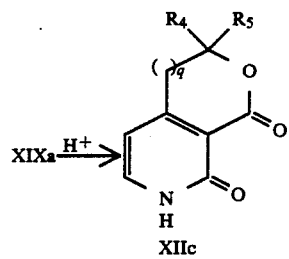

where T₃-T₄ is CH—N;

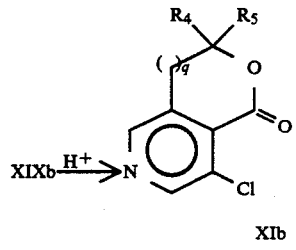

where T₃-T₄ is N—CH;

$R_4$, $R_5$ and q are as previously defined.

An appropriately substituted diisopropylamide XVIII is combined with two equivalents of lithium diisopropylamide to give an anion according to the teachings of J. Epsztajn, *Tet. Lett.*, 24, 4735-4738 (1983). The anion can then be trapped with a ketone, ester or epoxide at −78° to 25° C. to produce, upon workup, the alcohol XIX. The anion can also be trapped with N,N-dimethylformamide to give aldehyde XX, which on reduction also provides alcohol XIX ($q=0$, $R_4=R_5=H$).

Acid hydrolysis of the 2-chloro isomer XIXa provides pyridones such as XIIc. Acid hydrolysis of the 3-chloropyridines XIXb provides chlorides such as XIb.

Several other pyridones such as XIId and XIIe are more easily prepared by forming the pyridone on an existing heterocycle, examples of which are shown in Equations 19a and 19b.

Equation 19a

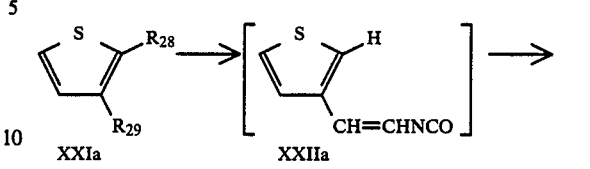

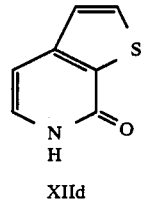

where
$R_{28}=H$
$R_{29}=$

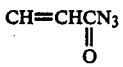

(b) Isocyanates such as XXIIa are formed in situ and cyclized to pyridones XIId as taught by F. Eloy and A. Deryckere, *Bull. Soc., Chim. Belges,* 79 (1970) 301-312. This method has also been used to prepare the thieno[3,2-c]pyridone isomer starting from XXIa ($R_{28}=CH=CHC(=O)N_3$, $R_{29}=H$).

Equation 19b

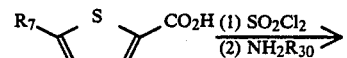

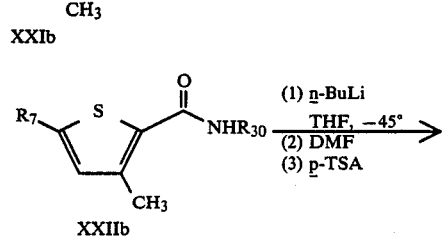

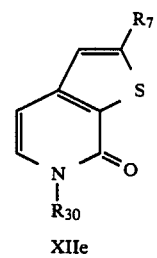

where
$R_7$ is as previously defined; and
$R_{30}$ is t-butyl.

Metallation of amides XXIIb, prepared from the corresponding acid XXIb by methods known to one skilled in the art, with 2.0 equivalents of n-butyllithium followed by quenching with N,N-dimethylformamide and para-toluenesulfonic acid afforded pyridones XIIe which may also be converted to chlorides of Formula XI by the methods described in Equation 15.

Equation 19c

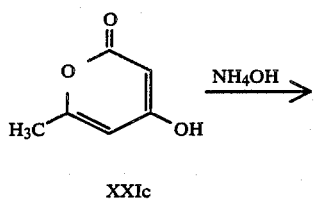

XXIc

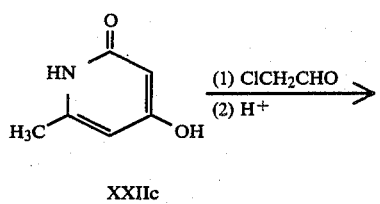

XXIIc

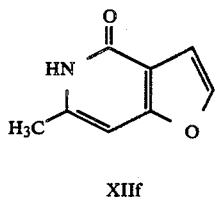

XIIf

Pyridones of Formula XIIf can be prepared following the procedures of E. Bisagni, et al., *J. Heterocycl. Chem.*, 12, 461 (1975) as shown in Equation 19c. Treatment of pyrone XXIc with ammonium hydroxide provided the corresponding pyrone XXIIc which was alkylated with chloroacetaldehyde followed by acid work-up to afford pyridones XIIf.

The amines of Formula X, in Equation 11, can be prepared by reduction of the corresponding nitro compounds of Formula XXIII, as shown in Equation 20.

Equation 20

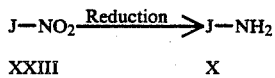

The reduction of nitro compounds, prepared by methods known to one skilled in the art, to amines can be carried out by any of several methods as described in *Preparative Organic Chemistry*, 4th Ed., pp. 557–563, John Wiley and Sons, New York and London, G. Hilgetag and A. Martine, ed.; and S. A. Harris, et al., *J. Am. Chem. Soc.*, 61, 1242 (1939).

Nitro compounds of Formula XXIIIa can be prepared by nitration of the corresponding pyridones XXIV as shown below.

Equation 21

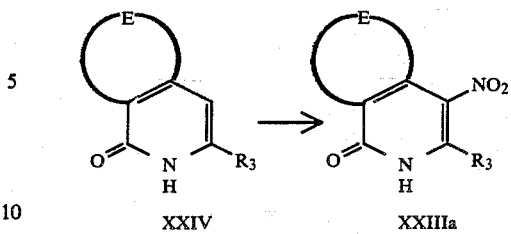

where E and R$_3$ are as previously defined.

The nitration is carried out in strong acid, such as acetic acid, according to the method taught by Eloy and Deryckere, *Bull. Soc. Chim. Belges*, 79 (1970) 407–414. Pyridones XXIIIa can be converted to the corresponding pyridine chlorides as described in Equation 15.

Additional methods to prepare heterocyclic nitro compounds similar to XXIII are described in European Publication No. 107,979.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines," Vol. XVI of the series mentioned above, which is herein incorporated by reference. The 2-amino-1,3,5-triazines of Formula III, where A is A-1 and Z is N, can be prepared according to methods described by E. M. Smolin and L. Rapaport in "s-Triazines and Derivatives," Vol. XIII.

Pyrimidines of Formula III, where A is A-1 and Y is an acetal or thioacetal substituent, can be prepared by methods taught in European Publication No. 84,244 (published July 27, 1983).

Pyrimidines of Formula III, where A is A-1 and Y is cyclopropyl or OCF$_2$H, can be synthesized according to the methods taught in South African Patent Application No. 83/7434 and South African Publication No. 82/5045, respectively.

Compounds of Formula III, where A is A-2 or A-3, can be prepared by procedures disclosed in U.S. Pat. No. 4,339,267.

Compounds of Formula III, where A is A-5, can be prepared by methods taught in U.S. Pat. No. 4,421,550.

Compounds of Formula III, where A is A-6, can be prepared by methods taught in European Publication No. 94,260 (published Nov. 16, 1983).

The preparation of the compounds of this invention is further illustrated by the following examples.

EXAMPLE 1

1,3-Dihydro-6-methyl-oxofuro[3,4-c]pyridine-4-thiouronium salt

A solution of 6.0 g of 4-chloro-1,3-dihydro-6-methyl-oxofuro[3,4-c]pyridine [prepared using the procedure of W. F. Bruce and H. W. Coover, *J. Am. Chem. Soc.*, 66, 2092 (1944)] and 2.5 g of thiourea in 25 mL DMF was heated at 50° to 60° C. for 3 hours. After cooling, the resulting precipitate was collected by filtration and washed with ether to provide 6.74 g of the title compound as a yellow solid, m.p. 205°–208° C.(d).

EXAMPLE 2

4-(Hydroxymethyl)-2-mercapto-6-methyl-3-pyridinecarboxylic acid

A solution of 6 g of the above thiouronium salt was dissolved in 10% sodium hydroxide. After 15 minutes the solution was acidified with 10% HCl. The resulting precipitate was collected by filtration and washed with water to provide the title compound as a yellow solid, m.p. >270° C.

EXAMPLE 3

1,3-Dihydro-6-methyl-3-oxofuro[3,4-c]pyridine-4-sulfonamide

A mixture of 2.0 g of the compound from Example 2, 17 mL of water, 33 mL of methylene chloride and 2.1 mL of concentrated HCl was cooled to −5° C. Keeping the temperature between 5° and 10° C., 35 mL of a 6% sodium hypochlorite solution was added over 15 minutes. After an additional 20 minutes at 0° C., the mixture was poured into water and extracted with methylene chloride. The organic phase was washed with sodium bisulfite and dried over sodium sulfate.

The solution of the sulfonyl chloride was cooled to −78° C. and 5 mL of dry ammonia added dropwise. After slowly warming to room temperature, the mixture was acidified with 10% HCl to pH 2 and sodium chloride added to give a saturated solution. The mixture was extracted with ethyl acetate to obtain 0.25 g of the title compound as a solid, m.p. 211°–213° C.

EXAMPLE 4

N-[(4,6-Dimethoxypyrimidin-2-yl)aminocarbonyl]-1,3-dihydro-6-methyl-3-oxofuro[3,4-c]pyridine-4-sulfonamide To a suspension of 0.21 g of the compound from Example 3 and 0.25 g of N-(4,6-dimethoxypyrimidin-2-yl)phenyl carbamate in 2 mL acetonitrile is added 0.14 mL 1,8-diazabicyclo[5.4.0]undec-7-ene. After 15 minutes, 6 mL water is added, followed by dropwise addition of 10% HCl. The resulting precipitate is collected by filtration and washed with water to provide 0.09 g of the title compound, m.p. 149°–153° C.

Using the procedures of Equations 1–21 and Examples 1–4, the following compounds of Tables 1–13 can be made by one skilled in the art. Where relevant, n=0 unless otherwise noted.

TABLE 1

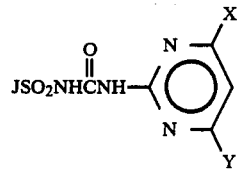

| J | q | Q | $R_1$ | $R_2$ | $R_3$ | $R_4$ | $R_5$ | X | Y | m.p. (°C.) |
|---|---|---|---|---|---|---|---|---|---|---|
| $J_1$ | 0 | O | H | H | — | H | H | $CH_3$ | $CH_3$ | |
| $J_1$ | 0 | O | H | H | — | H | H | $CH_3$ | $OCH_3$ | |
| $J_1$ | 0 | O | H | H | — | H | H | $OCH_3$ | $OCH_3$ | |
| $J_1$ | 0 | O | H | H | — | H | H | Cl | $OCH_3$ | |
| $J_1$ | 0 | O | H | H | — | H | $CH_3$ | $CH_3$ | $CH_3$ | |
| $J_1$ | 0 | O | H | $CH_3$ | — | $CH_3$ | $CH_3$ | $CH_3$ | $OCH_3$ | |
| $J_1$ | 0 | O | H | $CH_3$ | — | H | H | $CH_3$ | $CH_3$ | |
| $J_1$ | 0 | O | H | $CH_3$ | — | H | H | $CH_3$ | $OCH_3$ | |
| $J_1$ | 0 | O | H | $CH_3$ | — | H | H | $OCH_3$ | $OCH_3$ | 149–153 |
| $J_1$ | 0 | O | H | $CH_3$ | — | H | H | Cl | $OCH_3$ | |
| $J_1$ | 0 | O | H | Cl | — | H | H | $OCH_3$ | $OCH_3$ | |
| $J_1$ | 0 | O | H | $OCH_3$ | — | H | H | Cl | $OCH_3$ | |
| $J_1$ | 0 | O | Cl | H | — | H | H | $CH_3$ | $CH_3$ | |
| $J_1$ | 0 | O | $CH_3$ | H | — | H | H | $CH_3$ | $OCH_3$ | |
| $J_1$ | 0 | S | H | H | — | H | H | $CH_3$ | $OCH_3$ | |
| $J_1$ | 0 | NH | H | H | — | H | H | $OCH_3$ | $OCH_3$ | |
| $J_1$ | 0 | $NCH_3$ | H | H | — | H | H | $CH_3$ | $OCH_3$ | |
| $J_1$ | 1 | O | H | H | — | H | H | $CH_3$ | $CH_3$ | |
| $J_1$ | 1 | O | H | H | — | H | H | $CH_3$ | $OCH_3$ | |
| $J_1$ | 1 | O | H | H | — | H | H | $OCH_3$ | $OCH_3$ | |
| $J_1$ | 1 | O | H | H | — | H | H | Cl | $OCH_3$ | |
| $J_1$ | 1 | O | H | H | — | H | $CH_3$ | $CH_3$ | $CH_3$ | |
| $J_1$ | 1 | O | H | H | — | H | $CH_3$ | $CH_3$ | $OCH_3$ | |
| $J_1$ | 1 | O | H | H | — | H | $CH_3$ | $OCH_3$ | $OCH_3$ | |
| $J_1$ | 1 | O | H | H | — | H | $CH_3$ | Cl | $OCH_3$ | |
| $J_1$ | 1 | O | H | H | — | $CH_3$ | $CH_3$ | $CH_3$ | $OCH_3$ | |
| $J_1$ | 1 | O | H | Cl | — | H | H | $OCH_3$ | $OCH_3$ | |
| $J_1$ | 1 | O | H | $OCH_3$ | — | H | H | Cl | $OCH_3$ | |
| $J_1$ | 1 | S | H | H | — | H | H | $CH_3$ | $OCH_3$ | |
| $J_1$ | 1 | NH | H | H | — | H | H | $OCH_3$ | $OCH_3$ | |
| $J_1$ | 1 | $NCH_3$ | H | H | — | H | H | Cl | $OCH_3$ | |
| $J_2$ | 0 | O | H | — | H | H | H | $CH_3$ | $OCH_3$ | |
| $J_2$ | 0 | O | H | — | H | H | H | $OCH_3$ | $OCH_3$ | |
| $J_2$ | 0 | O | H | — | H | H | $CH_3$ | Cl | $OCH_3$ | |
| $J_2$ | 0 | O | H | — | H | $CH_3$ | $CH_3$ | $CH_3$ | $OCH_3$ | |
| $J_2$ | 0 | O | H | — | Cl | H | H | $OCH_3$ | $OCH_3$ | |
| $J_2$ | 0 | O | H | — | Cl | H | H | Cl | $OCH_3$ | |
| $J_2$ | 0 | O | H | — | Cl | H | H | $CH_3$ | $CH_3$ | |
| $J_2$ | 0 | O | H | — | $OCH_3$ | H | H | $CH_3$ | $OCH_3$ | |
| $J_2$ | 0 | O | H | — | $CH_3$ | H | H | $OCH_3$ | $OCH_3$ | |
| $J_2$ | 0 | O | $CH_3$ | — | H | H | H | $CH_3$ | $OCH_3$ | |

TABLE 1-continued

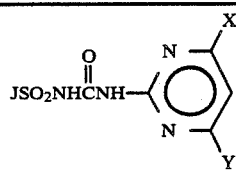

| J | q | Q | R₁ | R₂ | R₃ | R₄ | R₅ | X | Y | m.p. (°C.) |
|---|---|---|----|----|----|----|----|----|----|------------|
| J₂ | 0 | O | Cl | — | H | H | H | OCH₃ | OCH₃ | |
| J₂ | 0 | O | OCH₃ | — | H | H | H | Cl | OCH₃ | |
| J₂ | 0 | O | CH₃ | — | CH₃ | H | H | CH₃ | OCH₃ | |
| J₂ | 0 | O | Cl | — | Cl | H | H | OCH₃ | OCH₃ | |
| J₂ | 0 | S | H | — | H | H | H | CH₃ | OCH₃ | |
| J₂ | 0 | NH | H | — | H | H | H | OCH₃ | OCH₃ | |
| J₂ | 0 | NCH₃ | H | — | H | H | H | Cl | OCH₃ | |
| J₂ | 1 | O | H | — | H | H | H | CH₃ | CH₃ | |
| J₂ | 1 | O | H | — | H | H | H | CH₃ | OCH₃ | |
| J₂ | 1 | O | H | — | H | H | H | OCH₃ | OCH₃ | |
| J₂ | 1 | O | H | — | H | H | H | Cl | OCH₃ | |
| J₂ | 1 | O | H | — | H | H | CH₃ | CH₃ | OCH₃ | |
| J₂ | 1 | O | H | — | H | CH₃ | CH₃ | OCH₃ | OCH₃ | |
| J₂ | 1 | O | H | — | Cl | H | H | CH₃ | OCH₃ | |
| J₂ | 1 | O | H | — | CH₃ | H | H | OCH₃ | OCH₃ | |
| J₂ | 1 | O | H | — | OCH₃ | H | H | Cl | OCH₃ | |
| J₂ | 1 | O | Cl | — | H | H | H | CH₃ | OCH₃ | |
| J₂ | 1 | O | CH₃ | — | H | H | H | OCH₃ | OCH₃ | |
| J₂ | 1 | O | OCH₃ | — | H | H | H | Cl | OCH₃ | |
| J₂ | 1 | O | Cl | — | Cl | H | H | CH₃ | OCH₃ | |
| J₂ | 1 | O | CH₃ | — | CH₃ | H | H | OCH₃ | OCH₃ | |
| J₂ | 1 | S | H | — | H | H | H | Cl | OCH₃ | |
| J₂ | 1 | NH | H | — | H | H | H | CH₃ | OCH₃ | |
| J₂ | 1 | NCH₃ | H | — | H | H | H | OCH₃ | OCH₃ | |
| J₁₇ | — | — | H | H | — | — | H | Cl | OCH₃ | |
| J₁₇ | — | — | H | H | — | — | H | CH₃ | OCH₃ | |
| J₁₇ | — | — | H | H | — | — | CH₃ | OCH₃ | OCH₃ | |
| J₁₇ | — | — | H | Cl | — | — | H | CH₃ | OCH₃ | |
| J₁₇ | — | — | Cl | H | — | — | H | OCH₃ | OCH₃ | |
| J₁₈ | — | — | H | — | H | — | H | Cl | OCH₃ | |
| J₁₈ | — | — | H | — | H | — | H | CH₃ | OCH₃ | |
| J₁₈ | — | — | H | — | H | — | CH₃ | OCH₃ | OCH₃ | |
| J₁₈ | — | — | Cl | — | Cl | — | H | Cl | OCH₃ | |

TABLE 1a

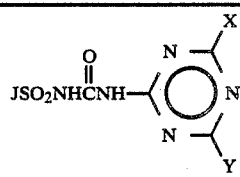

| J | q | Q | R₁ | R₂ | R₃ | R₄ | R₅ | X | Y | m.p. (°C.) |
|---|---|---|----|----|----|----|----|----|----|------------|
| J₁ | 0 | O | H | H | — | H | H | CH₃ | CH₃ | |
| J₁ | 0 | O | H | H | — | H | H | CH₃ | OCH₃ | |
| J₁ | 0 | O | H | H | — | H | H | OCH₃ | OCH₃ | |
| J₁ | 0 | O | H | H | — | H | H | NHCH₃ | CH₂CH₃ | |
| J₁ | 0 | O | H | H | — | H | CH₃ | CH₃ | CH₃ | |
| J₁ | 0 | O | H | CH₃ | — | CH₃ | CH₃ | CH₃ | OCH₃ | |
| J₁ | 0 | O | H | CH₃ | — | H | H | CH₃ | CH₃ | |
| J₁ | 0 | O | H | CH₃ | — | H | H | CH₃ | OCH₃ | |
| J₁ | 0 | O | H | CH₃ | — | H | H | OCH₃ | OCH₃ | |
| J₁ | 0 | O | H | CH₃ | — | H | H | NHCH₃ | CH₂CH₃ | |
| J₁ | 0 | O | H | Cl | — | H | H | OCH₃ | OCH₃ | |
| J₁ | 0 | O | H | OCH₃ | — | H | H | NHCH₃ | CH₂CH₃ | |
| J₁ | 0 | O | Cl | H | — | H | H | CH₃ | CH₃ | |
| J₁ | 0 | O | CH₃ | H | — | H | H | CH₃ | OCH₃ | |
| J₁ | 0 | S | H | H | — | H | H | CH₃ | OCH₃ | |
| J₁ | 0 | NH | H | H | — | H | H | OCH₃ | OCH₃ | |
| J₁ | 0 | NCH₃ | H | H | — | H | H | CH₃ | OCH₃ | |
| J₁ | 1 | O | H | H | — | H | H | CH₃ | CH₃ | |
| J₁ | 1 | O | H | H | — | H | H | CH₃ | OCH₃ | |
| J₁ | 1 | O | H | H | — | H | H | OCH₃ | OCH₃ | |
| J₁ | 1 | O | H | H | — | H | H | NHCH₃ | CH₂CH₃ | |
| J₁ | 1 | O | H | H | — | H | CH₃ | CH₃ | CH₃ | |
| J₁ | 1 | O | H | H | — | H | CH₃ | CH₃ | OCH₃ | |
| J₁ | 1 | O | H | H | — | H | CH₃ | OCH₃ | OCH₃ | |

TABLE 1a-continued

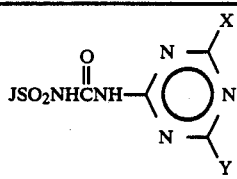

| J | q | Q | $R_1$ | $R_2$ | $R_3$ | $R_4$ | $R_5$ | X | Y | m.p. (°C.) |
|---|---|---|---|---|---|---|---|---|---|---|
| $J_1$ | 1 | O | H | H | — | H | $CH_3$ | $NHCH_3$ | $CH_2CH_3$ | |
| $J_1$ | 1 | O | H | H | — | $CH_3$ | $CH_3$ | $CH_3$ | $OCH_3$ | |
| $J_1$ | 1 | O | H | Cl | — | H | H | $OCH_3$ | $OCH_3$ | |
| $J_1$ | 1 | O | H | Cl | — | H | H | $OCH_3$ | $OCH_3$ | |
| $J_1$ | 1 | O | H | $OCH_3$ | — | H | H | $NHCH_3$ | $CH_2CH_3$ | |
| $J_1$ | 1 | S | H | H | — | H | H | $CH_3$ | $OCH_3$ | |
| $J_1$ | 1 | NH | H | H | — | H | H | $OCH_3$ | $OCH_3$ | |
| $J_1$ | 1 | $NCH_3$ | H | H | — | H | H | $NHCH_3$ | $CH_2CH_3$ | |
| $J_2$ | 0 | O | H | — | H | H | H | $CH_3$ | $OCH_3$ | |
| $J_2$ | 0 | O | H | — | H | H | H | $OCH_3$ | $OCH_3$ | |
| $J_2$ | 0 | O | H | — | H | H | $CH_3$ | $NHCH_3$ | $CH_2CH_3$ | |
| $J_2$ | 0 | O | H | — | H | $CH_3$ | $CH_3$ | $CH_3$ | $OCH_3$ | |
| $J_2$ | 0 | O | H | — | Cl | H | H | $OCH_3$ | $OCH_3$ | |
| $J_2$ | 0 | O | H | — | Cl | H | H | $NHCH_3$ | $CH_2CH_3$ | |
| $J_2$ | 0 | O | H | — | Cl | H | H | $CH_3$ | $CH_3$ | |
| $J_2$ | 0 | O | H | — | $OCH_3$ | H | H | $CH_3$ | $OCH_3$ | |
| $J_2$ | 0 | O | H | — | $CH_3$ | H | H | $OCH_3$ | $OCH_3$ | |
| $J_2$ | 0 | O | $CH_3$ | — | H | H | H | $CH_3$ | $OCH_3$ | |
| $J_2$ | 0 | O | Cl | — | H | H | H | $OCH_3$ | $OCH_3$ | |
| $J_2$ | 0 | O | $OCH_3$ | — | H | H | H | $NHCH_3$ | $CH_2CH_3$ | |
| $J_2$ | 0 | O | $CH_3$ | — | $CH_3$ | H | H | $CH_3$ | $OCH_3$ | |
| $J_2$ | 0 | O | Cl | — | Cl | H | H | $OCH_3$ | $OCH_3$ | |
| $J_2$ | 0 | S | H | — | H | H | H | $CH_3$ | $OCH_3$ | |
| $J_2$ | 0 | NH | H | — | H | H | H | $OCH_3$ | $OCH_3$ | |
| $J_2$ | 1 | O | H | — | H | H | H | $CH_3$ | $CH_3$ | |
| $J_2$ | 1 | O | H | — | H | H | H | $CH_3$ | $OCH_3$ | |
| $J_2$ | 1 | O | H | — | H | H | H | $OCH_3$ | $OCH_3$ | |
| $J_2$ | 1 | O | H | — | H | H | H | $NHCH_3$ | $CH_2CH_3$ | |
| $J_2$ | 1 | O | H | — | H | H | $CH_3$ | $CH_3$ | $OCH_3$ | |
| $J_2$ | 1 | O | H | — | H | $CH_3$ | $CH_3$ | $OCH_3$ | $OCH_3$ | |
| $J_2$ | 1 | O | H | — | Cl | H | H | $CH_3$ | $OCH_3$ | |
| $J_2$ | 1 | O | H | — | $CH_3$ | H | H | $OCH_3$ | $OCH_3$ | |
| $J_2$ | 1 | O | H | — | $OCH_3$ | H | H | $NHCH_3$ | $CH_2CH_2$ | |
| $J_2$ | 1 | O | Cl | — | H | H | H | $CH_3$ | $OCH_3$ | |
| $J_2$ | 1 | O | $CH_3$ | — | H | H | H | $OCH_3$ | $OCH_3$ | |
| $J_2$ | 1 | O | $OCH_3$ | — | H | H | H | $NHCH_3$ | $CH_2CH_3$ | |
| $J_2$ | 1 | O | Cl | — | Cl | H | H | $CH_3$ | $OCH_3$ | |
| $J_2$ | 1 | O | $CH_3$ | — | $CH_3$ | H | H | $OCH_3$ | $OCH_3$ | |
| $J_2$ | 1 | S | H | — | H | H | H | $NHCH_3$ | $CH_2CH_3$ | |
| $J_2$ | 1 | NH | H | — | H | H | H | $CH_3$ | $OCH_3$ | |
| $J_2$ | 1 | $NCH_3$ | H | — | H | H | H | $OCH_3$ | $OCH_3$ | |
| $J_{17}$ | — | — | H | H | — | — | H | $NHCH_3$ | $CH_2CH_3$ | |
| $J_{17}$ | — | — | H | H | — | — | H | $CH_3$ | $OCH_3$ | |
| $J_{17}$ | — | — | H | H | — | — | $CH_3$ | $OCH_3$ | $OCH_3$ | |
| $J_{17}$ | — | — | H | Cl | — | — | H | $CH_3$ | $OCH_3$ | |
| $J_{17}$ | — | — | Cl | H | — | — | H | $OCH_3$ | $OCH_3$ | |
| $J_{18}$ | — | — | H | — | H | — | H | $NHCH_3$ | $CH_2CH_3$ | |
| $J_{18}$ | — | — | H | — | H | — | H | $CH_3$ | $OCH_3$ | |
| $J_{18}$ | — | — | H | — | H | — | $CH_3$ | $OCH_3$ | $OCH_3$ | |
| $J_{18}$ | — | — | Cl | — | Cl | — | H | $NHCH_3$ | $CH_2CH_3$ | |

TABLE 2

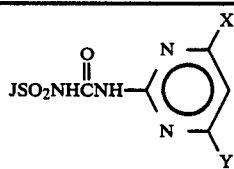

| J | q | $R_1$ | $R_2$ | $R_3$ | $R_4$ | $R_6$ | $R_7$ | X | Y | m.p. (°C.) |
|---|---|---|---|---|---|---|---|---|---|---|
| $J_3$ | 0 | H | H | — | H | H | — | $CH_3$ | $CH_3$ | |
| $J_3$ | 0 | H | H | — | H | H | — | $CH_3$ | $OCH_3$ | |
| $J_3$ | 0 | H | H | — | H | H | — | Cl | $OCH_3$ | |
| $J_3$ | 0 | H | H | — | H | $CH_3$ | — | $CH_3$ | $OCH_3$ | |
| $J_3$ | 0 | H | H | — | H | $CH_3$ | — | $CH_3$ | $CH_3$ | |
| $J_3$ | 0 | H | H | — | H | $CH_3$ | — | $OCH_3$ | $OCH_3$ | |
| $J_3$ | 0 | H | H | — | H | $CH_3$ | — | $OCH_3$ | $OCH_3$ | |

TABLE 2-continued

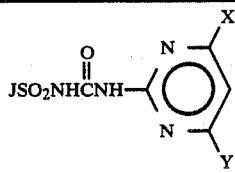

| J | q | $R_1$ | $R_2$ | $R_3$ | $R_4$ | $R_6$ | $R_7$ | X | Y | m.p. (°C.) |
|---|---|---|---|---|---|---|---|---|---|---|
| $J_3$ | 0 | H | H | — | H | $CH_3$ | — | Cl | $OCH_3$ | |
| $J_3$ | 0 | H | H | — | H | $C_2H_5$ | — | $CH_3$ | $OCH_3$ | |
| $J_3$ | 0 | H | H | — | H | $n$-$C_3H_7$ | — | $CH_3$ | $CH_3$ | |
| $J_3$ | 0 | H | H | — | H | $n$-$C_3H_7$ | — | $CH_3$ | $OCH_3$ | |
| $J_3$ | 0 | H | H | — | H | $n$-$C_3H_7$ | — | $OCH_3$ | $OCH_3$ | |
| $J_3$ | 0 | H | H | — | H | $n$-$C_3H_7$ | — | Cl | $OCH_3$ | |
| $J_3$ | 0 | H | H | — | H | $n$-$C_4H_9$ | — | $CH_3$ | $OCH_3$ | |
| $J_3$ | 0 | H | H | — | H | $CH_2CH_2F$ | — | $OCH_3$ | $OCH_3$ | |
| $J_3$ | 0 | H | H | — | H | $CH_2CH_2OCH_3$ | — | Cl | $OCH_3$ | |
| $J_3$ | 0 | H | H | — | H | $CH_2CH=CH_2$ | — | $CH_3$ | $OCH_3$ | |
| $J_3$ | 0 | H | H | — | H | $CH_2C\equiv CH$ | — | $OCH_3$ | $OCH_3$ | |
| $J_3$ | 0 | H | H | — | H | $C(O)CH_3$ | — | $CH_3$ | $OCH_{33}$ | |
| $J_3$ | 0 | H | H | — | H | $CO_2CH_3$ | — | $OCH_3$ | $OCH_3$ | |
| $J_3$ | 0 | H | H | — | $CH_3$ | $CH_3$ | — | NH | $OCH_3$ | |
| $J_3$ | 0 | H | H | — | $C_2H_5$ | $CH_3$ | — | $CH_3$ | $OCH_3$ | |
| $J_3$ | 0 | H | Cl | — | H | $n$-$C_3H_7$ | — | $OCH_3$ | $OCH_3$ | |
| $J_3$ | 0 | H | $CH_3$ | — | H | $n$-$C_3H_7$ | — | Cl | $OCH_3$ | |
| $J_3$ | 0 | H | $OCH_3$ | — | H | $n$-$C_3H_7$ | — | $CH_3$ | $OCH_3$ | |
| $J_3$ | 0 | Cl | H | — | H | $n$-$C_3H_7$ | — | $OCH_3$ | $OCH_3$ | |
| $J_3$ | 0 | $CH_3$ | H | — | H | $n$-$C_3H_7$ | — | Cl | $OCH_3$ | |
| $J_3$ | 1 | H | H | — | H | H | — | $CH_3$ | $OCH_3$ | |
| $J_3$ | 1 | H | H | — | H | H | — | $OCH_3$ | $OCH_3$ | |
| $J_3$ | 1 | H | H | — | H | $CH_3$ | — | Cl | $OCH_3$ | |
| $J_3$ | 1 | H | H | — | H | $CH_3$ | — | $CH_3$ | $OCH_3$ | |
| $J_3$ | 1 | H | H | — | H | $n$-$C_3H_7$ | — | $OCH_3$ | $OCH_3$ | |
| $J_3$ | 1 | H | H | — | H | $n$-$C_3H_7$ | — | Cl | $OCH_3$ | |
| $J_3$ | 1 | H | H | — | H | $n$-$C_3H_7$ | — | $CH_3$ | $CH_3$ | |
| $J_3$ | 1 | H | H | — | H | $n$-$C_3H_7$ | — | $CH_3$ | $OCH_3$ | |
| $J_3$ | 1 | H | H | — | $CH_3$ | $CH_3$ | — | $OCH_3$ | $OCH_3$ | |
| $J_3$ | 1 | H | Cl | — | H | $n$-$C_3H_7$ | — | Cl | $OCH_3$ | |
| $J_3$ | 1 | H | $CH_3$ | — | H | $n$-$C_3H_7$ | — | $CH_3$ | $OCH_3$ | |
| $J_3$ | 1 | H | $OCH_3$ | — | H | $n$-$C_4H_9$ | — | $OCH_3$ | $OCH_3$ | |
| $J_3$ | 1 | Cl | H | — | H | $n$-$C_4H_9$ | — | Cl | $OCH_3$ | |
| $J_3$ | 1 | $CH_3$ | H | — | H | $n$-$C_4H_9$ | — | $CH_3$ | $OCH_3$ | |
| $J_4$ | 0 | H | — | H | H | H | — | $CH_3$ | $CH_3$ | |
| $J_4$ | 0 | H | — | H | H | H | — | $CH_3$ | $OCH_3$ | |
| $J_4$ | 0 | H | — | H | H | H | — | $OCH_3$ | $OCH_3$ | |
| $J_4$ | 0 | H | — | H | H | H | — | Cl | $OCH_3$ | |
| $J_4$ | 0 | H | — | H | H | $CH_3$ | — | $CH_3$ | $CH_3$ | |
| $J_4$ | 0 | H | — | H | H | $CH_3$ | — | $CH_3$ | $OCH_3$ | |
| $J_4$ | 0 | H | — | H | H | $CH_3$ | — | $OCH_3$ | $OCH_3$ | |
| $J_4$ | 0 | H | — | H | H | $CH_3$ | — | Cl | $OCH_3$ | |
| $J_4$ | 0 | H | — | H | H | $C_2H_5$ | — | $CH_3$ | $OCH_3$ | |
| $J_4$ | 0 | H | — | H | H | $n$-$C_3H_7$ | — | $CH_3$ | $OCH_3$ | |
| $J_4$ | 0 | H | — | H | H | $n$-$C_3H_7$ | — | $OCH_3$ | $OCH_3$ | |
| $J_4$ | 0 | H | — | H | H | $n$-$C_3H_7$ | — | Cl | $OCH_3$ | |
| $J_4$ | 0 | H | — | H | H | $n$-$C_4H_9$ | — | $CH_3$ | $CH_3$ | |
| $J_4$ | 0 | H | — | H | H | $n$-$C_4H_9$ | — | $CH_3$ | $OCH_3$ | |
| $J_4$ | 0 | H | — | H | H | $n$-$C_4H_9$ | — | $OCH_3$ | $OCH_3$ | |
| $J_4$ | 0 | H | — | H | H | $n$-$C_4H_9$ | — | Cl | $OCH_3$ | |
| $J_4$ | 0 | H | — | H | H | $CH_2CH_2F$ | — | $CH_3$ | $OCH_3$ | |
| $J_4$ | 0 | H | — | H | H | $CH_2CH_2OCH_3$ | — | $OCH_3$ | $OCH_3$ | |
| $J_4$ | 0 | H | — | H | H | $CH_2CH=CH_2$ | — | Cl | $OCH_3$ | |
| $J_4$ | 0 | H | — | H | H | $CH_2C\equiv CH$ | — | $CH_3$ | $OCH_3$ | |
| $J_4$ | 0 | H | — | H | H | $C(O)CH_3$ | — | $OCH_3$ | $OCH_3$ | |
| $J_4$ | 0 | H | — | H | H | $CO_2CH_3$ | — | Cl | $OCH_3$ | |
| $J_4$ | 0 | H | — | H | $CH_3$ | H | — | $CH_3$ | $OCH_3$ | |
| $J_4$ | 0 | H | — | Cl | H | $CH_3$ | — | $OCH_3$ | $OCH_3$ | |
| $J_4$ | 0 | H | — | $CH_3$ | H | $CH_3$ | — | Cl | $OCH_3$ | |
| $J_4$ | 0 | H | — | $OCH_3$ | H | $n$-$C_4H_9$ | — | $CH_3$ | $OCH_3$ | |
| $J_4$ | 0 | $CH_3$ | — | H | H | $n$-$C_4H_9$ | — | $OCH_3$ | $OCH_3$ | |
| $J_4$ | 0 | Cl | — | H | H | H | — | Cl | $OCH_3$ | |
| $J_4$ | 0 | $OCH_3$ | — | H | H | CH | — | $CH_3$ | $OCH_3$ | |
| $J_4$ | 0 | Cl | — | Cl | H | H | — | $OCH_3$ | $OCH_3$ | |
| $J_4$ | 0 | $CH_3$ | — | $CH_3$ | H | $CH_3$ | — | Cl | $OCH_3$ | |
| $J_4$ | 1 | H | — | H | H | H | — | $CH_3$ | $OCH_3$ | |
| $J_4$ | 1 | H | — | H | H | H | — | $OCH_3$ | $OCH_3$ | |
| $J_4$ | 1 | H | — | H | H | $CH_3$ | — | Cl | $OCH_3$ | |
| $J_4$ | 1 | H | — | H | H | $CH_3$ | — | $CH_3$ | $OCH_3$ | |
| $J_4$ | 1 | H | — | H | H | $C_2H_5$ | — | $OCH_3$ | $OCH_3$ | |
| $J_4$ | 1 | H | — | H | H | $n$-$C_3H_7$ | — | Cl | $OCH_3$ | |
| $J_4$ | 1 | H | — | H | H | $n$-$C_4H_9$ | — | $CH_3$ | $OCH_3$ | |

TABLE 2-continued

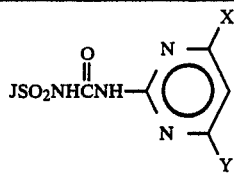

| J | q | R₁ | R₂ | R₃ | R₄ | R₆ | R₇ | X | Y | m.p. (°C.) |
|---|---|----|----|----|----|----|----|----|----|----|
| J₄ | 1 | H | — | H | CH₃ | H | — | OCH₃ | OCH₃ | |
| J₄ | 1 | H | — | Cl | H | CH₃ | — | Cl | OCH₃ | |
| J₄ | 1 | H | — | CH₃ | H | n-C₃H₇ | — | CH₃ | OCH₃ | |
| J₄ | 1 | H | — | OCH₃ | H | n-C₄H₉ | — | OCH₃ | OCH₃ | |
| J₄ | 1 | Cl | — | H | H | H | — | Cl | OCH₃ | |
| J₄ | 1 | OCH₃ | — | H | H | CH₃ | — | CH₃ | OCH₃ | |
| J₄ | 1 | CH₃ | — | H | H | n-C₃H₇ | — | OCH₃ | OCH₃ | |
| J₄ | 1 | Cl | — | Cl | H | n-C₃H₇ | — | Cl | OCH₃ | |
| J₄ | 1 | CH₃ | — | CH₃ | H | H | — | CH₃ | OCH₃ | |
| J₅ | — | H | H | — | — | — | H | CH₃ | CH₃ | |
| J₅ | — | H | H | — | — | — | H | OCH₃ | OCH₃ | |
| J₅ | — | H | H | — | — | — | H | OCH₃ | OCH₃ | |
| J₅ | — | H | H | — | — | — | H | Cl | OCH₃ | |
| J₅ | — | H | H | — | — | — | CH₃ | CH₃ | OCH₃ | |
| J₅ | — | H | Cl | — | — | — | H | OCH₃ | OCH₃ | |
| J₅ | — | H | CH₃ | — | — | — | H | Cl | OCH₃ | |
| J₅ | — | H | OCH₃ | — | — | — | H | CH₃ | OCH₃ | |
| J₅ | — | Cl | H | — | — | — | H | OCH₃ | OCH₃ | |
| J₅ | — | CH₃ | H | — | — | — | H | Cl | OCH₃ | |
| J₆ | — | H | — | H | — | — | H | CH₃ | CH₃ | |
| J₆ | — | H | — | H | — | — | H | CH₃ | OCH₃ | |
| J₆ | — | H | — | H | — | — | H | OCH₃ | OCH₃ | |
| J₆ | — | H | — | H | — | — | H | Cl | OCH₃ | |
| J₆ | — | H | — | H | — | — | CH₃ | CH₃ | OCH₃ | |
| J₆ | — | H | — | Cl | — | — | H | OCH₃ | OCH₃ | |
| J₆ | — | H | — | CH₃ | — | — | H | Cl | OCH₃ | |
| J₆ | — | H | — | OCH₃ | — | — | H | CH₃ | OCH₃ | |
| J₆ | — | Cl | — | H | — | — | H | OCH₃ | OCH₃ | |
| J₆ | — | CH₃ | — | H | — | — | H | Cl | OCH₃ | |
| J₆ | — | Cl | — | Cl | — | — | H | CH₃ | OCH₃ | |

TABLE 2a

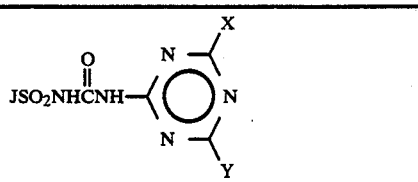

| J | q | R₁ | R₂ | R₃ | R₄ | R₆ | R₇ | X | Y | m.p. (°C.) |
|---|---|----|----|----|----|----|----|----|----|----|
| J₃ | 0 | H | H | — | H | H | — | CH₃ | CH₃ | |
| J₃ | 0 | H | H | — | H | H | — | CH₃ | OCH₃ | |
| J₃ | 0 | H | H | — | H | H | — | NHCH₃ | CH₂CH₃ | |
| J₃ | 0 | H | H | — | H | CH₃ | — | CH₃ | OCH₃ | |
| J₃ | 0 | H | H | — | H | CH₃ | — | CH₃ | CH₃ | |
| J₃ | 0 | H | H | — | H | CH₃ | — | OCH₃ | OCH₃ | |
| J₃ | 0 | H | H | — | H | CH₃ | — | OCH₃ | OCH₃ | |
| J₃ | 0 | H | H | — | H | CH₃ | — | NHCH₃ | CH₂CH₃ | |
| J₃ | 0 | H | H | — | H | C₂H₅ | — | CH₃ | OCH₃ | |
| J₃ | 0 | H | H | — | H | n-C₃H₇ | — | CH₃ | CH₃ | |
| J₃ | 0 | H | H | — | H | n-C₃H₇ | — | CH₃ | OCH₃ | |
| J₃ | 0 | H | H | — | H | n-C₃H₇ | — | OCH₃ | OCH₃ | |
| J₃ | 0 | H | H | — | H | n-C₃H₇ | — | NHCH₃ | CH₂CH₃ | |
| J₃ | 0 | H | H | — | H | n-C₄H₉ | — | CH₃ | OCH₃ | |
| J₃ | 0 | H | H | — | H | CH₂CH₂F | — | OCH₃ | OCH₃ | |
| J₃ | 0 | H | H | — | H | CH₂CH₂OCH₃ | — | NHCH₃ | CH₂CH₃ | |
| J₃ | 0 | H | H | — | H | CH₂CH=CH₂ | — | CH₃ | OCH₃ | |
| J₃ | 0 | H | H | — | H | CH₂C≡CH | — | OCH₃ | OCH₃ | |
| J₃ | 0 | H | H | — | H | C(O)CH₃ | — | CH₃ | OCH₃ | |
| J₃ | 0 | H | H | — | H | CO₂CH₃ | — | OCH₃ | OCH₃ | |
| J₃ | 0 | H | H | — | CH₃ | CH₃ | — | NH | OCH₃ | |
| J₃ | 0 | H | H | — | C₂H₅ | CH₃ | — | CH₃ | OCH₃ | |
| J₃ | 0 | H | Cl | — | H | n-C₃H₇ | — | OCH₃ | OCH₃ | |
| J₃ | 0 | H | CH₃ | — | H | n-C₃H₇ | — | NHCH₃ | CH₂CH₃ | |
| J₃ | 0 | H | OCH₃ | — | H | n-C₃H₇ | — | CH₃ | OCH₃ | |
| J₃ | 0 | Cl | H | — | H | n-C₃H₇ | — | OCH₃ | OCH₃ | |
| J₃ | 0 | CH₃ | H | — | H | n-C₃H₇ | — | NHCH₃ | CH₂CH₃ | |

TABLE 2a-continued

JSO₂NHCNH— [ring with X, Y, N substituents]

| J | q | R₁ | R₂ | R₃ | R₄ | R₆ | R₇ | X | Y | m.p. (°C.) |
|---|---|----|----|----|----|----|----|----|----|---|
| $J_3$ | 1 | H | H | — | H | H | — | CH₃ | OCH₃ | |
| $J_3$ | 1 | H | H | — | H | H | — | OCH₃ | OCH₃ | |
| $J_3$ | 1 | H | H | — | H | H | — | NHCH₃ | CH₂CH₃ | |
| $J_3$ | 1 | H | H | — | H | CH₃ | — | CH₃ | OCH₃ | |
| $J_3$ | 1 | H | H | — | H | n-C₃H₇ | — | OCH₃ | OCH₃ | |
| $J_3$ | 1 | H | H | — | H | n-C₃H₇ | — | NHCH₃ | CH₂CH₃ | |
| $J_3$ | 1 | H | H | — | H | n-C₃H₇ | — | CH₃ | CH₃ | |
| $J_3$ | 1 | H | H | — | H | n-C₃H₇ | — | CH₃ | OCH₃ | |
| $J_3$ | 1 | H | H | — | CH₃ | CH₃ | — | OCH₃ | OCH₃ | |
| $J_3$ | 1 | H | Cl | — | H | n-C₃H₇ | — | NHCH₃ | CH₂CH₃ | |
| $J_3$ | 1 | H | CH₃ | — | H | n-C₃H₇ | — | CH₃ | OCH₃ | |
| $J_3$ | 1 | H | OCH₃ | — | H | n-C₄H₉ | — | OCH₃ | OCH₃ | |
| $J_3$ | 1 | Cl | H | — | H | n-C₄H₉ | — | NHCH₃ | CH₂CH₃ | |
| $J_3$ | 1 | CH₃ | H | — | H | n-C₄H₉ | — | CH₃ | OCH₃ | |
| $J_4$ | 0 | H | — | H | H | H | — | CH₃ | CH₃ | |
| $J_4$ | 0 | H | — | H | H | H | — | CH₃ | OCH₃ | |
| $J_4$ | 0 | H | — | H | H | H | — | OCH₃ | OCH₃ | |
| $J_4$ | 0 | H | — | H | H | H | — | NHCH₃ | CH₂CH₃ | |
| $J_4$ | 0 | H | — | H | H | CH₃ | — | CH₃ | CH₃ | |
| $J_4$ | 0 | H | — | H | H | CH₃ | — | CH₃ | OCH₃ | |
| $J_4$ | 0 | H | — | H | H | CH₃ | — | OCH₃ | OCH₃ | |
| $J_4$ | 0 | H | — | H | H | CH₃ | — | NHCH₃ | CH₂CH₃ | |
| $J_4$ | 0 | H | — | H | H | C₂H₅ | — | CH₃ | OCH₃ | |
| $J_4$ | 0 | H | — | H | H | n-C₃H₇ | — | CH₃ | OCH₃ | |
| $J_4$ | 0 | H | — | H | H | n-C₃H₇ | — | OCH₃ | OCH₃ | |
| $J_4$ | 0 | H | — | H | H | n-C₃H₇ | — | NHCH₃ | CH₂CH₃ | |
| $J_4$ | 0 | H | — | H | H | n-C₄H₉ | — | CH₃ | CH₃ | |
| $J_4$ | 0 | H | — | H | H | n-C₄H₉ | — | CH₃ | OCH₃ | |
| $J_4$ | 0 | H | — | H | H | n-C₄H₉ | — | OCH₃ | OCH₃ | |
| $J_4$ | 0 | H | — | H | H | n-C₄H₉ | — | NHCH₃ | CH₂CH₃ | |
| $J_4$ | 0 | H | — | H | H | CH₂CH₂F | — | CH₃ | OCH₃ | |
| $J_4$ | 0 | H | — | H | H | CH₂CH₂OCH₃ | — | OCH₃ | OCH₃ | |
| $J_4$ | 0 | H | — | H | H | CH₂CH=CH₂ | — | NHCH₃ | CH₂CH₃ | |
| $J_4$ | 0 | H | — | H | H | CH₂C≡CH | — | CH₃ | OCH₃ | |
| $J_4$ | 0 | H | — | H | H | C(O)CH₃ | — | OCH₃ | OCH₃ | |
| $J_4$ | 0 | H | — | H | H | CO₂CH₃ | — | NHCH₃ | CH₂CH₃ | |
| $J_4$ | 0 | H | — | H | CH₃ | H | — | CH₃ | OCH₃ | |
| $J_4$ | 0 | H | — | Cl | H | CH₃ | — | OCH₃ | OCH₃ | |
| $J_4$ | 0 | H | — | CH₃ | H | CH₃ | — | NHCH₃ | CH₂CH₃ | |
| $J_4$ | 0 | H | — | OCH₃ | H | n-C₄H₉ | — | CH₃ | OCH₃ | |
| $J_4$ | 0 | CH₃ | — | H | H | n-C₄H₉ | — | OCH₃ | OCH₃ | |
| $J_4$ | 0 | Cl | — | H | H | H | — | NHCH₃ | CH₂CH₃ | |
| $J_4$ | 0 | OCH₃ | — | H | H | CH | — | CH₃ | OCH₃ | |
| $J_4$ | 0 | Cl | — | Cl | H | H | — | OCH₃ | OCH₃ | |
| $J_4$ | 0 | CH₃ | — | CH₃ | H | CH₃ | — | NHCH₃ | CH₂CH₃ | |
| $J_4$ | 1 | H | — | H | H | H | — | CH₃ | OCH₃ | |
| $J_4$ | 1 | H | — | H | H | H | — | OCH₃ | OCH₃ | |
| $J_4$ | 1 | H | — | H | H | CH₃ | — | NHCH₃ | CH₂CH₃ | |
| $J_4$ | 1 | H | — | H | H | CH₃ | — | CH₃ | OCH₃ | |
| $J_4$ | 1 | H | — | H | H | C₂H₅ | — | OCH₃ | OCH₃ | |
| $J_4$ | 1 | H | — | H | H | n-C₃H₇ | — | NHCH₃ | CH₂CH₃ | |
| $J_4$ | 1 | H | — | H | H | n-C₄H₉ | — | CH₃ | OCH₃ | |
| $J_4$ | 1 | H | — | H | CH₃ | H | — | OCH₃ | OCH₃ | |
| $J_4$ | 1 | H | — | Cl | H | CH₃ | — | NHCH₃ | CH₂CH₃ | |
| $J_4$ | 1 | H | — | CH₃ | H | n-C₃H₇ | — | CH₃ | OCH₃ | |
| $J_4$ | 1 | H | — | OCH₃ | H | n-C₄H₉ | — | OCH₃ | OCH₃ | |
| $J_4$ | 1 | Cl | — | H | H | H | — | NHCH₃ | CH₂CH₃ | |
| $J_4$ | 1 | OCH₃ | — | H | H | CH₃ | — | CH₃ | OCH₃ | |
| $J_4$ | 1 | CH₃ | — | H | H | n-C₃H₇ | — | OCH₃ | OCH₃ | |
| $J_4$ | 1 | Cl | — | Cl | H | n-C₃H₇ | — | NHCH₃ | CH₂CH₃ | |
| $J_4$ | 1 | CH₃ | — | CH₃ | H | H | — | CH₃ | OCH₃ | |
| $J_5$ | — | H | H | — | — | — | H | CH₃ | CH₃ | |
| $J_5$ | — | H | H | — | — | — | H | OCH₃ | OCH₃ | |
| $J_5$ | — | H | H | — | — | — | H | OCH₃ | OCH₃ | |
| $J_5$ | — | H | H | — | — | — | H | NHCH₃ | CH₂CH₃ | |
| $J_5$ | — | H | H | — | — | — | CH₃ | CH₃ | OCH₃ | |
| $J_5$ | — | H | Cl | — | — | — | H | OCH₃ | OCH₃ | |
| $J_5$ | — | H | CH₃ | — | — | — | H | NHCH₃ | CH₂CH₃ | |
| $J_5$ | — | H | OCH₃ | — | — | — | H | CH₃ | OCH₃ | |
| $J_5$ | — | Cl | H | — | — | — | H | OCH₃ | OCH₃ | |
| $J_5$ | — | CH₃ | H | — | — | — | H | NHCH₃ | CH₂CH₃ | |
| $J_6$ | — | H | — | H | — | — | H | CH₃ | CH₃ | |

TABLE 2a-continued

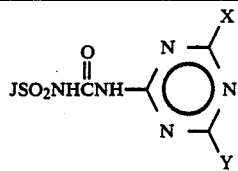

| J | q | R₁ | R₂ | R₃ | R₄ | R₆ | R₇ | X | Y | m.p. (°C.) |
|---|---|----|----|----|----|----|----|----|----|----|
| J₆ | — | H | — | H | — | — | H | CH₃ | OCH₃ | |
| J₆ | — | H | — | H | — | — | H | OCH₃ | OCH₃ | |
| J₆ | — | H | — | H | — | — | H | NHCH₃ | CH₂CH₃ | |
| J₆ | — | H | — | H | — | — | CH₃ | CH₃ | OCH₃ | |
| J₆ | — | H | — | Cl | — | — | H | OCH₃ | OCH₃ | |
| J₆ | — | H | — | CH₃ | — | — | H | NHCH₃ | CH₂CH₃ | |
| J₆ | — | H | — | OCH₃ | — | — | H | CH₃ | OCH₃ | |
| J₆ | — | Cl | — | H | — | — | H | OCH₃ | OCH₃ | |
| J₆ | — | CH₃ | — | H | — | — | H | NHCH₃ | CH₂CH₃ | |
| J₆ | — | Cl | — | Cl | — | — | H | CH₃ | OCH₃ | |

TABLE 3

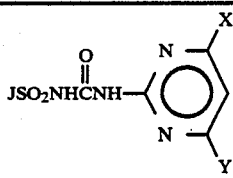

| J | q | Q₁ | R₁ | R₂ | R₃ | R₁₇ | R₁₈ | X | Y | m.p. (°C.) |
|---|---|----|----|----|----|----|----|----|----|----|
| J₇ | 0 | O | H | H | — | H | H | CH₃ | CH₃ | |
| J₇ | 0 | O | H | H | — | H | H | CH₃ | OCH₃ | |
| J₇ | 0 | O | H | H | — | H | H | OCH₃ | OCH₃ | |
| J₇ | 0 | O | H | H | — | H | H | Cl | OCH₃ | |
| J₇ | 0 | O | H | H | — | H | CH₃ | CH₃ | OCH₃ | |
| J₇ | 0 | O | H | H | — | CH₃ | CH₃ | OCH₃ | OCH₃ | |
| J₇ | 0 | O | H | Cl | — | H | H | Cl | OCH₃ | |
| J₇ | 0 | O | H | CH₃ | — | H | H | CH₃ | OCH₃ | |
| J₇ | 0 | O | H | OCH₃ | — | H | H | OCH₃ | OCH₃ | |
| J₇ | 0 | O | Cl | H | — | H | H | Cl | OCH₃ | |
| J₇ | 0 | O | CH | H | — | H | H | CH₃ | OCH₃ | |
| J₇ | 0 | S | H | H | — | H | H | CH₃ | CH₃ | |
| J₇ | 0 | S | H | H | — | H | H | CH₃ | OCH₃ | |
| J₇ | 0 | S | H | H | — | H | H | OCH₃ | OCH₃ | |
| J₇ | 0 | S | H | H | — | H | H | Cl | OCH₃ | |
| J₇ | 0 | S | H | H | — | H | CH₃ | CH₃ | OCH₃ | |
| J₇ | 0 | S | H | H | — | CH₃ | CH₃ | OCH₃ | OCH₃ | |
| J₇ | 0 | S | H | Cl | — | H | H | Cl | OCH₃ | |
| J₇ | 0 | S | H | OCH₃ | — | H | H | OCH₃ | OCH₃ | |
| J₇ | 0 | S | H | CH₃ | — | H | H | CH₃ | OCH₃ | |
| J₇ | 0 | S | Cl | H | — | H | H | CH₃ | OCH₃ | |
| J₇ | 0 | S | CH₃ | H | — | H | H | CH₃ | OCH₃ | |
| J₇ | 0 | SO₂ | H | H | — | H | H | OCH₃ | OCH₃ | |
| J₇ | 0 | SO₂ | H | H | — | H | H | CH₃ | OCH₃ | |
| J₇ | 0 | SO₂ | H | H | — | H | H | OCH₃ | OCH₃ | |
| J₇ | 0 | SO₂ | H | H | — | H | CH₃ | Cl | OCH₃ | |
| J₇ | 0 | SO₂ | H | Cl | — | H | H | CH₃ | OCH₃ | |
| J₇ | 0 | SO₂ | H | CH₃ | — | H | H | OCH₃ | OCH₃ | |
| J₇ | 0 | SO₂ | H | OCH₃ | — | H | H | Cl | OCH₃ | |
| J₇ | 0 | SO₂ | Cl | H | — | H | H | CH₃ | OCH₃ | |
| J₇ | 0 | SO₂ | OCH₃ | H | — | H | H | OCH₃ | OCH₃ | |
| J₇ | 0 | NH | H | H | — | H | H | Cl | OCH₃ | |
| J₇ | 0 | NH | H | H | — | H | H | CH₃ | OCH₃ | |
| J₇ | 0 | NH | H | H | — | H | CH₃ | OCH₃ | OCH₃ | |
| J₇ | 0 | NCH₃ | H | H | — | H | H | Cl | OCH₃ | |
| J₇ | 0 | NCH₃ | H | H | — | H | H | CH₃ | OCH₃ | |
| J₇ | 0 | NCH₃ | H | H | — | H | CH₃ | OCH₃ | OCH₃ | |
| J₇ | 1 | O | H | H | — | H | H | Cl | OCH₃ | |
| J₇ | 1 | O | H | H | — | H | H | CH₃ | OCH₃ | |
| J₇ | 1 | O | H | H | — | H | H | OCH₃ | OCH₃ | |
| J₇ | 1 | O | H | H | — | H | CH₃ | Cl | OCH₃ | |
| J₇ | 1 | O | H | H | — | CH₃ | CH₃ | CH₃ | OCH₃ | |
| J₇ | 1 | S | H | H | — | H | H | OCH₃ | OCH₃ | |

TABLE 3-continued

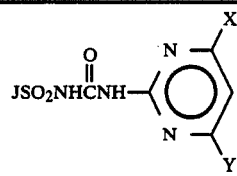

| J | q | Q₁ | R₁ | R₂ | R₃ | R₁₇ | R₁₈ | X | Y | m.p. (°C.) |
|---|---|----|----|----|----|----|----|----|----|----|
| J₇ | 1 | S | H | H | — | H | CH₃ | Cl | OCH₃ | |
| J₇ | 1 | SO₂ | H | H | — | H | H | CH₃ | OCH₃ | |
| J₇ | 1 | SO₂ | H | H | — | H | H | OCH₃ | OCH₃ | |
| J₇ | 1 | SO₂ | H | H | — | H | CH₃ | Cl | OCH₃ | |
| J₇ | 1 | SO₂ | H | H | — | CH₃ | CH₃ | CH₃ | OCH₃ | |
| J₇ | 1 | NH | H | H | — | H | H | OCH₃ | OCH₃ | |
| J₇ | 1 | NCH₃ | H | H | — | H | H | Cl | OCH₃ | |
| J₈ | 0 | O | H | — | H | H | H | CH₃ | CH₃ | |
| J₈ | 0 | O | H | — | H | H | H | CH₃ | OCH₃ | |
| J₈ | 0 | O | H | — | H | H | H | OCH₃ | OCH₃ | |
| J₈ | 0 | O | H | — | H | H | H | Cl | OCH₃ | |
| J₈ | 0 | O | H | — | H | H | CH₃ | CH₃ | OCH₃ | |
| J₈ | 0 | O | H | — | H | CH₃ | CH₃ | OCH₃ | OCH₃ | |
| J₈ | 0 | O | H | — | Cl | H | H | Cl | OCH₃ | |
| J₈ | 0 | O | H | — | OCH₃ | H | H | CH₃ | OCH₃ | |
| J₈ | 0 | O | H | — | CH₃ | H | H | OCH₃ | OCH₃ | |
| J₈ | 0 | O | Cl | — | H | H | H | Cl | OCH₃ | |
| J₈ | 0 | O | CH | — | H | H | H | CH₃ | OCH₃ | |
| J₈ | 0 | S | H | — | H | H | H | OCH₃ | OCH₃ | |
| J₈ | 0 | S | H | — | H | H | H | Cl | OCH₃ | |
| J₈ | 0 | SO₂ | H | — | H | H | H | CH₃ | OCH₃ | |
| J₈ | 0 | SO₂ | H | — | H | H | H | OCH₃ | OCH₃ | |
| J₈ | 0 | SO₂ | H | — | H | H | H | Cl | OCH₃ | |
| J₈ | 0 | SO₂ | H | — | H | H | CH₃ | CH₃ | OCH₃ | |
| J₈ | 0 | SO₂ | H | — | H | H | CH₃ | OCH₃ | OCH₃ | |
| J₈ | 0 | SO₂ | H | — | H | H | CH₃ | OCH₃ | OCH₃ | |
| J₈ | 0 | SO₂ | H | — | H | H | CH₂ | Cl | OCH₃ | |
| J₈ | 0 | SO₂ | H | — | H | CH₃ | CH₃ | CH₃ | OCH₃ | |
| J₈ | 0 | NH | H | — | H | H | H | OCH₃ | OCH₃ | |
| J₈ | 0 | NCH₃ | H | — | H | H | H | Cl | OCH₃ | |
| J₈ | 0 | NCH₃ | H | — | H | H | H | CH₃ | OCH₃ | |
| J₈ | 1 | O | H | — | H | H | H | CH₃ | CH₃ | |
| J₈ | 1 | O | H | — | H | H | H | CH₃ | OCH₃ | |
| J₈ | 1 | O | H | — | H | H | H | Cl | OCH₃ | |
| J₈ | 1 | O | H | — | H | H | CH₃ | CH₃ | OCH₃ | |
| J₈ | 1 | S | H | — | H | H | H | OCH₃ | OCH₃ | |
| J₈ | 1 | SO | H | — | H | H | H | Cl | OCH₃ | |
| J₈ | 1 | SO₂ | H | — | H | H | H | CH₃ | OCH₃ | |
| J₈ | 1 | SO₂ | H | — | H | H | CH₃ | OCH₃ | OCH₃ | |
| J₈ | 1 | NH | H | — | H | H | H | Cl | OCH₃ | |
| J₈ | 1 | NCH₃ | H | — | H | H | H | CH₃ | OCH₃ | |
| J₈ | 1 | NCH₃ | H | — | H | H | CH₃ | OCH₃ | OCH₃ | |

TABLE 3a

JSO$_2$NHCNH— [pyrimidine ring with X, Y, N substituents]

| J | q | Q$_1$ | R$_1$ | R$_2$ | R$_3$ | R$_{17}$ | R$_{18}$ | X | Y | m.p. (°C.) |
|---|---|---|---|---|---|---|---|---|---|---|
| J$_7$ | 0 | O | H | H | — | H | H | CH$_3$ | CH$_3$ | |
| J$_7$ | 0 | O | H | H | — | H | H | CH$_3$ | OCH$_3$ | |
| J$_7$ | 0 | O | H | H | — | H | H | OCH$_3$ | OCH$_3$ | |
| J$_7$ | 0 | O | H | H | — | H | H | NHCH$_3$ | CH$_2$CH$_3$ | |
| J$_7$ | 0 | O | H | H | — | H | CH$_3$ | CH$_3$ | OCH$_3$ | |
| J$_7$ | 0 | O | H | H | — | CH$_3$ | CH$_3$ | OCH$_3$ | OCH$_3$ | |
| J$_7$ | 0 | O | H | Cl | — | H | H | NHCH$_3$ | CH$_2$CH$_3$ | |
| J$_7$ | 0 | O | H | CH$_3$ | — | H | H | CH$_3$ | OCH$_3$ | |
| J$_7$ | 0 | O | H | OCH$_3$ | — | H | H | OCH$_3$ | OCH$_3$ | |
| J$_7$ | 0 | O | Cl | H | — | H | H | NHCH$_3$ | CH$_2$CH$_3$ | |
| J$_7$ | 0 | O | CH | H | — | H | H | OCH$_3$ | OCH$_3$ | |
| J$_7$ | 0 | S | H | H | — | H | H | CH$_3$ | CH$_3$ | |
| J$_7$ | 0 | S | H | H | — | H | H | CH$_3$ | OCH$_3$ | |
| J$_7$ | 0 | S | H | H | — | H | H | OCH$_3$ | OCH$_3$ | |
| J$_7$ | 0 | S | H | H | — | H | H | NHCH$_3$ | CH$_2$CH$_3$ | |
| J$_7$ | 0 | S | H | H | — | H | CH$_3$ | CH$_3$ | OCH$_3$ | |
| J$_7$ | 0 | S | H | H | — | CH$_3$ | CH$_3$ | OCH$_3$ | OCH$_3$ | |
| J$_7$ | 0 | S | H | Cl | — | H | H | NHCH$_2$ | CH$_2$CH$_3$ | |
| J$_7$ | 0 | S | H | OCH$_3$ | — | H | H | CH$_3$ | OCH$_3$ | |
| J$_7$ | 0 | S | H | CH$_3$ | — | H | H | OCH$_3$ | OCH$_3$ | |
| J$_7$ | 0 | S | Cl | H | — | H | H | NHCH$_3$ | CH$_2$CH$_3$ | |
| J$_7$ | 0 | S | CH$_3$ | H | — | H | H | CH$_3$ | OCH$_3$ | |
| J$_7$ | 0 | SO$_2$ | H | H | — | H | H | OCH$_3$ | OCH$_3$ | |
| J$_7$ | 0 | SO$_2$ | H | H | — | H | H | CH$_3$ | OCH$_3$ | |
| J$_7$ | 0 | SO$_2$ | H | H | — | H | H | OCH$_3$ | OCH$_3$ | |
| J$_7$ | 0 | SO$_2$ | H | H | — | H | CH$_3$ | NHCH$_3$ | CH$_2$CH$_3$ | |
| J$_7$ | 0 | SO$_2$ | H | Cl | — | H | H | CH$_3$ | OCH$_3$ | |
| J$_7$ | 0 | SO$_2$ | H | CH$_3$ | — | H | H | OCH$_3$ | OCH$_3$ | |
| J$_7$ | 0 | SO$_2$ | H | OCH$_3$ | — | H | H | NHCH$_3$ | CH$_2$CH$_3$ | |
| J$_7$ | 0 | SO$_2$ | Cl | H | — | H | H | CH$_3$ | OCH$_3$ | |
| J$_7$ | 0 | SO$_2$ | OCH$_3$ | H | — | H | H | OCH$_3$ | OCH$_3$ | |
| J$_7$ | 0 | NH | H | H | — | H | H | NHCH$_3$ | CH$_2$CH$_3$ | |
| J$_7$ | 0 | NH | H | H | — | H | H | CH$_3$ | OCH$_3$ | |
| J$_7$ | 0 | NH | H | H | — | H | CH$_3$ | OCH$_3$ | OCH$_3$ | |
| J$_7$ | 0 | NCH$_3$ | H | H | — | H | H | NHCH$_3$ | CH$_2$CH$_3$ | |
| J$_7$ | 0 | NCH$_3$ | H | H | — | H | H | CH$_3$ | OCH$_3$ | |
| J$_7$ | 0 | NCH$_3$ | H | H | — | H | CH$_3$ | OCH$_3$ | OCH$_3$ | |
| J$_7$ | 1 | O | H | H | — | H | H | NHCH$_3$ | CH$_2$CH$_3$ | |
| J$_7$ | 1 | O | H | H | — | H | H | CH$_3$ | OCH$_3$ | |
| J$_7$ | 1 | O | H | H | — | H | H | OCH$_3$ | OCH$_3$ | |
| J$_7$ | 1 | O | H | H | — | H | CH$_3$ | NHCH$_3$ | CH$_2$CH$_3$ | |
| J$_7$ | 1 | O | H | H | — | CH$_3$ | CH$_3$ | CH$_3$ | OCH$_3$ | |
| J$_7$ | 1 | S | H | H | — | H | H | OCH$_3$ | OCH$_3$ | |
| J$_7$ | 1 | S | H | H | — | H | CH$_3$ | NHCH$_3$ | CH$_2$CH$_3$ | |
| J$_7$ | 1 | SO$_2$ | H | H | — | H | H | CH$_3$ | OCH$_3$ | |
| J$_7$ | 1 | SO$_2$ | H | H | — | H | H | OCH$_3$ | OCH$_3$ | |
| J$_7$ | 1 | SO$_2$ | H | H | — | H | CH$_3$ | NHCH$_3$ | CH$_2$CH$_3$ | |
| J$_7$ | 1 | SO$_2$ | H | H | — | CH$_3$ | CH$_3$ | CH$_3$ | OCH$_3$ | |
| J$_7$ | 1 | NH | H | H | — | H | H | OCH$_3$ | OCH$_3$ | |
| J$_7$ | 1 | NCH$_3$ | H | H | — | H | H | NHCH$_3$ | CH$_2$CH$_3$ | |
| J$_8$ | 0 | O | H | — | H | H | H | CH$_3$ | CH$_3$ | |
| J$_8$ | 0 | O | H | — | H | H | H | CH$_3$ | OCH$_3$ | |
| J$_8$ | 0 | O | H | — | H | H | H | OCH$_3$ | OCH$_3$ | |
| J$_8$ | 0 | O | H | — | H | H | H | NHCH$_3$ | CH$_2$CH$_3$ | |
| J$_8$ | 0 | O | H | — | H | H | CH$_3$ | CH$_3$ | OCH$_3$ | |
| J$_8$ | 0 | O | H | — | H | CH$_3$ | CH$_3$ | OCH$_3$ | OCH$_3$ | |
| J$_8$ | 0 | O | H | — | Cl | H | H | NHCH$_3$ | CH$_2$CH$_3$ | |
| J$_8$ | 0 | O | H | — | OCH$_3$ | H | H | CH$_3$ | OCH$_3$ | |
| J$_8$ | 0 | O | H | — | CH$_3$ | H | H | OCH$_3$ | OCH$_3$ | |
| J$_8$ | 0 | O | Cl | — | H | H | H | NHCH$_3$ | CH$_2$CH$_3$ | |
| J$_8$ | 0 | O | CH | — | H | H | H | CH$_3$ | OCH$_3$ | |
| J$_8$ | 0 | S | H | — | H | H | H | OCH$_3$ | OCH$_3$ | |
| J$_8$ | 0 | S | H | — | H | H | H | NHCH$_3$ | CH$_2$CH$_3$ | |
| J$_8$ | 0 | SO$_2$ | H | — | H | H | H | CH$_3$ | OCH$_3$ | |
| J$_8$ | 0 | SO$_2$ | H | — | H | H | H | OCH$_3$ | OCH$_3$ | |
| J$_8$ | 0 | SO$_2$ | H | — | H | H | H | NHCH$_3$ | CH$_2$CH$_3$ | |
| J$_8$ | 0 | SO$_2$ | H | — | H | H | CH$_3$ | CH$_3$ | OCH$_3$ | |
| J$_8$ | 0 | SO$_2$ | H | — | H | H | CH$_3$ | OCH$_3$ | OCH$_3$ | |
| J$_8$ | 0 | SO$_2$ | H | — | H | H | CH$_2$ | NHCH$_3$ | CH$_2$CH$_3$ | |
| J$_8$ | 0 | SO$_2$ | H | — | H | CH$_3$ | CH$_3$ | OCH$_3$ | OCH$_3$ | |
| J$_8$ | 0 | NH | H | — | H | H | H | OCH$_3$ | OCH$_3$ | |

TABLE 3a-continued

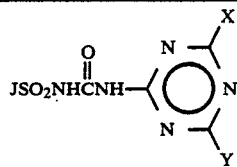

| J | q | Q₁ | R₁ | R₂ | R₃ | R₁₇ | R₁₈ | X | Y | m.p. (°C) |
|---|---|---|---|---|---|---|---|---|---|---|
| J₈ | 0 | NCH₃ | H | — | H | H | H | NHCH₃ | CH₂CH₃ | |
| J₈ | 0 | NCH₃ | H | — | H | H | H | CH₃ | OCH₃ | |
| J₈ | 1 | O | H | — | H | H | H | CH₃ | CH₃ | |
| J₈ | 1 | O | H | — | H | H | H | CH₃ | OCH₃ | |
| J₈ | 1 | O | H | — | H | H | H | OCH₃ | OCH₃ | |
| J₈ | 1 | O | H | — | H | H | H | NHCH₃ | CH₂CH₃ | |
| J₈ | 1 | O | H | — | H | H | CH₃ | CH₃ | OCH₃ | |
| J₈ | 1 | S | H | — | H | H | H | OCH₃ | OCH₃ | |
| J₈ | 1 | SO | H | — | H | H | H | NHCH₃ | CH₂CH₃ | |
| J₈ | 1 | SO₂ | H | — | H | H | H | CH₃ | OCH₃ | |
| J₈ | 1 | SO₂ | H | — | H | H | CH₃ | OCH₃ | OCH₃ | |
| J₈ | 1 | NH | H | — | H | H | H | NHCH₃ | CH₂CH₃ | |
| J₈ | 1 | NCH₃ | H | — | H | H | H | CH₃ | OCH₃ | |
| J₈ | 1 | NCH₃ | H | — | H | H | CH₃ | OCH₃ | OCH₃ | |

TABLE 4

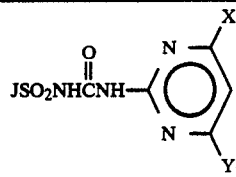

| J | q | R₁ | R₂ | R₃ | R₁₉ | R₂₀ | X | Y | m.p. (°C) |
|---|---|---|---|---|---|---|---|---|---|
| J₉ | 0 | H | H | — | H | H | CH₃ | CH₃ | |
| J₉ | 0 | H | H | — | H | H | CH₃ | OCH₃ | |
| J₉ | 0 | H | H | — | H | H | OCH₃ | OCH₃ | |
| J₉ | 0 | H | H | — | Cl | Cl | CH₃ | OCH₃ | |
| J₉ | 0 | H | H | — | Cl | Cl | OCH₃ | OCH₃ | |
| J₉ | 0 | H | H | — | Cl | Cl | Cl | OCH₃ | |
| J₉ | 0 | H | H | — | CH₃ | CH₃ | CH₃ | OCH₃ | |
| J₉ | 0 | H | H | — | CH₃ | CH₃ | OCH₃ | OCH₃ | |
| J₉ | 1 | H | H | — | H | H | Cl | OCH₃ | |
| J₉ | 1 | H | H | — | Cl | Cl | CH₃ | OCH₃ | |
| J₉ | 1 | H | H | — | CH₃ | CH₃ | OCH₃ | OCH₃ | |
| J₁₀ | 0 | H | — | H | H | H | Cl | OCH₃ | |
| J₁₀ | 0 | H | — | H | H | H | CH | OCH₃ | |
| J₁₀ | 0 | H | — | H | H | H | OCH₃ | OCH₃ | |
| J₁₀ | 0 | H | — | H | Cl | Cl | Cl | OCH₃ | |
| J₁₀ | 0 | H | — | H | Cl | Cl | CH₃ | OCH₃ | |
| J₁₀ | 0 | H | — | H | Cl | Cl | OCH₃ | OCH₃ | |
| J₁₀ | 0 | H | — | H | CH₃ | CH₃ | Cl | OCH₃ | |
| J₁₀ | 1 | H | — | H | H | H | CH₃ | OCH₃ | |
| J₁₀ | 1 | H | — | H | Cl | Cl | OCH₃ | OCH₃ | |
| J₁₀ | 1 | H | — | H | CH₃ | CH₃ | Cl | OCH₃ | |

TABLE 4a

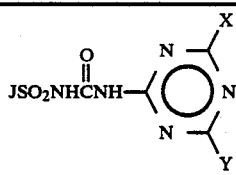

| J | q | R₁ | R₂ | R₃ | R₁₉ | R₂₀ | X | Y | m.p. (°C) |
|---|---|---|---|---|---|---|---|---|---|
| J₉ | 0 | H | H | — | H | H | CH₃ | CH₃ | |
| J₉ | 0 | H | H | — | H | H | CH₃ | OCH₃ | |
| J₉ | 0 | H | H | — | H | H | OCH₃ | OCH₃ | |
| J₉ | 0 | H | H | — | H | H | NHCH₃ | CH₂CH₃ | |
| J₉ | 0 | H | H | — | Cl | Cl | CH₃ | OCH₃ | |
| J₉ | 0 | H | H | — | Cl | Cl | OCH₃ | OCH₃ | |
| J₉ | 0 | H | H | — | Cl | Cl | NHCH₃ | CH₂CH₃ | |

TABLE 4a-continued

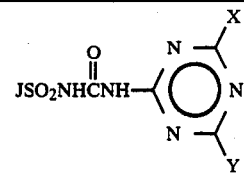

| J | q | R₁ | R₂ | R₃ | R₁₉ | R₂₀ | X | Y | m.p. (°C) |
|---|---|---|---|---|---|---|---|---|---|
| J₉ | 0 | H | H | — | CH₃ | CH₃ | CH₃ | OCH₃ | |
| J₉ | 0 | H | H | — | CH₃ | CH₃ | OCH₃ | OCH₃ | |
| J₉ | 1 | H | H | — | H | H | NHCH₃ | CH₂CH₃ | |
| J₉ | 1 | H | H | — | Cl | Cl | CH₃ | OCH₃ | |
| J₉ | 1 | H | H | — | CH₃ | CH₃ | OCH₃ | OCH₃ | |
| J₁₀ | 0 | H | — | H | H | H | NHCH₃ | CH₂CH₃ | |
| J₁₀ | 0 | H | — | H | H | H | CH₃ | OCH₃ | |
| J₁₀ | 0 | H | — | H | H | H | OCH₃ | OCH₃ | |
| J₁₀ | 0 | H | — | H | Cl | Cl | NHCH₃ | CH₂CH₃ | |
| J₁₀ | 0 | H | — | H | Cl | Cl | CH₃ | OCH₃ | |
| J₁₀ | 0 | H | — | H | Cl | Cl | OCH₃ | OCH₃ | |
| J₁₀ | 0 | H | — | H | CH₃ | CH₃ | NHCH₃ | CH₂CH₃ | |
| J₁₀ | 1 | H | — | H | H | H | CH₃ | OCH₃ | |
| J₁₀ | 1 | H | — | H | Cl | Cl | OCH₃ | OCH₃ | |
| J₁₀ | 1 | H | — | H | CH₃ | CH₃ | NHCH₃ | CH₂CH₃ | |

TABLE 5

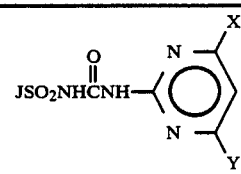

| J | R₁ | R₂ | R₃ | R₅ | R₆ | X | Y | m.p. (°C) |
|---|---|---|---|---|---|---|---|---|
| J₁₁ | H | H | — | H | H | CH₃ | OCH₃ | |
| J₁₁ | H | CH₃ | — | H | H | OCH₃ | OCH₃ | |
| J₁₁ | H | H | — | H | Cl | CH₃ | OCH₃ | |
| J₁₁ | H | Cl | — | H | CH₃ | CH₃ | CH₃ | |
| J₁₁ | CH₃ | H | — | H | C₂H₅ | CH₃ | OCH₃ | |
| J₁₁ | H | H | — | H | n-C₃H₇ | OCH₃ | OCH₃ | |
| J₁₁ | H | H | — | H | n-C₄H₉ | Cl | OCH₃ | |
| J₁₁ | H | H | — | CH₃ | H | CH₃ | OCH₃ | |
| J₁₁ | H | H | — | CH₃ | CH₃ | OCH₃ | OCH₃ | |
| J₁₂ | H | — | H | H | H | Cl | OCH₃ | |
| J₁₂ | Cl | — | Cl | H | H | CH₃ | OCH₃ | |
| J₁₂ | H | — | H | H | H | CH₃ | OCH₃ | OCH₃ |
| J₁₂ | H | — | H | H | H | CH₃ | CH₃ | CH₃ |

TABLE 5-continued

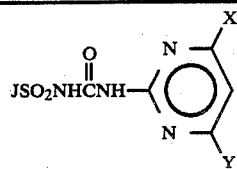

| J | R$_1$ | R$_2$ | R$_3$ | R$_5$ | R$_6$ | X | Y | m.p. (°C.) |
|---|---|---|---|---|---|---|---|---|
| J$_{12}$ | H | — | H | H | C$_2$H$_5$ | CH$_3$ | OCH$_3$ | |
| J$_{12}$ | H | — | H | H | n-C$_3$H$_7$ | OCH$_3$ | OCH$_3$ | |
| J$_{12}$ | H | — | H | H | n-C$_4$H$_9$ | Cl | OCH$_3$ | |
| J$_{12}$ | H | — | H | CH$_3$ | H | CH$_3$ | OCH$_3$ | |
| J$_{12}$ | H | — | H | CH$_3$ | CH$_3$ | OCH$_3$ | OCH$_3$ | |
| J$_{26}$ | H | H | — | CH$_3$ | — | OCH$_3$ | OCH$_3$ | |
| J$_{26}$ | H | H | — | CH$_3$ | — | OCH$_3$ | CH$_3$ | |
| J$_{26}$ | H | H | — | CH$_3$ | — | OCH$_3$ | Cl | |
| J$_{26}$ | H | H | — | CH$_3$ | — | CH$_3$ | CH$_3$ | |
| J$_{26}$ | H | H | — | H | — | OCH$_3$ | OCH$_3$ | |
| J$_{26}$ | H | H | — | H | — | OCH$_3$ | CH$_3$ | |
| J$_{26}$ | H | Cl | — | CH$_3$ | — | OCH$_3$ | OCH$_3$ | |
| J$_{27}$ | H | — | H | CH$_3$ | — | OCH$_3$ | OCH$_3$ | |
| J$_{27}$ | H | — | H | CH$_3$ | — | OCH$_3$ | CH$_3$ | |
| J$_{27}$ | H | — | H | CH$_3$ | — | OCH$_3$ | Cl | |
| J$_{27}$ | H | — | H | CH$_3$ | — | CH$_3$ | CH$_3$ | |
| J$_{27}$ | H | — | H | H | — | OCH$_3$ | OCH$_3$ | |
| J$_{27}$ | H | — | H | H | — | OCH$_3$ | CH$_3$ | |
| J$_{27}$ | H | — | Cl | CH$_3$ | — | OCH$_3$ | OCH$_3$ | |
| J$_{28}$ | H | H | — | CH$_3$ | — | OCH$_3$ | OCH$_3$ | |
| J$_{28}$ | H | H | — | CH$_3$ | — | OCH$_3$ | CH$_3$ | |
| J$_{28}$ | H | H | — | CH$_3$ | — | OCH$_3$ | Cl | |
| J$_{28}$ | H | H | — | CH$_3$ | — | CH$_3$ | CH$_3$ | |
| J$_{28}$ | H | H | — | H | — | OCH$_3$ | OCH$_3$ | |
| J$_{28}$ | H | H | — | H | — | OCH$_3$ | CH$_3$ | |
| J$_{28}$ | H | Cl | — | CH$_3$ | — | OCH$_3$ | OCH$_3$ | |
| J$_{29}$ | H | — | H | CH$_3$ | — | OCH$_3$ | OCH$_3$ | |
| J$_{29}$ | H | — | H | CH$_3$ | — | OCH$_3$ | CH$_3$ | |
| J$_{29}$ | H | — | H | CH$_3$ | — | OCH$_3$ | Cl | |
| J$_{29}$ | H | — | H | CH$_3$ | — | CH$_3$ | CH$_3$ | |
| J$_{29}$ | H | — | H | H | — | OCH$_3$ | OCH$_3$ | |
| J$_{29}$ | H | — | H | H | — | OCH$_3$ | CH$_3$ | |
| J$_{29}$ | H | — | Cl | CH$_3$ | — | OCH$_3$ | OCH$_3$ | |

TABLE 5a

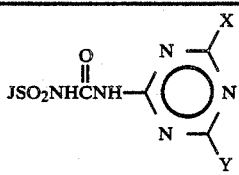

| J | R$_1$ | R$_2$ | R$_3$ | R$_5$ | R$_6$ | X | Y | m.p. (°C.) |
|---|---|---|---|---|---|---|---|---|
| J$_{11}$ | H | H | — | H | H | CH$_3$ | OCH$_3$ | |
| J$_{11}$ | H | CH$_3$ | — | H | H | OCH$_3$ | OCH$_3$ | |
| J$_{11}$ | H | H | — | H | CH$_3$ | NHCH$_3$ | CH$_2$CH$_3$ | |
| J$_{11}$ | H | Cl | — | H | CH$_3$ | CH$_3$ | CH$_3$ | |
| J$_{11}$ | CH$_3$ | H | — | H | C$_2$H$_5$ | CH$_3$ | OCH$_3$ | |
| J$_{11}$ | H | H | — | H | n-C$_3$H$_7$ | OCH$_3$ | OCH$_3$ | |
| J$_{11}$ | H | H | — | H | n-C$_4$H$_9$ | NHCH$_3$ | CH$_2$CH$_3$ | |
| J$_{11}$ | H | H | — | CH$_3$ | H | CH$_3$ | OCH$_3$ | |
| J$_{11}$ | H | H | — | CH$_3$ | CH$_3$ | OCH$_3$ | OCH$_3$ | |
| J$_{12}$ | H | — | H | H | H | NHCH$_3$ | CH$_2$CH$_3$ | |
| J$_{12}$ | Cl | — | Cl | H | H | CH$_3$ | OCH$_3$ | |
| J$_{12}$ | H | — | H | H | CH$_3$ | OCH$_3$ | OCH$_3$ | |
| J$_{12}$ | H | — | H | H | CH$_3$ | CH$_3$ | CH$_3$ | |
| J$_{12}$ | H | — | H | H | C$_2$H$_5$ | CH$_3$ | OCH$_3$ | |
| J$_{12}$ | H | — | H | H | n-C$_3$H$_7$ | OCH$_3$ | OCH$_3$ | |
| J$_{12}$ | H | — | H | H | n-C$_4$H$_9$ | NHCH$_3$ | CH$_2$CH$_3$ | |
| J$_{12}$ | H | — | H | CH$_3$ | H | CH$_3$ | OCH$_3$ | |
| J$_{12}$ | H | — | H | CH$_3$ | CH$_3$ | OCH$_3$ | OCH$_3$ | |
| J$_{26}$ | H | H | — | CH$_3$ | — | OCH$_3$ | OCH$_3$ | |
| J$_{26}$ | H | H | — | CH$_3$ | — | OCH$_3$ | CH$_3$ | |
| J$_{26}$ | H | H | — | CH$_3$ | — | CH$_3$ | CH$_3$ | |
| J$_{26}$ | H | H | — | H | — | OCH$_3$ | OCH$_3$ | |
| J$_{26}$ | H | H | — | H | — | OCH$_3$ | CH$_3$ | |

TABLE 5a-continued

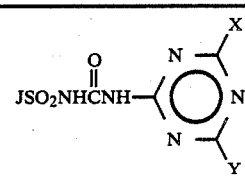

| J | R$_1$ | R$_2$ | R$_3$ | R$_5$ | R$_6$ | X | Y | m.p. (°C.) |
|---|---|---|---|---|---|---|---|---|
| J$_{26}$ | H | Cl | — | CH$_3$ | — | OCH$_3$ | OCH$_3$ | |
| J$_{26}$ | Cl | H | — | CH$_3$ | — | OCH$_3$ | OCH$_3$ | |
| J$_{27}$ | H | — | H | CH$_3$ | — | OCH$_3$ | OCH$_3$ | |
| J$_{27}$ | H | — | H | CH$_3$ | — | OCH$_3$ | CH$_3$ | |
| J$_{27}$ | H | — | H | CH$_3$ | — | CH$_3$ | CH$_3$ | |
| J$_{27}$ | H | — | H | H | — | OCH$_3$ | OCH$_3$ | |
| J$_{27}$ | H | — | H | H | — | OCH$_3$ | CH$_3$ | |
| J$_{27}$ | H | — | Cl | CH$_3$ | — | OCH$_3$ | OCH$_3$ | |
| J$_{27}$ | Cl | — | H | CH$_3$ | — | OCH$_3$ | OCH$_3$ | |
| J$_{28}$ | H | H | — | CH$_3$ | — | OCH$_3$ | OCH$_3$ | |
| J$_{28}$ | H | H | — | CH$_3$ | — | OCH$_3$ | CH$_3$ | |
| J$_{28}$ | H | H | — | CH$_3$ | — | CH$_3$ | CH$_3$ | |
| J$_{28}$ | H | H | — | H | — | OCH$_3$ | OCH$_3$ | |
| J$_{28}$ | H | H | — | H | — | OCH$_3$ | CH$_3$ | |
| J$_{28}$ | H | Cl | — | CH$_3$ | — | OCH$_3$ | OCH$_3$ | |
| J$_{28}$ | Cl | H | — | CH$_3$ | — | OCH$_3$ | OCH$_3$ | |
| J$_{29}$ | H | — | H | CH$_3$ | — | OCH$_3$ | OCH$_3$ | |
| J$_{29}$ | H | — | H | CH$_3$ | — | CH$_3$ | CH$_3$ | |
| J$_{29}$ | H | — | H | H | — | OCH$_3$ | OCH$_3$ | |
| J$_{29}$ | H | — | H | H | — | OCH$_3$ | CH$_3$ | |
| J$_{29}$ | H | — | Cl | CH$_3$ | — | OCH$_3$ | OCH$_3$ | |
| J$_{29}$ | Cl | — | H | CH$_3$ | — | OCH$_3$ | OCH$_3$ | |

TABLE 6

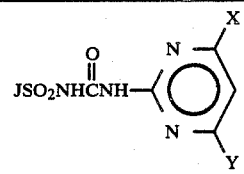

| J | q | Q$_1$ | R$_1$ | R$_2$ | R$_3$ | R$_7$ | X | Y | m.p. (°C.) |
|---|---|---|---|---|---|---|---|---|---|
| J$_{13}$ | 0 | O | H | H | — | H | CH$_3$ | OCH$_3$ | |
| J$_{13}$ | 0 | O | H | Cl | — | H | OCH$_3$ | OCH$_3$ | |
| J$_{13}$ | 0 | O | H | H | — | CH$_3$ | Cl | OCH$_3$ | |
| J$_{13}$ | 1 | O | H | H | — | H | CH$_3$ | OCH$_3$ | |
| J$_{13}$ | 1 | O | H | H | — | CH$_3$ | OCH$_3$ | OCH$_3$ | |
| J$_{13}$ | 1 | O | CH$_3$ | H | — | H | Cl | OCH$_3$ | |
| J$_{13}$ | 0 | S | H | H | — | H | CH$_3$ | CH$_3$ | |
| J$_{13}$ | 0 | SO | H | H | — | H | CH$_3$ | OCH$_3$ | |
| J$_{13}$ | 0 | SO$_2$ | H | H | — | H | OCH$_3$ | OCH$_3$ | |
| J$_{13}$ | 0 | S | H | H | — | H | CH$_3$ | Cl | |
| J$_{13}$ | 1 | SO | H | H | — | H | CH$_3$ | OCH$_3$ | |
| J$_{13}$ | 1 | SO$_2$ | H | H | — | H | OCH$_3$ | OCH$_3$ | |
| J$_{13}$ | 1 | NH | H | H | — | H | CH$_3$ | Cl | |
| J$_{13}$ | 1 | NCH$_3$ | H | H | — | H | CH$_3$ | OCH$_3$ | |
| J$_{13}$ | 1 | NH | H | H | — | H | OCH$_3$ | OCH$_3$ | |
| J$_{13}$ | 1 | NCH$_3$ | H | H | — | H | CH$_3$ | Cl | |
| J$_{14}$ | 0 | O | H | — | H | H | CH$_3$ | OCH$_3$ | |
| J$_{14}$ | 0 | O | H | — | H | H | OCH$_3$ | OCH$_3$ | |
| J$_{14}$ | 1 | O | H | — | H | CH$_3$ | Cl | OCH$_3$ | |
| J$_{14}$ | 1 | O | Cl | — | Cl | H | CH$_3$ | OCH$_3$ | |
| J$_{14}$ | 0 | S | H | — | H | H | OCH$_3$ | OCH$_3$ | |
| J$_{14}$ | 0 | SO$_2$ | H | — | H | H | CH$_3$ | OCH$_3$ | |
| J$_{14}$ | 1 | S | H | — | H | H | CH$_3$ | CH$_3$ | |
| J$_{14}$ | 1 | SO$_2$ | H | — | H | H | OCH$_3$ | OCH$_3$ | |
| J$_{14}$ | 0 | NCH$_3$ | H | — | H | H | Cl | OCH$_3$ | |

TABLE 6a

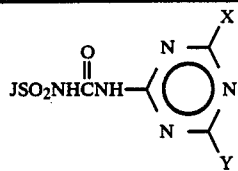

| J | q | Q₁ | R₁ | R₂ | R₃ | R₇ | X | Y | m.p. (°C.) |
|---|---|---|---|---|---|---|---|---|---|
| $J_{13}$ | 0 | O | H | H | — | H | CH₃ | OCH₃ | |
| $J_{13}$ | 0 | O | H | Cl | — | H | OCH₃ | OCH₃ | |
| $J_{13}$ | 0 | O | H | H | — | CH₃ | NHCH₃ | CH₂CH₃ | |
| $J_{13}$ | 1 | O | H | H | — | H | CH₃ | OCH₃ | |
| $J_{13}$ | 1 | O | H | H | — | CH₃ | OCH₃ | OCH₃ | |
| $J_{13}$ | 1 | O | CH₃ | H | — | H | NHCH₃ | CH₂CH₃ | |
| $J_{13}$ | 0 | S | H | H | — | H | CH₃ | CH₃ | |
| $J_{13}$ | 0 | SO | H | H | — | H | CH₃ | OCH₃ | |
| $J_{13}$ | 0 | SO₂ | H | H | — | H | OCH₃ | OCH₃ | |
| $J_{13}$ | 0 | S | H | H | — | H | NHCH₃ | CH₂CH₃ | |
| $J_{13}$ | 1 | SO | H | H | — | H | CH₃ | OCH₃ | |
| $J_{13}$ | 1 | SO₂ | H | H | — | H | OCH₃ | OCH₃ | |
| $J_{13}$ | 1 | NH | H | H | — | H | NHCH₃ | CH₂CH₃ | |
| $J_{13}$ | 1 | NCH₃ | H | H | — | H | CH₃ | OCH₃ | |
| $J_{13}$ | 1 | NH | H | H | — | H | OCH₃ | OCH₃ | |
| $J_{13}$ | 1 | NCH₃ | H | H | — | H | NHCH₃ | CH₂CH₃ | |
| $J_{14}$ | 0 | O | H | — | H | H | CH₃ | OCH₃ | |
| $J_{14}$ | 0 | O | H | — | H | H | OCH₃ | OCH₃ | |
| $J_{14}$ | 1 | O | H | — | H | CH₃ | NHCH₃ | CH₂CH₃ | |
| $J_{14}$ | 1 | O | Cl | — | Cl | H | CH₃ | OCH₃ | |
| $J_{14}$ | 0 | S | H | — | H | H | OCH₃ | OCH₃ | |
| $J_{14}$ | 0 | SO₂ | H | — | H | H | NHCH₃ | CH₂CH₃ | |
| $J_{14}$ | 1 | S | H | — | H | H | CH₃ | OCH₃ | |
| $J_{14}$ | 1 | SO₂ | H | — | H | H | OCH₃ | OCH₃ | |
| $J_{14}$ | 0 | NCH₃ | H | — | H | H | NHCH₃ | CH₂CH₃ | |

TABLE 7

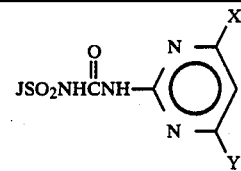

| J | q | R₁ | R₂ | R₃ | R₂₁ | R₂₂ | X | Y | m.p. (°C.) |
|---|---|---|---|---|---|---|---|---|---|
| $J_{15}$ | 0 | H | H | — | H | H | CH₃ | OCH₃ | |
| $J_{15}$ | 0 | H | H | — | H | CH₃ | OCH₃ | OCH₃ | |
| $J_{15}$ | 0 | H | H | — | CH₃ | CH₃ | Cl | OCH₃ | |
| $J_{15}$ | 1 | H | Cl | — | H | H | CH₃ | OCH₃ | |
| $J_{15}$ | 0 | H | CH₃ | — | H | H | OCH₃ | OCH₃ | |
| $J_{15}$ | 0 | H | OCH₃ | — | H | H | Cl | OCH₃ | |
| $J_{15}$ | 0 | Cl | H | — | H | H | CH₃ | OCH₃ | |
| $J_{15}$ | 0 | CH₃ | H | — | H | H | OCH₃ | OCH₃ | |
| $J_{16}$ | 0 | H | — | H | H | H | Cl | OCH₃ | |
| $J_{16}$ | 0 | H | — | H | H | CH₃ | CH₃ | CH₃ | |
| $J_{16}$ | 0 | H | — | H | CH₃ | CH₃ | CH₃ | OCH₃ | |
| $J_{16}$ | 1 | H | — | H | H | H | Cl | OCH₃ | |

TABLE 7a

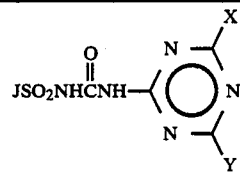

| J | q | R₁ | R₂ | R₃ | R₂₁ | R₂₂ | X | Y | m.p. (°C.) |
|---|---|---|---|---|---|---|---|---|---|
| $J_{15}$ | 0 | H | H | — | H | H | CH₃ | OCH₃ | |
| $J_{15}$ | 0 | H | H | — | H | CH₃ | OCH₃ | OCH₃ | |
| $J_{15}$ | 0 | H | H | — | CH₃ | CH₃ | NHCH₃ | CH₂CH₃ | |
| $J_{15}$ | 1 | H | Cl | — | H | H | CH₃ | OCH₃ | |
| $J_{15}$ | 0 | H | CH₃ | — | H | H | OCH₃ | OCH₃ | |
| $J_{15}$ | 0 | H | OCH₃ | — | H | H | NHCH₃ | CH₂CH₃ | |
| $J_{15}$ | 0 | Cl | H | — | H | H | CH₃ | OCH₃ | |
| $J_{15}$ | 0 | CH₃ | H | — | H | H | OCH₃ | OCH₃ | |
| $J_{16}$ | 0 | H | — | H | H | H | NHCH₃ | CH₂CH₃ | |
| $J_{16}$ | 0 | H | — | H | H | CH₃ | CH₃ | CH₃ | |
| $J_{16}$ | 0 | H | — | H | CH₃ | CH₃ | CH₃ | OCH₃ | |
| $J_{16}$ | 1 | H | — | H | H | H | NHCH₃ | CH₂CH₃ | |

TABLE 8

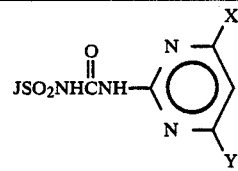

| J | Q₂ | Q₃ | R₁ | R₂ | R₃ | R₇ | X | Y | m.p. (°C.) |
|---|---|---|---|---|---|---|---|---|---|
| $J_{19}$ | O | — | H | H | — | H | CH₃ | OCH₃ | |
| $J_{19}$ | O | — | H | H | — | H | OCH₃ | OCH₃ | |
| $J_{19}$ | O | — | H | H | — | CH₃ | Cl | OCH₃ | |
| $J_{19}$ | O | — | H | Cl | — | H | CH₃ | OCH₃ | |
| $J_{19}$ | S | — | H | H | — | H | OCH₃ | OCH₃ | 183–186(d) |
| $J_{19}$ | S | — | H | H | — | H | Cl | OCH₃ | 169–173(d) |
| $J_{19}$ | S | — | H | H | — | CH₃ | CH₃ | OCH₃ | |
| $J_{19}$ | S | — | Cl | H | — | H | OCH₃ | OCH₃ | |
| $J_{19}$ | S | — | H | H | — | H | CH₃ | CH₃ | 194–196(d) |
| $J_{19}$ | S | — | H | H | — | H | CH₃ | OCH₃ | 182–184(d) |
| $J_{19}$ | NH | — | H | H | — | H | Cl | OCH₃ | |
| $J_{19}$ | NCH₃ | — | H | H | — | H | CH₃ | CH₃ | |
| $J_{19}$ | NCH₃ | — | H | H | — | H | CH₃ | OCH₃ | |
| $J_{19}$ | CH₂ | — | H | H | — | H | OCH₃ | OCH₃ | |
| $J_{19}$ | CH₂ | — | H | H | — | H | Cl | OCH₃ | |
| $J_{19}$ | CHCH₃ | — | H | H | — | H | CH₃ | OCH₃ | |
| $J_{20}$ | O | — | H | — | H | H | OCH₃ | OCH₃ | |

TABLE 8-continued

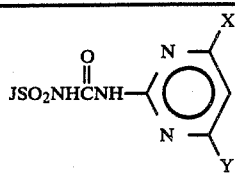

| J | Q$_2$ | Q$_3$ | R$_1$ | R$_2$ | R$_3$ | R$_7$ | X | Y | m.p. (°C.) |
|---|---|---|---|---|---|---|---|---|---|
| J$_{20}$ | O | — | H | — | H | H | Cl | OCH$_3$ | |
| J$_{20}$ | O | — | Cl | — | Cl | H | CH$_3$ | OCH$_3$ | |
| J$_{20}$ | O | — | H | — | H | CH$_3$ | OCH$_3$ | OCH$_3$ | |
| J$_{20}$ | S | — | H | — | H | H | Cl | OCH$_3$ | |
| J$_{20}$ | S | — | H | — | H | H | CH$_3$ | OCH$_3$ | |
| J$_{20}$ | S | — | H | — | H | CH$_3$ | OCH$_3$ | OCH$_3$ | |
| J$_{20}$ | S | — | Cl | — | Cl | H | Cl | OCH$_3$ | |
| J$_{20}$ | NH | — | H | — | H | H | CH$_3$ | OCH$_3$ | |
| J$_{20}$ | NCH$_3$ | — | H | — | H | H | OCH$_3$ | OCH$_3$ | |
| J$_{20}$ | NCH$_3$ | — | H | — | H | H | Cl | OCH$_3$ | |
| J$_{21}$ | — | O | H | H | — | H | CH$_3$ | OCH$_3$ | |
| J$_{21}$ | — | O | H | H | — | CH$_3$ | OCH$_3$ | OCH$_3$ | |
| J$_{21}$ | — | O | H | CH$_3$ | — | H | OCH$_3$ | OCH$_3$ | 151–158(d) |
| J$_{21}$ | — | O | H | CH$_3$ | — | H | CH$_3$ | CH$_3$ | 186–188(d) |
| J$_{21}$ | — | O | H | CH$_3$ | — | H | Cl | OCH$_3$ | 164–167(d) |
| J$_{21}$ | — | S | H | H | — | H | Cl | OCH$_3$ | |
| J$_{21}$ | — | S | H | Cl | — | H | CH$_3$ | CH$_3$ | |
| J$_{21}$ | — | NH | H | H | — | H | CH$_3$ | OCH$_3$ | |
| J$_{21}$ | — | NCH$_3$ | Cl | H | — | H | OCH$_3$ | OCH$_3$ | |
| J$_{21}$ | — | CH$_2$ | H | H | — | H | Cl | OCH$_3$ | |
| J$_{22}$ | — | O | H | — | H | H | CH$_3$ | OCH$_3$ | |
| J$_{22}$ | — | O | H | — | H | CH$_3$ | OCH$_3$ | OCH$_3$ | |
| J$_{22}$ | — | S | H | — | H | H | Cl | OCH$_3$ | |
| J$_{22}$ | — | S | H | — | H | Cl | CH$_3$ | OCH$_3$ | |
| J$_{22}$ | — | NH | H | — | CH$_3$ | H | OCH$_3$ | OCH$_3$ | |
| J$_{22}$ | — | NCH$_3$ | H | — | H | H | Cl | OCH$_3$ | |
| J$_{22}$ | — | CH$_2$ | Cl | — | H | H | CH$_3$ | OCH$_3$ | |
| J$_{22}$ | — | CH$_2$ | H | — | H | H | OCH$_3$ | OCH$_3$ | |

TABLE 8a

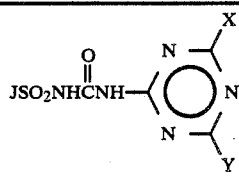

| J | Q$_2$ | Q$_3$ | R$_1$ | R$_2$ | R$_3$ | R$_7$ | X | Y | m.p. (°C.) |
|---|---|---|---|---|---|---|---|---|---|
| J$_{19}$ | O | — | H | H | — | H | CH$_3$ | OCH$_3$ | |
| J$_{19}$ | O | — | H | H | — | H | OCH$_3$ | OCH$_3$ | |
| J$_{19}$ | O | — | H | H | — | CH$_3$ | NHCH$_3$ | CH$_2$CH$_3$ | |
| J$_{19}$ | O | — | H | Cl | — | H | CH$_3$ | OCH$_3$ | |
| J$_{19}$ | S | — | H | H | — | H | OCH$_3$ | OCH$_3$ | 167–170(d) |
| J$_{19}$ | S | — | H | H | — | H | NHCH$_3$ | CH$_2$CH$_3$ | |
| J$_{19}$ | S | — | H | H | — | CH$_3$ | CH$_3$ | OCH$_3$ | |
| J$_{19}$ | S | — | Cl | H | — | H | OCH$_3$ | OCH$_3$ | |
| J$_{19}$ | S | — | H | H | — | H | OCH$_3$ | CH$_3$ | 152–156(d) |
| J$_{19}$ | NH | — | H | H | — | H | NHCH$_3$ | CH$_2$CH$_3$ | |
| J$_{19}$ | NCH$_3$ | — | H | H | — | H | CH$_3$ | CH$_3$ | |
| J$_{19}$ | NCH$_3$ | — | H | H | — | H | CH$_3$ | OCH$_3$ | |
| J$_{19}$ | CH$_2$ | — | H | H | — | H | OCH$_3$ | OCH$_3$ | |
| J$_{19}$ | CH$_2$ | — | H | H | — | H | NHCH$_3$ | CH$_2$CH$_3$ | |
| J$_{19}$ | CHCH$_3$ | — | H | H | — | H | CH$_3$ | OCH$_3$ | |
| J$_{20}$ | O | — | H | — | H | H | OCH$_3$ | OCH$_3$ | |
| J$_{20}$ | O | — | H | — | H | H | NHCH$_3$ | CH$_2$CH$_3$ | |
| J$_{20}$ | O | — | Cl | — | Cl | H | OCH$_3$ | OCH$_3$ | |
| J$_{20}$ | O | — | H | — | H | CH$_3$ | OCH$_3$ | OCH$_3$ | |
| J$_{20}$ | S | — | H | — | H | H | NHCH$_3$ | CH$_2$CH$_3$ | |
| J$_{20}$ | S | — | H | — | H | H | CH$_3$ | OCH$_3$ | |
| J$_{20}$ | S | — | H | — | H | CH$_3$ | OCH$_3$ | OCH$_3$ | |
| J$_{20}$ | S | — | Cl | — | Cl | H | NHCH$_3$ | CH$_2$CH$_3$ | |
| J$_{20}$ | NH | — | H | — | H | H | CH$_3$ | OCH$_3$ | |
| J$_{20}$ | NCH$_3$ | — | H | — | H | H | OCH$_3$ | OCH$_3$ | |
| J$_{20}$ | NCH$_3$ | — | H | — | H | H | NHCH$_3$ | CH$_2$CH$_3$ | |
| J$_{21}$ | — | O | H | H | — | H | CH$_3$ | OCH$_3$ | |
| J$_{21}$ | — | O | H | H | — | CH$_3$ | OCH$_3$ | OCH$_3$ | |
| J$_{21}$ | — | O | H | CH$_3$ | — | H | OCH$_3$ | OCH$_3$ | 151–157(d) |

TABLE 8a-continued

JSO₂NHCNH— [pyrimidine with X, Y substituents, N ring]

| J | Q₂ | Q₃ | R₁ | R₂ | R₃ | R₇ | X | Y | m.p. (°C.) |
|---|---|---|---|---|---|---|---|---|---|
| J₂₁ | — | O | H | CH₃ | — | H | OCH₃ | CH₃ | 167-172(d) |
| J₂₁ | — | S | H | H | — | H | NHCH₃ | CH₂CH₃ | |
| J₂₁ | — | S | H | Cl | — | H | CH₃ | CH₃ | |
| J₂₁ | — | NH | H | H | — | H | CH₃ | OCH₃ | |
| J₂₁ | — | NCH₃ | Cl | H | — | H | OCH₃ | OCH₃ | |
| J₂₁ | — | CH₂ | H | H | — | H | NHCH₃ | CH₂CH₃ | |
| J₂₂ | — | O | H | — | H | H | CH₃ | OCH₃ | |
| J₂₂ | — | O | H | — | H | CH₃ | OCH₃ | OCH₃ | |
| J₂₂ | — | S | H | — | H | H | NHCH₃ | CH₂CH₃ | |
| J₂₂ | — | S | H | — | H | Cl | CH₃ | OCH₃ | |
| J₂₂ | — | NH | H | — | CH₃ | H | OCH₃ | OCH₃ | |
| J₂₂ | — | NCH₃ | H | — | H | H | NHCH₃ | CH₂CH₃ | |
| J₂₂ | — | CH₂ | Cl | — | H | H | CH₃ | OCH₃ | |
| J₂₂ | — | CH₂ | H | — | H | H | OCH₃ | OCH₃ | |

TABLE 9

JSO₂NHCNH— [pyrimidine with X, Y substituents]

| J | R₁ | R₂ | R₃ | R₂₃ | X | Y | m.p. (°C.) |
|---|---|---|---|---|---|---|---|
| J₂₃ | H | H | — | H | CH₃ | OCH₃ | |
| J₂₃ | H | H | — | 8-CH₃ | OCH₃ | OCH₃ | |
| J₂₃ | H | H | — | 8-OCH₃ | Cl | OCH₃ | |
| J₂₃ | H | H | — | 8-Cl | CH₃ | OCH₃ | |
| J₂₃ | H | Cl | — | H | OCH₃ | OCH₃ | |
| J₂₃ | H | CH₃ | — | H | Cl | OCH₃ | |
| J₂₃ | Cl | H | — | H | CH₃ | OCH₃ | |
| J₂₄ | H | — | H | H | OCH₃ | OCH₃ | |
| J₂₄ | H | — | H | 5-CH₃ | Cl | OCH₃ | |
| J₂₄ | H | — | H | 5-OCH₃ | CH₃ | OCH₃ | |
| J₂₄ | H | — | H | 5-Cl | OCH₃ | OCH₃ | |
| J₂₄ | Cl | — | Cl | H | Cl | OCH₃ | |
| J₂₅ | — | H | H | H | CH₃ | OCH₃ | |

TABLE 9a

JSO₂NHCNH— [triazine with X, Y substituents]

| J | R₁ | R₂ | R₃ | R₂₃ | X | Y | m.p. (°C.) |
|---|---|---|---|---|---|---|---|
| J₂₃ | H | H | — | H | CH₃ | OCH₃ | |
| J₂₃ | H | H | — | 8-CH₃ | OCH₃ | OCH₃ | |
| J₂₃ | H | H | — | 8-OCH₃ | NHCH₃ | CH₂CH₃ | |
| J₂₃ | H | H | — | 8-Cl | CH₃ | OCH₃ | |
| J₂₃ | H | Cl | — | H | OCH₃ | OCH₃ | |
| J₂₃ | H | CH₃ | — | H | NHCH₃ | CH₂CH₃ | |
| J₂₃ | Cl | H | — | H | CH₃ | OCH₃ | |
| J₂₄ | H | — | H | H | OCH₃ | OCH₃ | |
| J₂₄ | H | — | H | 5-CH₃ | NHCH₃ | CH₂CH₃ | |
| J₂₄ | H | — | H | 5-OCH₃ | CH₃ | OCH₃ | |
| J₂₄ | H | — | H | 5-Cl | OCH₃ | OCH₃ | |
| J₂₄ | Cl | — | Cl | H | NHCH₃ | CH₂CH₃ | |
| J₂₅ | — | H | H | H | CH₃ | OCH₃ | |

TABLE 10

JSO₂NHCNH— [ring with X, Y, Z substituents]

where J₁ₐ is, J₂ₐ is, J₁ᵦ is, J₂ᵦ is, J₃ₐ is, J₄ₐ is, J₅ₐ is, J₆ₐ is [structures shown]

| J | X | Y | Z | m.p. (°C.) |
|---|---|---|---|---|
| J₁ₐ | OC₂H₅ | CH₃ | CH | |
| J₁ₐ | Br | OCH₃ | CH | |
| J₁ₐ | F | OC₂H₅ | CH | |
| J₁ₐ | I | OCH₃ | CH | |
| J₁ₐ | OCF₂H | CH₃ | CH | |

TABLE 10-continued

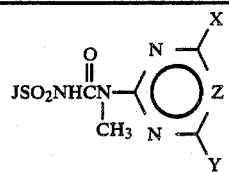

| J | | X | Y | Z |
|---|---|---|---|---|
| $J_{1a}$ | $CH_2F$ | $OCH_3$ | | CH |
| $J_{1a}$ | $CF_3$ | $OCH_3$ | | CH |
| $J_{1a}$ | $OCH_2CH_2F$ | $CH_3$ | | CH |
| $J_{1a}$ | $OCH_2CHF_2$ | $OCH_3$ | | CH |
| $J_{1a}$ | $OCH_2CF_3$ | $CH_3$ | | N |
| $J_{1a}$ | $CH_2Cl$ | $OCH_3$ | | CH |
| $J_{1a}$ | $CH_2Br$ | $OCH_3$ | | CH |
| $J_{1a}$ | $OCH_3$ | H | | CH |
| $J_{1a}$ | $CH_3$ | $OC_2H_5$ | | N |
| $J_{2a}$ | $CH_3$ | $CH_2OCH_3$ | | CH |
| $J_{2a}$ | $OCH_3$ | $NHCH_3$ | | N |
| $J_{2a}$ | $CH_3$ | $N(OCH_3)CH_3$ | | N |
| $J_{2a}$ | $C_2H_5$ | $N(CH_3)_2$ | | N |
| $J_{2a}$ | $OCH_3$ | $CH_2CH_3$ | | CH |
| $J_{3a}$ | $OCH_3$ | $CF_3$ | | CH |
| $J_{3a}$ | $OCH_3$ | $SCH_3$ | | N |
| $J_{3a}$ | $CH_3$ | $OCH_2CH=CH_2$ | | CH |
| $J_{1b}$ | $CH_3$ | $OCH_2C\equiv CH$ | | CH |
| $J_{1b}$ | $CH_3$ | $CH_2OCH_2CH_3$ | | N |
| $J_{1b}$ | $OCH_3$ | $OCH_2CH_2OCH_3$ | | CH |
| $J_{2b}$ | $OCH_3$ | $CH_2SCH_3$ | | CH |
| $J_{2b}$ | $OCH_3$ | $CH_2SCH_2CH_3$ | | CH |
| $J_{2b}$ | $CH_3$ | $C(O)H$ | | CH |
| $J_{4a}$ | $CH_3$ | $C(O)CH_3$ | | CH |
| $J_{4a}$ | $CH_3$ | $CH(OCH_3)_2$ | | CH |
| $J_{5a}$ | $CH_3$ | 1,3-dioxolan-2-yl | | CH |
| $J_{6a}$ | $CH_3$ | 4-methyl-1,3-dioxolan-2-yl | | CH |

TABLE 12

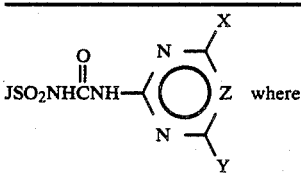

where $J_{1a}$, $J_{1b}$, $J_{2a}$, $J_{2b}$, $J_{3a}$, $J_{4a}$, $J_{5a}$ and $J_{6a}$ are as defined in Table 10.

| J | X | Y | Z | m.p. (°C.) |
|---|---|---|---|---|
| $J_{1b}$ | $CH_3$ | $CH_3$ | CH | |
| $J_{2a}$ | $CH_3$ | $OCH_3$ | CH | |
| $J_{1a}$ | $OCH_3$ | $OCH_3$ | CH | |
| $J_{2b}$ | Cl | $OCH_3$ | CH | |
| $J_{3a}$ | $CH_3$ | $CH_3$ | N | |
| $J_{4a}$ | $CH_3$ | $OCH_3$ | N | |
| $J_{5a}$ | $OCH_3$ | $OCH_3$ | N | |
| $J_{1a}$ | $NHCH_3$ | $OC_2H_5$ | N | |
| $J_{6a}$ | $CH_3$ | $OCH_3$ | CH | |

TABLE 13

 where

TABLE 11

$$JSO_2NHCNH-A$$
(with C=O)

| J | A | $X_1$ | $Y_1$ | $X_2$ | $Y_2$ | $X_3$ | $X_4$ | $Y_3$ | $Y_4$ | $Z_1$ | m.p. (°C.) |
|---|---|---|---|---|---|---|---|---|---|---|---|
| $J_{1a}$ | A-2 | $CH_3$ | O | — | — | — | — | — | — | — | |
| $J_{1a}$ | A-2 | $OCH_3$ | O | — | — | — | — | — | — | — | |
| $J_{1b}$ | A-2 | $OC_2H_5$ | O | — | — | — | — | — | — | — | |
| $J_{2a}$ | A-2 | $OCF_2H$ | O | — | — | — | — | — | — | — | |
| $J_{1a}$ | A-2 | $CH_3$ | $CH_2$ | — | — | — | — | — | — | — | |
| $J_{1a}$ | A-2 | $OCH_3$ | $CH_2$ | — | — | — | — | — | — | — | |
| $J_{2b}$ | A-3 | $CH_3$ | — | — | — | — | — | — | — | — | |
| $J_{3a}$ | A-3 | $OCH_3$ | — | — | — | — | — | — | — | — | |
| $J_{4a}$ | A-3 | $OC_2H_5$ | — | — | — | — | — | — | — | — | |
| $J_{5a}$ | A-3 | $OCF_2H$ | — | — | — | — | — | — | — | — | |
| $J_{1a}$ | A-4 | $CH_3$ | — | — | — | — | — | $CH_3$ | — | — | |
| $J_{1a}$ | A-4 | $OCH_3$ | — | — | — | — | — | $CH_3$ | — | — | |
| $J_{6a}$ | A-4 | $OC_2H_5$ | — | — | — | — | — | $CH_3$ | — | — | |
| $J_{1b}$ | A-4 | $OCF_2H$ | — | — | — | — | — | $CH_3$ | — | — | |
| $J_{2a}$ | A-4 | $CH_3$ | — | — | — | — | — | H | — | — | |
| $J_{2b}$ | A-4 | $OCH_3$ | — | — | — | — | — | H | — | — | |
| $J_{1a}$ | A-5 | — | — | $CH_3$ | $OCH_3$ | — | — | — | — | — | |
| $J_{1a}$ | A-5 | — | — | $C_2H_5$ | $OC_2H_5$ | — | — | — | — | — | |
| $J_{3a}$ | A-5 | — | — | $CH_2CF_3$ | $OCH_3$ | — | — | — | — | — | |
| $J_{4a}$ | A-5 | — | — | $CH_3$ | $SCH_3$ | — | — | — | — | — | |
| $J_{5a}$ | A-5 | — | — | $CH_3$ | $SC_2H_5$ | — | — | — | — | — | |
| $J_{6a}$ | A-5 | — | — | $CH_3$ | $OCF_2H$ | — | — | — | — | — | |
| $J_{1b}$ | A-5 | — | — | $CH_3$ | $SCF_2H$ | — | — | — | — | — | |
| $J_{1a}$ | A-5 | — | — | $CH_3$ | $CH_3$ | — | — | — | — | — | |
| $J_{1a}$ | A-5 | — | — | $CH_3$ | $C_2H_5$ | — | — | — | — | — | |
| $J_{1a}$ | A-6 | — | — | — | — | $CH_3$ | — | — | — | — | |
| $J_{1a}$ | A-6 | — | — | — | — | $OCH_3$ | — | — | — | — | |
| $J_{1a}$ | A-7 | — | — | — | — | — | $OCH_3$ | — | $OCH_3$ | CH | |
| $J_{1a}$ | A-7 | — | — | — | — | — | $CH_3$ | — | $CH_3$ | CH | |
| $J_{1b}$ | A-7 | — | — | — | — | — | $OCH_3$ | — | $CH_3$ | CH | |
| $J_{2a}$ | A-7 | — | — | — | — | — | $OCH_3$ | — | $OCH_3$ | N | |
| $J_{2a}$ | A-7 | — | — | — | — | — | $OCH_3$ | — | $OCH_3$ | CH | | where $J_{1a}$, $J_{1b}$, $J_{2a}$, $J_{2b}$, $J_{3a}$, $J_{4a}$, $J_{5a}$ and $J_{6a}$ are as defined in Table 10.

TABLE 13-continued $J_{1c}$ is: [structure: benzofuranone with methyl and N⁺–O⁻ substituents]

$J_{5b}$ is: [structure: benzofuranone with vinyl, methyl and N⁺–O⁻ substituents]

$J_{3b}$ is: [structure: benzisothiazoline-SO₂ with n-Pr on N, methyl and N⁺–O⁻ substituents]

| J | X | Y | Z | m.p. (°C.) |
|---|---|---|---|---|
| $J_{5b}$ | $CH_3$ | $CH_3$ | CH | |
| $J_{3b}$ | $CH_3$ | $OCH_3$ | CH | |
| $J_{1c}$ | $OCH_3$ | $OCH_3$ | CH | |
| $J_{1c}$ | Cl | $OCH_3$ | CH | |
| $J_{5b}$ | $CH_3$ | $CH_3$ | N | |
| $J_{3b}$ | $CH_3$ | $OCH_3$ | N | |
| $J_{1c}$ | $OCH_3$ | $OCH_3$ | N | |
| $J_{1c}$ | $NHCH_3$ | $OC_2H_5$ | N | |
| $J_{5b}$ | $OCH_3$ | $OCH_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 14

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 5

Wettable Powder

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 6

Wettable Powder

| | |
|---|---|
| 1,3-Dihydro-N—[(4-methoxy-6-methylpyrimidin-2-yl)- | 50% |

| | |
|---|---|
| aminocarbonyl]-6-methyl-3-oxofuro[3,4-c]pyridine-4-sulfonamide | |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 7

Granule

| | |
|---|---|
| Wettable Powder of Example 6 | 5% |
| attapulgite granules | 95% |

(U.S.S. 20–40 mesh; 0.84–0.42 mm)

A slurry of wettable powder containing 25% solids is sprayed on the surface of attapulgite granules in a double-cone blender. The granules are dried and packaged.

EXAMPLE 8

Extruded Pellet

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

Low Strength Granule

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 0.1% |
| attapulgite granules | 99.9% |

(U.S.S. 20–40 mesh)

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 10

Granule

| | |
|---|---|
| 1,3-Dihydro-N—[(4-methoxy-6-methylpyrimidin-2-yl)-aminocarbonyl]-6-methyl-3-oxofuro 3,4-c]pyridine-4-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 11

Low Strength Granule

| | |
|---|---|
| 1,3-Dihydro-N—[(4-methoxy-6-methylpyrimidin-2-yl)-aminocarbonyl]-6-methyl-3-oxofuro[3,4-c]pyridine-4-sulfonamide | 1% |
| N,N—dimethylformamide | 9% |
| attapulgite granules | 90% |

(U.S.S. 20–40 sieve)

The active ingredient is dissolved in the solvent and the solution is sprayed upon dedusted granules in a double cone blender. After spraying of the solution has been completed, the blender is allowed to run for a short period and then the granules are packaged.

EXAMPLE 12

Aqueous Suspension

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 40.0% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 13

Solution

| | |
|---|---|
| 1,3-Dihydro-N—[(4-methoxy-6-methylpyrimidin-2-yl)-aminocarbonyl]-6-methyl-3-oxofuro[3,4-c]pyridine-4-sulfonamide, sodium salt | 5% |
| water | 95% |

The salt is added directly to the water with stirring to produce the solution, which may than be packaged for use.

EXAMPLE 14

High Strength Concentrate

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 99.0% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 15
Wettable Powder

| | |
|---|---|
| 1,3-Dihydro-N—[(4-methoxy-6-methylpyrimidin-2-yl)-aminocarbonyl]-6-methyl-3-oxofuro[3,4-c]pyridine-4-sulfonamide | 90.0% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 16
Wettable Powder

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 17
Oil Suspension

| | |
|---|---|
| 1,3-Dihydro-N—[(4-methoxy-6-methylpyrimidin-2-yl)-aminocarbonyl]-6-methyl-3-oxofuro[3,4-c]pyridine-4-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 18
Dust

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 19
Oil Suspension

| | |
|---|---|
| 1,3-Dihydro-N—[(4-methoxy-6-methylpyrimidin-2-yl)-aminocarbonyl]-6-methyl-3-oxofuro[3,4-c]pyridine-4-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 20
Wettable Powder

| | |
|---|---|
| N—[(4,6-dimethoxypyrimidin-2-yl)aminocarbonyl]-1,3-dihydro-6-methyl-3-oxofuro[3,4-c]pyridine-4-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

The compounds of the present invention are expected to be active herbicides. They should have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate, time and method of application, one may use the compounds of this invention to modify plant growth beneficially, or to selectively control weeds in crops such as wheat and barley.

The rates of application for the compounds of the invention will be determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide examples of which are those of the triazine, triazole, uracil, urea, amide, diphenylether, carbamate and bipyridylium types.

Test A

Seeds of crabgrass (*Digitaria* spp.), barnyardgrass (*Echinochloa crusgalli*), wild oats (Avena fatua), cheatgrass (*Bromus secalinus*), giant foxtail (*Setaria faberii*), velvetleaf (*Abutilon theophrasti*), morningglory (*Ipomoea* sp.), cocklebur (*Xanthium pensylvanicum*), sorghum, corn, soybean, sugarbeet, cotton, rice, wheat, barley and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

Compounds

| Compound | X | Y | Z |
|---|---|---|---|

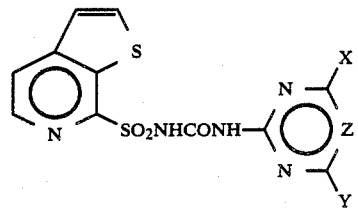

| 1 | OCH₃ | OCH₃ | CH |
| 2 | CH₃ | CH₃ | CH |
| 3 | CH₃ | OCH₃ | CH |
| 4 | Cl | OCH₃ | CH |
| 5 | CH₃ | OCH₃ | N |
| 6 | OCH₃ | OCH₃ | N |

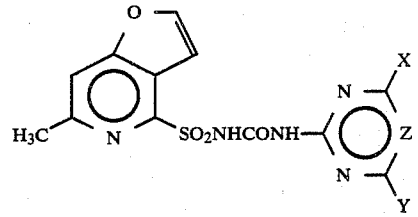

| 7 | OCH₃ | OCH₃ | CH |
| 8 | CH₃ | CH₃ | CH |
| 9 | Cl | OCH₃ | CH |
| 10 | CH₃ | OCH₃ | N |
| 11 | OCH₃ | OCH₃ | N |

Compound 12

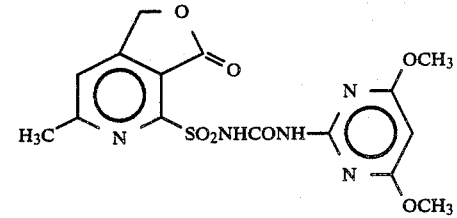

TABLE A

| | Compound 1 | | Cmpd. 2 | Compound 3 | | Cmpd. 4 | Cmpd. 5 | Cmpd. 6 |
|---|---|---|---|---|---|---|---|---|
| Rate kg/ha | 0.05 | 0.01 | 0.05 | 0.05 | 0.01 | 0.05 | 0.05 | 0.05 |
| POSTEMERGENCE | | | | | | | | |
| Morningglory | 10C | 10C | 3C,8G | 10C | 9C | 4C,9G | 10C | 5C,9G |
| Cocklebur | 10C | 10C | 3C,9H | 10C | 9C | 9H | 4C,9H | 4C,8H |
| Velvetleaf | 10C | 10C | 10C | 10C | 10C | 9C | 8H | 3C,8H |
| Nutsedge | 3C,8G | 3C,7G | 3C,9G | 4C,9G | 2C,8G | 5G | 0 | 3G |
| Crabgrass | 3C,5G | 2G | 2G | 6G | 3G | 0 | 0 | 0 |
| Giant Foxtail | 9C | 2C,7G | 0 | 2C,7G | 1H | 0 | 0 | 0 |
| Barnyardgrass | 9H | 3C,7H | 9H | 9H | 4H | 3H | 3H | 2C,5H |
| Cheatgrass | 4C,9G | 6G | 2G | 2C,9G | 4G | 0 | 0 | 0 |
| Wild Oats | 2C,5G | 0 | 0 | 2C,3G | 0 | 0 | 0 | 0 |
| Wheat | 3G | 0 | 0 | 5G | 2G | 2G | 0 | 0 |
| Corn | 5C,9G | 4C,9G | 3C,9H | 3C,9G | 2C,9G | 7G | 2C,5H | 0 |
| Barley | 2G | 0 | 0 | 3G | 0 | 0 | 0 | 0 |
| Soybean | 9C | 9C | 4C,9G | 9C | 5C,9G | 7H | 7H | 2C,8G |
| Rice | 9C | 3C,7G | 4C,9G | 5C,9G | 8G | 7G | 2G | 3G |
| Sorghum | 9G | 3C,8G | 4C,9G | 4C,9G | 2C,7G | 4C,9G | 2C,8H | 3G |
| Sugar beet | 10C | 10C | 9C | 10C | 9C | 9C | 9C | 2C,8G |
| Cotton | 10C | 10C | 4C,9G | 10C | 5C,9G | 9C | 9G | 8G |
| PREEMERGENCE | | | | | | | | |
| Morningglory | 5G | 4G | 5H | 6G | 3G | 2G | 3G | 7G |
| Cocklebur | 8G | 8H | — | 9H | 9H | 0 | 0 | 3H |
| Velvetleaf | 8G | 9G | 9G | 9G | 4C,9G | 0 | 4G | 5H |
| Nutsedge | 3G | 0 | 5G | 8G | 0 | 0 | 0 | 0 |
| Crabgrass | 2G | 0 | 0 | 0 | 0 | 0 | 0 | 0 |
| Giant Foxtail | 3G | 0 | 2C | 2C,3H | 2G | 0 | 0 | 0 |
| Barnyardgrass | 3G | 1C | 2C,3G | 3C,7G | 3G | 0 | 0 | 0 |
| Cheatgrass | 7G | 0 | 0 | 6G | 4G | 0 | 0 | 0 |
| Wild Oats | 0 | 0 | 0 | 2G | 0 | 0 | 0 | 0 |
| Wheat | 3G | 0 | 0 | 0 | 0 | 0 | 0 | 0 |
| Corn | 9H | 7G | 2C,6G | 9H | 7G | 0 | 3G | 3G |

TABLE A-continued

| | Compound 7 | | Cmpd. 8 | Cmpd. 9 | Cmpd. 10 | Cmpd. 11 | Compound 12 | |
|---|---|---|---|---|---|---|---|---|
| Rate kg/ha | 0.05 | 0.01 | 0.05 | 0.05 | 0.05 | 0.05 | 0.05 | 0.01 |
| Barley | 4G | 0 | 0 | 0 | 0 | 0 | 0 | 0 |
| Soybean | 8H | 7G | 4H | 9H | 4H | 0 | 1H | 3H |
| Rice | 9H | 6H | 8H | 9H | 10E | 0 | 0 | 0 |
| Sorghum | 2C,8H | 6G | 3C,9H | 2C,6G | 2C,8G | 0 | 0 | 0 |
| Sugar beet | 3C,8G | 8G | 7G | 9G | 7G | 5G | 3H | 0 |
| Cotton | 9G | 8G | 4G | 9G | 8G | 7G | 3G | 7G |
| *POSTEMERGENCE* | | | | | | | | |
| Morningglory | 4C,9H | 2C,6G | 0 | 2C,4G | 1H | 2C,4G | 0 | 0 |
| Cocklebur | 10C | 8H | 1H | 6G | 2G | 4G | 3G | 0 |
| Velvetleaf | 5C,9G | 8G | 3G | 0 | 2G | 2G | 2G | 0 |
| Nutsedge | 9G | 2C,8G | 0 | 3G | 0 | 0 | 0 | 0 |
| Crabgrass | 4G | 0 | 0 | 0 | 0 | 0 | 2C,3G | 0 |
| Giant Foxtail | 3G | 0 | 0 | 0 | 0 | 0 | 3C,6G | 3G |
| Barnyardgrass | 9H | 2C,7H | 0 | 0 | 0 | 0 | 0 | 0 |
| Cheatgrass | 4G | 0 | 0 | 0 | 0 | 0 | 2G | 0 |
| Wild Oats | 0 | 0 | 0 | 0 | 0 | 0 | 3C,8G | 2G |
| Wheat | 2G | 0 | 0 | 0 | 0 | 0 | 2C,5G | 0 |
| Corn | 9H | 2C,5H | 2H | 2C,5H | 1C,5H | 3H | 3C,8H | 5H |
| Barley | 0 | 0 | 0 | 0 | 0 | 0 | 2C,4G | 2G |
| Soybean | 4C,9G | 7H | 0 | 2H | 2H | 2H | 0 | 0 |
| Rice | 2C,8G | 4G | 2G | 4G | 2G | 0 | 4C,8G | 2G |
| Sorghum | 7G | 0 | 0 | 2G | 0 | 2G | 3C,6G | 2G |
| Sugar beet | 10C | 4C,9G | 1C | 3G | 2H | 2C,5G | 3H | 0 |
| Cotton | 4C,9G | 5G | 2G | 0 | 2G | 4G | 0 | 0 |
| *PREEMERGENCE* | | | | | | | | |
| Morningglory | 4G | 3H | 0 | 0 | 0 | 0 | 0 | 0 |
| Cocklebur | 8H | 7H | 0 | 0 | — | 0 | 0 | 0 |
| Velvetleaf | 7H | 5G | 0 | 0 | 0 | 0 | 0 | 0 |
| Nutsedge | 5G | 0 | 0 | 0 | 0 | 0 | 0 | 0 |
| Crabgrass | 0 | 0 | 0 | 0 | 0 | 0 | 0 | 0 |
| Giant Foxtail | 0 | 0 | 0 | 0 | 0 | 0 | 0 | 0 |
| Barnyardgrass | 8H | 0 | 0 | 0 | 0 | 0 | 0 | 0 |
| Cheatgrass | 0 | 0 | 0 | 0 | 0 | 0 | 0 | 0 |
| Wild Oats | 0 | 0 | 0 | 0 | 0 | 0 | 0 | 0 |
| Wheat | 0 | 0 | 0 | 0 | 0 | 0 | 0 | 0 |
| Corn | 4G | 4G | 0 | 0 | 0 | 2G | 0 | 0 |
| Barley | 0 | 0 | 0 | 0 | 0 | 0 | 0 | 0 |
| Soybean | 3G | 0 | 0 | 0 | 0 | 0 | 0 | 0 |
| Rice | 4G | 0 | 0 | 0 | 0 | 0 | 0 | 0 |
| Sorghum | 3G | 4G | 0 | 0 | 0 | 0 | 0 | 0 |
| Sugar beet | 7G | 4G | 0 | 0 | 0 | 0 | 8G | 5G |
| Cotton | 7G | 1H | 0 | 0 | 0 | 0 | 0 | 0 |

What is claimed is:

1. A compound of the formula

wherein J is:

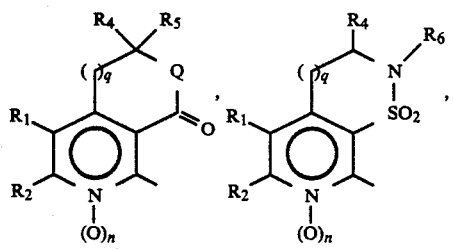

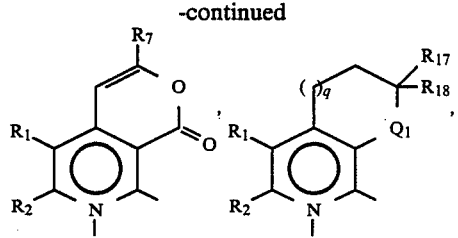

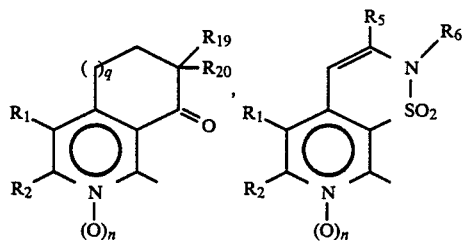

-continued
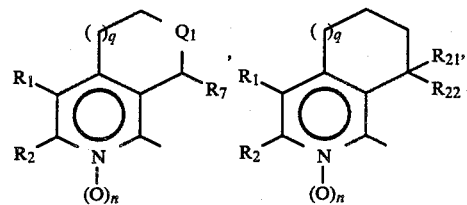
J₁₃, J₁₅
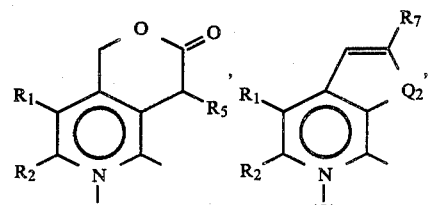
J₁₇, J₁₉
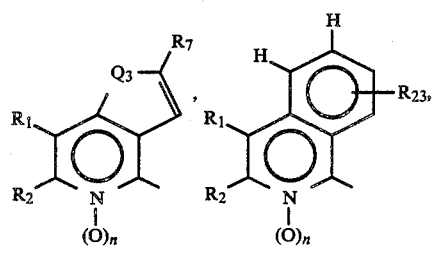
J₂₁, J₂₃
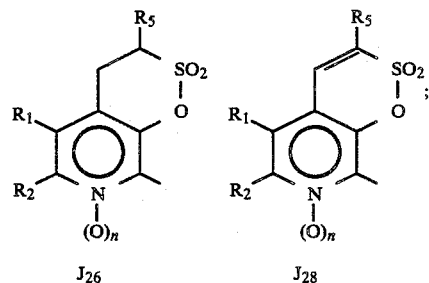
J₂₆, J₂₈
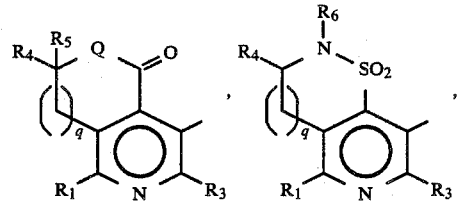
J₂, J₄
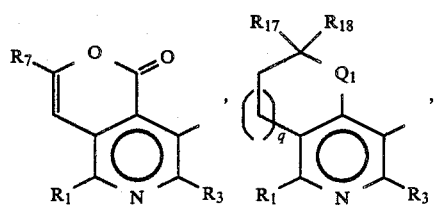
J₆, J₈
-continued
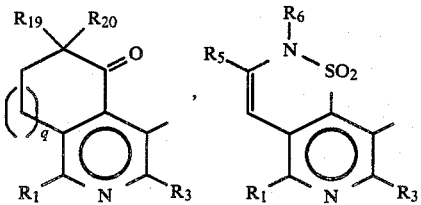
J₁₀, J₁₂
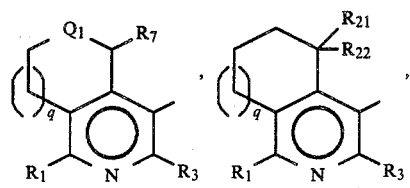
J₁₄, J₁₆
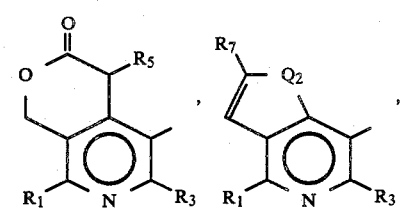
J₁₈, J₂₀
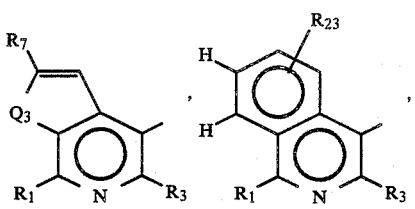
J₂₂, J₂₄
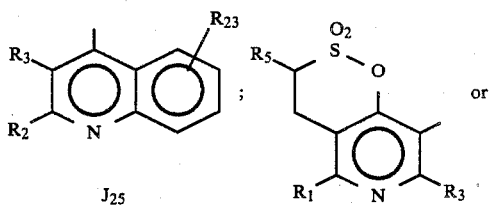
J₂₅, J₂₇
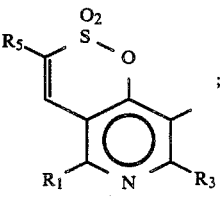
J₂₉
q is 0 or 1;

Q is O, S or NR$_4$;
Q$_1$ is O, S, SO, SO$_2$, NH or NCH$_3$;
Q$_2$ is O, S, NH, NCH$_3$, CH$_2$ or CHCH$_3$;
Q$_3$ is O, S, NH, NCH$_3$ or CH$_2$;
R$_4$ is H or C$_1$-C$_4$ alkyl;
R$_5$ is H or CH$_3$;
R$_7$ is H or C$_1$-C$_3$ alkyl;
R$_{17}$ is H or C$_1$-C$_4$ alkyl;
R$_{18}$ is H or CH$_3$;
R$_{19}$ is H, F, Cl or C$_1$-C$_4$ alkyl;
R$_{20}$ is H, F, Cl or CH$_3$;
R$_{21}$ is H, C$_1$-C$_3$ alkyl, C$_1$-C$_3$ alkoxy, F or Cl;
R$_{22}$ is H, CH$_3$, C$_1$-C$_3$ alkoxy, F, Cl or OH; or R$_{21}$ and R$_{22}$ can be taken together to form —OCH$_2$CH$_2$O— or —OCH$_2$CH$_2$CH$_2$O—;
R$_{23}$ is H, C$_1$-C$_3$ alkyl, C$_1$-C$_3$ alkoxy, Cl, Br or F;
W is O or S;
R is H or CH$_3$;
n is 0 or 1;
R$_1$ is H, CH$_3$, OCH$_3$ or Cl;
R$_2$ is H, C$_1$-C$_3$ alkyl, Cl, Br, F, C$_1$-C$_3$ alkoxy, C$_1$-C$_3$ alkylthio, CF$_3$, CH$_2$OCH$_3$, CH$_2$SCH$_3$ or CH$_2$CN;
R$_3$ is H, C$_1$-C$_3$ alkyl, halogen, C$_1$-C$_3$ alkoxy, C$_1$-C$_3$ alkylthio, C$_1$-C$_2$ alkylsulfonyl, C$_1$-C$_2$ alkylcarbonyl, C$_1$-C$_2$ alkoxycarbonyl, C$_3$-C$_4$ alkenyl, NO$_2$, NH$_2$, C$_1$-C$_2$ alkyl amino, di(C$_1$-C$_2$)-alkylamino, C$_1$-C$_2$ alkylsulfamoyl, di(C$_1$-C$_2$)-alkylsulfamoyl, (C$_1$-C$_2$ alkyl)aminocarbonyl, di(C$_1$-C$_2$ alkyl)aminocarbonyl or C$_3$-C$_4$ alkynyl;
R$_6$ is H, R$_8'$, SR$_8'$, SO$_2$R$_8'$, OR$_8'$, C(O)R$_8$, CO$_2$R$_8'$, (CO)$_2$OR$_8$, (CO)$_2$R$_8'$, C(O)NR$_9$R$_{10}$, C(O)NRA, C(S)SR$_8'$, NH$_2$, NR$_9$R$_{10}$, OH, CN, P(O)R$_{11}$R$_{12}$, P(S)R$_{11}$R$_{12}$ or Si(CH$_3$)$_2$R$_{13}$;
R$_8$ is C$_1$-C$_{10}$ alkyl, C$_3$-C$_{10}$ alkoxyalkoxyalkyl, C$_2$-C$_{10}$ alkenyl, C$_3$-C$_{10}$ epoxyalkyl, C$_2$-C$_{10}$ alkynyl, C$_3$-C$_6$ cycloalkyl, C$_4$-C$_7$ cycloalkylalkyl or phenyl optionally substituted with R$_{14}$ when R$_8$ is C$_3$-C$_6$ cycloalkyl or C$_4$-C$_7$ cycloalkylalkyl, it may optionally be substituted by C$_1$-C$_4$ alkyl, 1 to 3 atoms of Cl or F or 1 Br; when R$_8$ is C$_1$-C$_{10}$ alkyl, C$_2$-C$_{10}$ alkenyl or C$_2$-C$_{10}$ alkynyl, it may optionally be substituted by one or more halogens and/or by (R$_{15}$)$_r$ provided that when r is 2, the values of R$_{15}$ may be identical or different;
R$_8'$ is C$_1$-C$_{10}$ alkyl, C$_3$-C$_{10}$ alkoxyalkoxyalkyl, C$_3$-C$_{10}$ alkenyl, C$_3$-C$_{10}$ epoxyalkyl, C$_3$-C$_{10}$ alkynyl, C$_3$-C$_6$ cycloalkyl, C$_4$-C$_7$ cycloalkylalkyl or phenyl optionally substituted with R$_{14}$; when R$_8'$ is C$_3$-C$_6$ cycloalkyl or C$_4$-C$_7$ cycloalkylalkyl, it may optionally be substituted by C$_1$-C$_4$ alkyl, 1 to 3 atoms of Cl or F or 1 Br; when R$_8'$ is C$_1$-C$_{10}$ alkyl, C$_3$-C$_{10}$ alkenyl or C$_3$-C$_{10}$ alkynyl, it may optionally be substituted by one or more halogens and/or by (R$_{15}$)$_r$ provided that when r is 2, the values of R$_{15}$ may be identical or different;
r is 0, 1 or 2;
R$_9$ is H or C$_1$-C$_4$ alkyl;
R$_{10}$ is H, C$_1$-C$_{10}$ alkyl, C$_1$-C$_{10}$ haloalkyl, C$_3$-C$_{10}$ alkenyl, C$_3$-C$_{10}$ alkynyl, C$_3$-C$_6$ cycloalkyl or phenyl substituted with R$_{14}$;
R$_{10}'$ is C$_1$-C$_{10}$ alkyl, C$_1$-C$_{10}$ haloalkyl, C$_3$-C$_{10}$ alkenyl, C$_3$-C$_{10}$ alkynyl, C$_3$-C$_6$ cycloalkyl or phenyl substituted with R$_{14}$;
R$_{11}$ and R$_{12}$ are independently C$_1$-C$_4$ alkyl, C$_1$-C$_4$ alkoxy or C$_1$-C$_4$ alkylthio;
R$_{13}$ is C$_1$-C$_{10}$ alkyl, benzyl or phenyl optionally substituted with R$_{14}$;

R$_{14}$ is H, F, Cl, Br, CH$_3$, OCH$_3$, NO$_2$, CN, SCH$_3$, SO$_2$CH$_3$ or CF$_3$;
R$_{15}$ is OR$_{10}$, OC(O)R$_{10}$, OC(O)NR$_9$R$_{10}$, OSO$_2$R$_{10}'$, OP(O)R$_{11}$R$_{12}$, OSi(CH$_3$)$_2$R$_{13}$, SR$_{10}'$, SOR$_{10}'$, SO$_2$R$_{10}'$, SCN, CN, SP(O)R$_{11}$R$_{12}$, SP(S)R$_{11}$R$_{12}$, P(O)R$_{11}$R$_{12}$, P(S)R$_{11}$R$_{12}$, NR$_9$R$_{10}$, N+R$_9$R$_{10}$R$_{13}$, NR$_9$C(O)R$_{10}$, NR$_9$C(O)OR$_{10}'$, NR$_9$C(O)NR$_9$R$_{10}$, NR$_9$SO$_2$R$_{10}'$, NR$_9$P(O)R$_{11}$R$_{12}$, NR$_9$P(S)R$_{11}$R$_{12}$, NO$_2$, C(O)R$_{10}$, C(O)OR$_{10}$, C(O)NR$_9$R$_{10}$, C(R$_{10}$)=NOR$_{12}$, naphthyl, phenyl optionally substituted with R$_{14}$ and/or R$_{16}$,

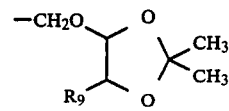

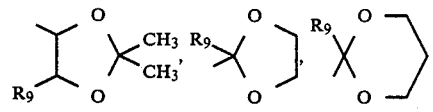

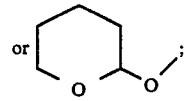

R$_{16}$ is H, F, Cl, Br,

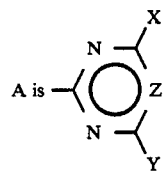

X is H, C$_1$-C$_4$ alkyl, C$_1$-C$_4$ alkoxy, C$_1$-C$_4$ haloalkoxy, C$_1$-C$_4$ haloalkyl, C$_1$-C$_4$ haloalkylthio, C$_1$-C$_4$ alkylthio, halogen, C$_2$-C$_5$ alkoxyalkoxy, amino, C$_1$-C$_3$ alkylamino or di(C$_1$-C$_3$ alkyl)amino;
Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$C$_4$ alkenyloxy, C$_3$-C$_4$ alkynyloxy, C$_2$-C$_5$ alkylsulfinylalkyl, C$_1$-C$_4$ haloalkyl, C$_2$-C$_5$ alkylsulfonylalkyl, C$_3$-C$_5$ cycloalkyl, C$_2$-C$_4$ alkynyl, C$_2$-C$_5$ alkylthioalkyl,

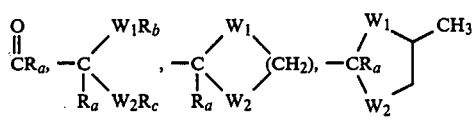

or N(OCH$_3$)CH$_3$;
W$_1$ and W$_2$ are independently O or S;
m is 2 or 3;
R$_a$ is H or CH$_3$;
R$_b$ is C$_1$-C$_2$ alkyl;
R$_c$ is C$_1$-C$_2$ alkyl;
Z is CH, CCH$_3$, CC$_2$H$_5$, CCl or CBr;
and their agriculturally suitable salts; provided that:
(a) when W is S, then R is H, Z is CH and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

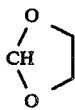

(b) when X is Cl, Br, F or I, then Z is CH and Y is OCH$_3$, OC$_2$H$_5$, NH$_2$, NHCH$_3$, N(CH)$_2$, OCF$_2$H;

(c) when X or Y is C$_1$ haloalkoxy, then Z is CH;

(d) when J is J$_1$, J$_3$, J$_5$, J$_7$, J$_9$, J$_{11}$, J$_{13}$, J$_{15}$, J$_{17}$, J$_{19}$, J$_{21}$, J$_{23}$, J$_{26}$ or J$_{28}$, then either R$_1$ or R$_2$ is H;

(e) when the total number of carbon atoms in X and Y is greater than 4, then the total number of carbon atoms in J is less than or equal to 15;

(f) the total number of carbon atoms in R$_6$ is less than or equal to 12; and (g) when R$_{15}$ and the bridging sulfonamide nitrogen of J$_3$, J$_4$, J$_{11}$ or J$_{12}$ is attached to the same carbon then R$_{15}$ is other than OH, SH, OC(O)R$_{10}$, OC(O)NR$_9$R$_{10}$, OSO$_2$R'$_{10}$, OP(O)R$_{11}$, R$_{12}$, OS:(CH$_3$)$_2$R$_{13}$, SP(O)R$_{11}$R$_{12}$, SP(S)R$_{11}$R$_{12}$, NR$_9$R$_{10}$ or N+R$_9$R$_{10}$R$_{13}$;

(h) the total number of carbon atoms in R$_{19}$ and R$_{20}$ is less than or equal to 4;

(i) the total number of carbon atoms in R$_4$ and R$_5$ is less than or equal to 4;

(j) when R$_{21}$ is C$_1$-C$_3$ alkoxy, then R$_{22}$ is H, CH$_3$ or C$_1$-C$_3$ alkoxy; and (k) when R$_{22}$ is OH, then R$_{21}$ is H or C$_1$-C$_3$ alkyl, and when R$_{22}$ is C$_1$-C$_3$ alkoxy, then R$_{21}$ is H, C$_1$-C$_3$ alkyl or C$_1$-C$_3$ alkoxy.

2. Compounds of claim 1 where J is

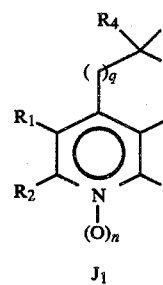

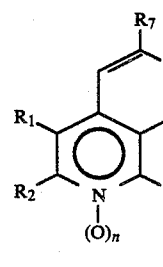

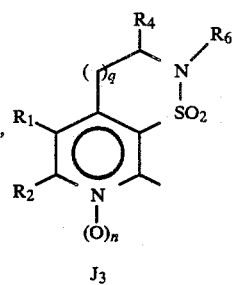

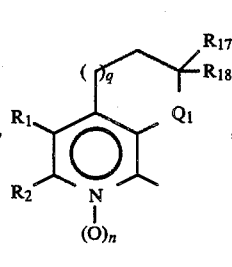

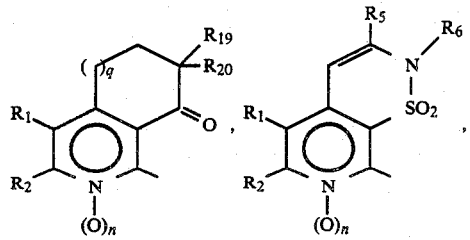

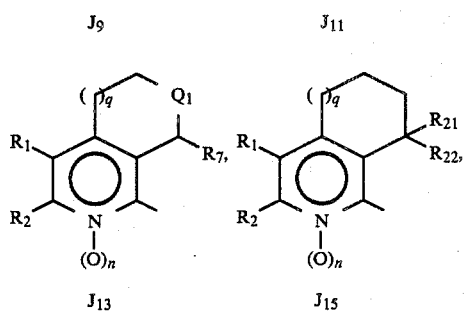

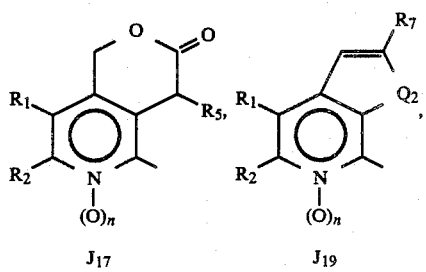

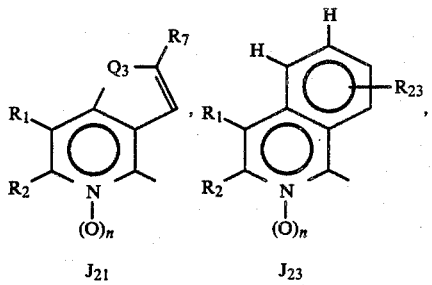

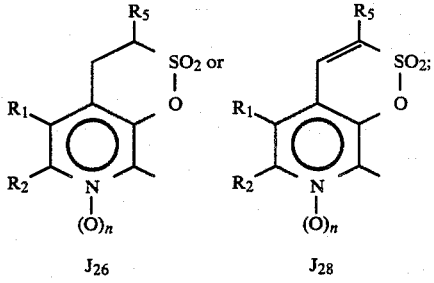

q is 0 or 1;
Q is O, S, or NR$_4$;
Q$_1$ is O, S, SO, SO$_2$, NH or NCH$_3$;
Q$_2$ is O, S, NH, NCH$_3$, CH$_2$ or CHCH$_3$;
Q$_3$ is O, S, NH, NCH$_3$ or CH$_2$;
R$_4$ is H or C$_1$-C$_4$ alkyl;
R$_5$ is H or CH$_3$;
R$_7$ is H or C$_1$-C$_3$ alkyl;
R$_{17}$ is H or C$_1$-C$_4$ alkyl;
R$_{18}$ is H or CH$_3$;

R$_{19}$ is H, F, Cl or C$_1$-C$_4$ alkyl;
R$_{20}$ is H, F, Cl or CH$_3$;
R$_{21}$ is H, C$_1$-C$_3$ alkyl, C$_1$-C$_3$ alkoxy, F or Cl;
R$_{22}$ is H, CH$_3$, C$_1$-C$_3$ alkoxy, F, Cl or OH; or
R$_{21}$ and R$_{22}$ can be taken together to form —OCH$_2$C-H$_2$O— or —OCH$_2$CH$_2$CH$_2$O—;
R$_{23}$ is H, C$_1$-C$_3$ alkyl, C$_1$-C$_3$ alkoxy, Cl, Br or F;
provided that
(a) the total number of carbon atoms in R$_{19}$ and R$_{20}$ is less than or equal to 4;
(b) the total number of carbon atoms in R$_4$ and R$_5$ is less than or equal to 4;
(c) when R$_{21}$ is C$_1$-C$_3$ alkoxy, then R$_{22}$ is H, CH$_3$ or C$_1$-C$_3$ alkoxy; and
(d) when R$_{22}$ is OH, then R$_{21}$ is H or C$_1$-C$_3$ alkyl, and when R$_{22}$ is C$_1$-C$_3$ alkoxy, then R$_{21}$ is H, C$_1$-C$_3$ alkyl or C$_1$-C$_3$ alkoxy.

3. Compounds of claim 2 where
n is 0;
W is O;
R is H;
X is CH$_3$, OCH$_3$, OC$_2$H$_5$, Cl, Br, F, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, CH$_2$SCH$_2$CH$_3$, $$\underset{CR_a,}{\overset{O}{\|}} \underset{R_a}{\overset{W_1R_b}{-C}} \underset{W_2R_c}{}, \quad \underset{R_a}{\overset{W_1}{C}} \underset{W_2}{\overset{}{}}(CH_2)_m, \quad CR_a \underset{W_2}{\overset{W_1}{\diagdown}} \underset{}{\overset{CH_3}{}}$$

OCF$_2$H, SCF$_2$H, CH=CH or C≡CCH$_3$; and
Z is CH.

4. Compounds of claim 3 where
R$_2$ is H, CH$_3$, OCH$_3$, Cl or Br;
R$_6$ is H, R$_8'$, C(O)R$_8$ or CO$_2$R$_8'$;
R$_8$ and R$_8'$ are C$_1$-C$_6$ alkyl, C$_1$-C$_6$ haloalkyl, C$_3$-C$_6$ alkneyl, C$_3$-C$_6$ haloalkenyl, C$_3$-C$_6$ alkynyl, C$_3$-C$_6$ epoxyalkyl or C$_1$-C$_4$ alkyl substituted with C$_1$-C$_2$ alkoxy, C$_1$-C$_2$ alkylthio, C$_1$-C$_2$ alkylsulfinyl, C$_1$-C$_2$ alkylsulfonyl, CO$_2$(C$_1$-C$_2$ alkyl), C(O)C$_1$-C$_2$ alkyl, CN or OH;
R$_{19}$ is H or C$_1$-C$_3$ alkyl;
R$_{20}$ is H or CH$_3$;
R$_{21}$ is H, C$_1$-C$_3$ alkyl or C$_1$-C$_2$ alkoxy;
R$_{22}$ is H, CH$_3$, C$_1$-C$_2$ alkoxy or OH; or
R$_{21}$ and R$_{22}$ may be taken together to form —OCH$_2$CH$_2$O— or —OCH$_2$CH$_2$CH$_2$O—; and
R$_{23}$ is H, CH$_3$, Cl, Br or OCH$_3$.

5. Compounds of claim 4 where
R$_8$ and R$_8'$ are C$_1$-C$_6$ alkyl, C$_1$-C$_4$ haloalkyl, C$_3$-C$_4$ alkenyl, C$_3$-C$_4$ haloalkenyl, C$_3$-C$_4$ alkynyl, CO$_2$(C$_1$-C$_2$ alkyl), C(O)C$_1$-C$_2$ alkyl or C$_1$-C$_3$ alkyl substituted with C$_1$-C$_2$ alkoxy, C$_1$-C$_2$ alkylthio, C$_1$-C$_2$ alkylsulfonyl or CN.

6. Compounds of claim 5 where
X is CH$_3$, OCH$_3$, OC$_2$H$_5$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

7. Compounds of claim 6 where J is J$_1$.
8. Compounds of claim 6 where J is J$_3$.
9. Compounds of claim 6 where J is J$_5$.
10. Compounds of claim 6 where J is J$_7$.
11. Compounds of claim 6 where J is J$_9$.
12. Compounds of claim 6 where J is J$_{11}$.
13. Compounds of claim 6 where J is J$_{13}$.
14. Compounds of claim 6 where J is J$_{15}$.
15. Compounds of claim 6 where J is J$_{17}$.
16. Compounds of claim 6 where J is J$_{19}$.
17. Compounds of claim 6 where J is J$_{21}$.
18. Compounds of claim 6 where J is J$_{23}$.
19. Compounds of claim 6 where J is J$_{26}$.
20. Compounds of claim 6 where J is J$_{28}$.
21. Compounds of claim 1 where J is

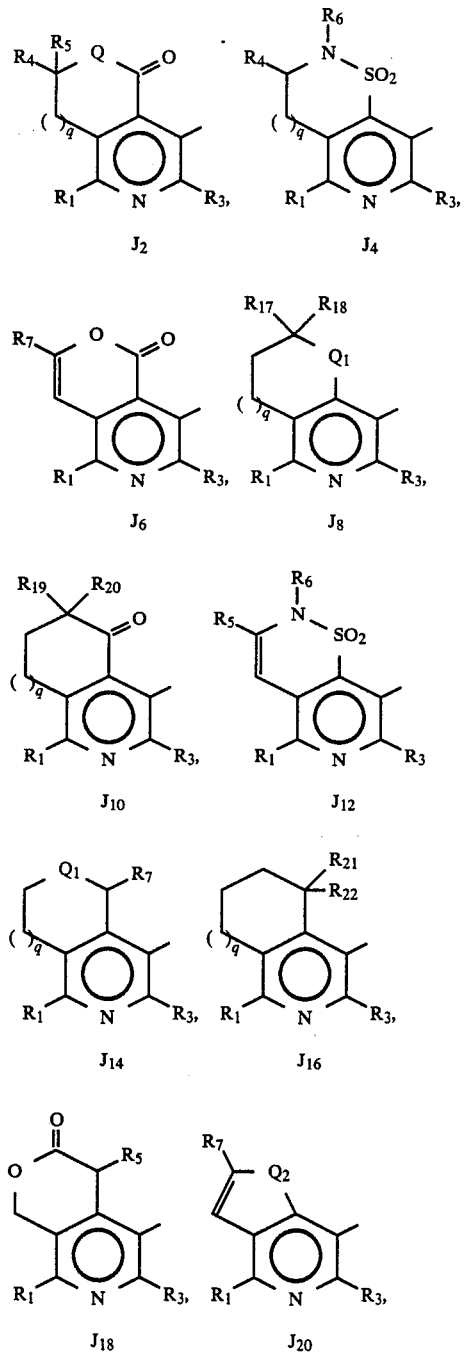

-continued

[Structures: J22, J24, J27, J29]

q is 0 or 1;
Q is O, S, or NR4;
Q1 is O, S, SO, SO2, NH or NCH3;
Q2 is O, S, NH, NCH3, CH2 or CHCH3;
Q3 is O, S, NH, NCH3 or CH2;
R4 is H or C1-C4 alkyl;
R5 is H or CH3;
R7 is H or C1-C3 alkyl;
R17 is H or C1-C4 alkyl;
R18 is H or CH3;
R19 is H, F, Cl or C1-C4 alkyl;
R20 is H, F, Cl or CH3;
R21 is H, C1-C3 alkyl, C1-C3 alkoxy, F or Cl;
R22 is H, CH3, C1-C3 alkoxy, F, Cl or OH; or
R21 and R22 can be taken together to form —OCH2CH2O— or —OCH2CH2CH2O—;
R23 is H, C1-C3 alkyl, C1-C3 alkoxy, Cl, Br or F; provided that
(a) the total number of carbon atoms in R19 and R20 is less than or equal to 4;
(b) the total number of carbon atoms in R4 and R5 is less than or equal to 4;
(c) when R21 is C1-C3 alkoxy, then R22 is H, CH3 or C1-C3 alkoxy; and
(d) when R22 is OH, then R21 is H or C1-C3 alkyl, and when R22 is C1-C3 alkoxy, then R21 is H, C1-C3 alkyl or C1-C3 alkoxy.

22. Compounds of claim 21 where
n is 0;
W is O;
R is H;
X is CH3, OCH3, OC2H5, Cl, Br, F, I, OCF2H, CH2F, CF3, OCH2CH2F, OCH2CHF2, OCH2CF3, CH2Cl or CH2Br;
Y is H, CH3, OCH3, OC2H5, CH2OCH3, NHCH3, N(OCH3)CH3, N(CH3)2, CH2CH3, CF3, SCH3, OCH2CH=CH2, OCH2C≡CH, CH2OCH2CH3, OCH2CH2OCH3, CH2SCH3, CH2SCH2CH3,

[Structures]

OCF2H, SCF2H, CH=CH or C≡CCH3; and
Z is CH.

23. Compounds of claim 22 where
R2 is H, CH3, OCH3, Cl or Br;
R3 is CH3, CH2CH3, F, Cl, Br, OCH3, OCH2CH3, SCH3SCH2CH3, SO2CH3, SO2CH2CH3, SO2N(CH3)2, C(O)NHCH3 or C(O)N(CH3)2;
R6 is H, R8', C(O)R8 or CO2R8';
R8 and R8' are C1-C6 alkyl, C1-C6 haloalkyl, C3-C6 alkenyl, C3-C6 haloalkenyl, C3-C6 alkynyl, C3-C6 epoxyalkyl or C1-C4 alkyl substituted with C1-C2 alkoxy, C1-C2 alkylthio, C1-C2 alkylsulfinyl, C1-C2 alkylsulfonyl, CO2(C1-C2 alkyl), C(O)C1-C2 alkyl, CN or OH;
R19 is H or C1-C3 alkyl;
R20 is H or CH3;
R21 is H, C1-C3 alkyl or C1-C2 alkoxy;
R22 is H, CH3, C1-C2 alkoxy or OH; or
R21 and R22 may be taken together to form —OCH2CH2O— or —OCH2CH2CH2O—; and
R23 is H, CH3, Cl, Br or OCH3.

24. Compounds of claim 23 where
R8 and R8' are C1-C6 alkyl, C1-C4 haloalkyl, C3-C4 alkenyl, C3-C4 haloalkenyl, C3-C4 alkynyl, CO2(C1-C2 alkyl), C(O)C1-C2 alkyl or C1-C3 alkyl substituted with C1-C2 alkoxy, C1-C2 alkylthio, C1-C2 alkylsulfonyl or CN.

25. Compounds of claim 24 where
X is CH3, OCH3, OC2H5, Cl, OCF2H or OCH2CF3; and
Y is CH3, OCH3, C2H5, CH2OCH3, NHCH3 or CH(OCH3)2.

26. Compounds of claim 25 where J is J2.
27. Compounds of claim 25 where J is J4.
28. Compounds of claim 25 where J is J6.
29. Compounds of claim 25 where J is J8.
30. Compounds of claim 25 where J is J10.
31. Compounds of claim 25 where J is J12.
32. Compounds of claim 25 where J is J14.
33. Compounds of claim 25 where J is J16.
34. Compounds of claim 25 where J is J18.
35. Compounds of claim 25 where J is J20.
36. Compounds of claim 25 where J is J22.
37. Compounds of claim 25 where J is J24.
38. Compounds of claim 25 where J is J27.
39. Compounds of claim 25 where J is J29.
40. Compounds of claim 1 where J is

[Structure J25]

and
R23 is H, C1-C3 alkyl, C1-C3 alkoxy, Cl, Br or F.

41. Compounds of claim 40 where
W is O;
R is H;
X is CH3, OCH3, OC2H5, Cl, Br, F, I, OCF2H, CH2F, CF3, OCH2CH2F, OCH2CHF2, OCH2CF3, CH2Cl or CH2Br;
Y is H, CH3, OCH3, OC2H5, CH2OCH3, NHCH3, N(OCH3)CH3, N(CH3)2, CH2CH3, CF3, SCH3, OCH2CH=CH2, OCH2C≡CH, CH2OCH2CH3, OCH2CH2OCH3, CH2SCH3, CH2SCH2CH3,

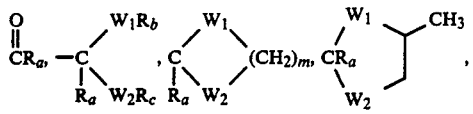

OCF$_2$H, SCF$_2$H, CH≡CH or C≡CCH$_3$; and
Z is CH.

42. Compounds of claim 41 where
R$_2$ is H, CH$_3$, OCH$_3$, Cl or Br;
R$_3$ is H, CH$_3$, CH$_2$CH$_3$, F, Cl, Br, OCH$_3$, OCH$_2$CH$_3$, SCH$_3$, SCH$_2$CH$_3$, SO$_2$CH$_3$, SO$_2$CH$_2$CH$_3$, SO$_2$N(CH$_3$)$_2$, C(O)NHCH$_3$ or C(O)N(CH$_3$)$_2$; and
R$_{23}$ is H, CH$_3$, Cl, Br or OCH$_3$.

43. Compounds of claim 42 where
A is A-1;
X is CH$_3$, OCH$_3$, OC$_2$H$_5$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

44. The compound of claim 1 which is N-[(4,6-dimethoxypyrimidin-2-yl)aminocarbonyl]thieno[2,3-C]pyridine-7-sulfonamide.

45. The compound of claim 1 which is N-[(4-methoxy-6-methylpyrimidin-2-yl)aminocarbonyl]-thieno[2,3-C]pyridine-7-sulfonamide.

46. A composition suitable for controlling the growth of undesired vegetation which comprises an effective amount of a compound of claim 1 and at least one of the following: surfactant, solid or liquid diluent.

47. A composition suitable for controlling the growth of undesired vegetation which comprises an effective amount of a compound of claim 2 and at least one of the following: surfactant, solid or liquid diluent.

48. A composition suitable for controlling the growth of undesired vegetation which comprises an effective amount of a compound of claim 21 and at least one of the following: surfactant, solid or liquid diluent.

49. A composition suitable for controlling the growth of undesired vegetation which comprises an effective amount of a compound of claim 40 and at least one of the following: surfactant, solid or liquid diluent.

50. A composition suitable for controlling the growth of undesired vegetation which comprises an effective amount of a compound of claim 44 and at least one of the following: surfactant, solid or liquid diluent.

51. A method for controlling the growth of undesired vegetation which comprises applying to the locus to be protected an effective amount of a compound of claim 1.

52. A method for controlling the growth of undesired vegetation which comprises applying to the locus to be protected an effective amount of a compound of claim 2.

53. A method for controlling the growth of undesired vegetation which comprises applying to the locus to be protected an effective amount of a compound of claim 21.

54. A method for controlling the growth of undesired vegetation which comprises applying to the locus to be protected an effective amount of a compound of claim 40.

55. A method for controlling the growth of undesired vegetation which comprises applying to the locus to be protected an effective amount of a compound of claim 44.

* * * * *